(12) United States Patent
Waldo et al.

(10) Patent No.: US 7,390,640 B2
(45) Date of Patent: Jun. 24, 2008

(54) CIRCULAR PERMUTANT GFP INSERTION FOLDING REPORTERS

(75) Inventors: Geoffrey S. Waldo, Santa Fe, NM (US); Stephanie Cabantous, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/360,178

(22) Filed: Feb. 22, 2006

(65) Prior Publication Data

US 2006/0252063 A1   Nov. 9, 2006

Related U.S. Application Data

(60) Provisional application No. 60/699,269, filed on Jul. 13, 2005, provisional application No. 60/655,284, filed on Feb. 22, 2005.

(51) Int. Cl.
| | |
|---|---|
| C12N 9/02 | (2006.01) |
| C12N 1/20 | (2006.01) |
| C12N 15/00 | (2006.01) |
| C07H 21/04 | (2006.01) |
| C07H 21/02 | (2006.01) |

(52) U.S. Cl. ............... 435/189; 435/252.3; 435/320.1; 435/6; 536/23.1

(58) Field of Classification Search ............... 435/189, 435/252.3, 320.1, 6; 536/23.1, 23.2
See application file for complete search history.

(56) References Cited

U.S. PATENT DOCUMENTS

| 6,448,087 B1 | 9/2002 | Waldo |
| 7,271,241 B2 | 9/2007 | Waldo |

OTHER PUBLICATIONS

Waldo and Cabantous, U.S. Appl. No. 10/973,693, filed Oct. 24, 2004.
Smith and Matthews, 2001, Protein Sci. 10(1): 116.
Arai et al., 2003, J. Mol. Biol. 328(1):273.

*Primary Examiner*—Maryam Monshipouri
(74) *Attorney, Agent, or Firm*—Kenneth K. Sharples

(57) ABSTRACT

Provided are methods of assaying and improving protein folding using circular permutants of fluorescent proteins, including circular permutants of GFP variants and combinations thereof. The invention further provides various nucleic acid molecules and vectors incorporating such nucleic acid molecules, comprising polynucleotides encoding fluorescent protein circular permutants derived from superfolder GFP, which polynucleotides include an internal cloning site into which a heterologous polynucleotide may be inserted in-frame with the circular permutant coding sequence, and which when expressed are capable of reporting on the degree to which a polypeptide encoded by such an inserted heterologous polynucleotide is correctly folded by correlation with the degree of fluorescence exhibited.

8 Claims, 30 Drawing Sheets

FIG. 2
A
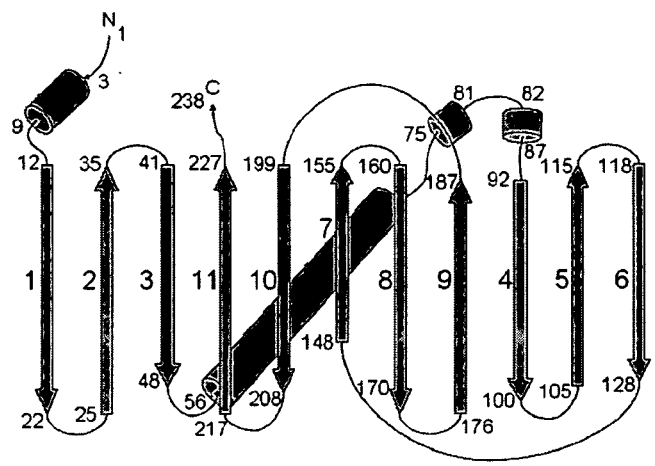
B
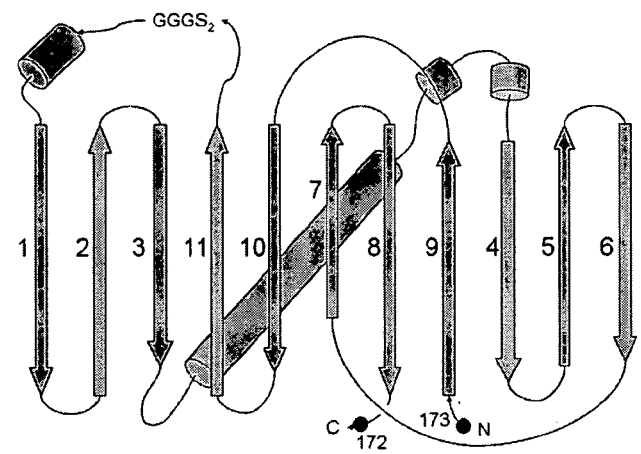
C
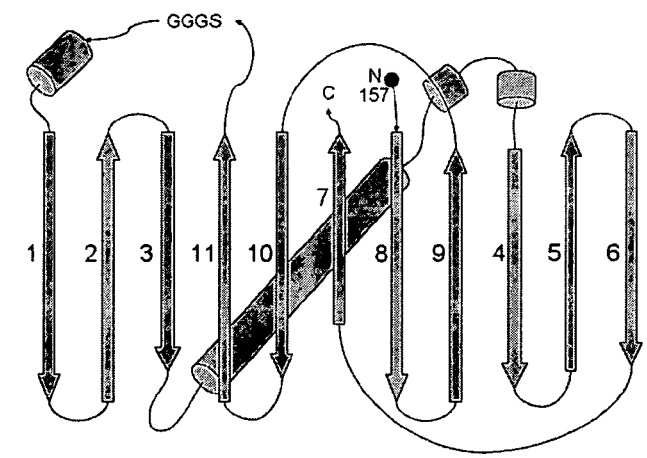

FIG. 3
A
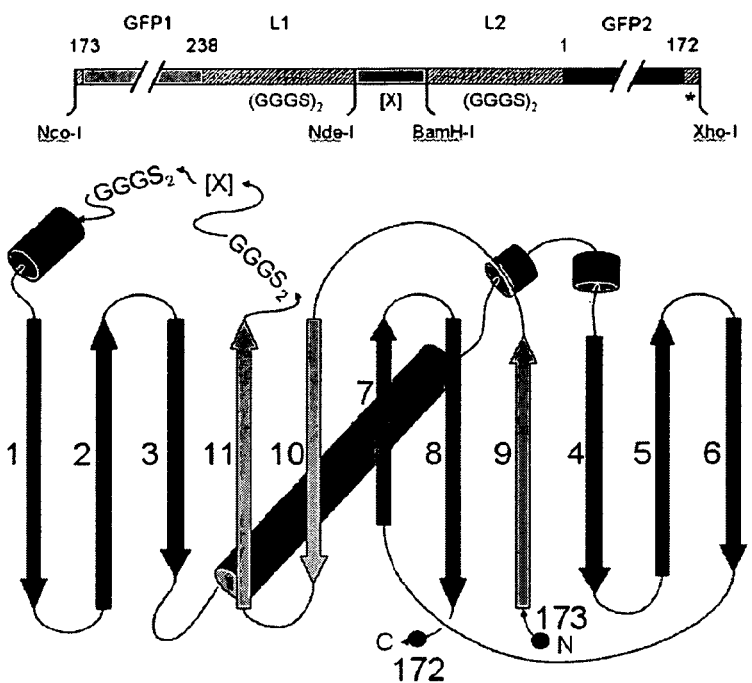
B
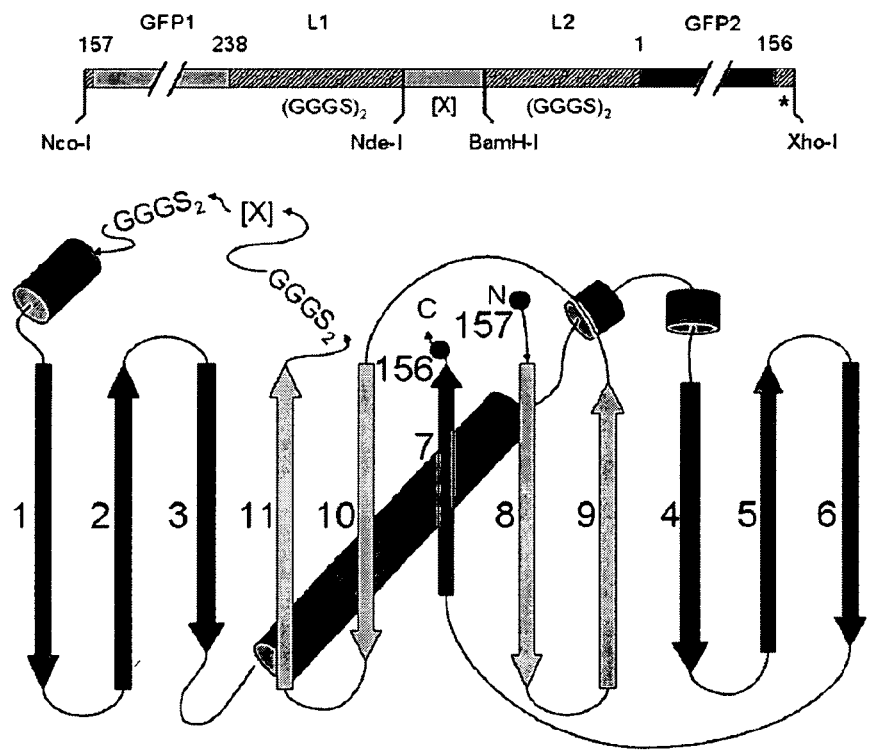

FIG. 4
A
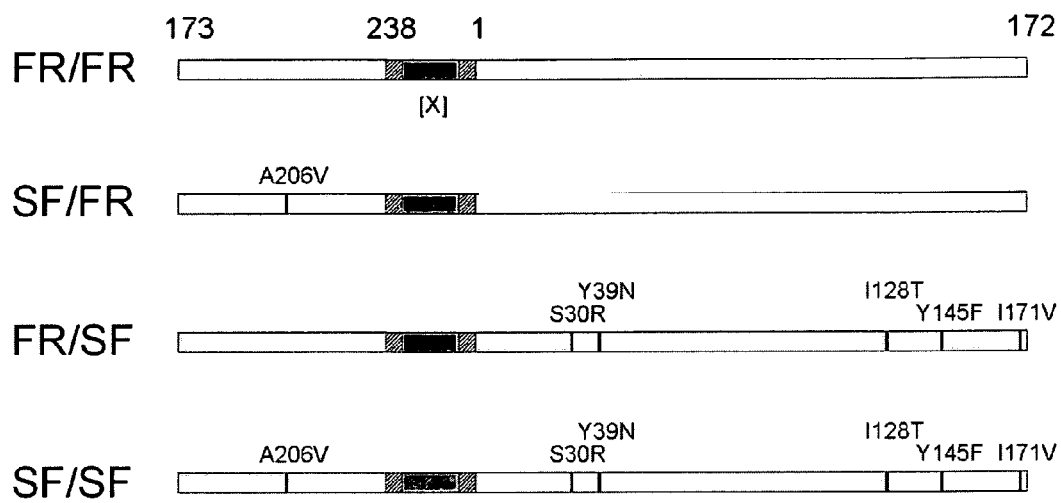
B
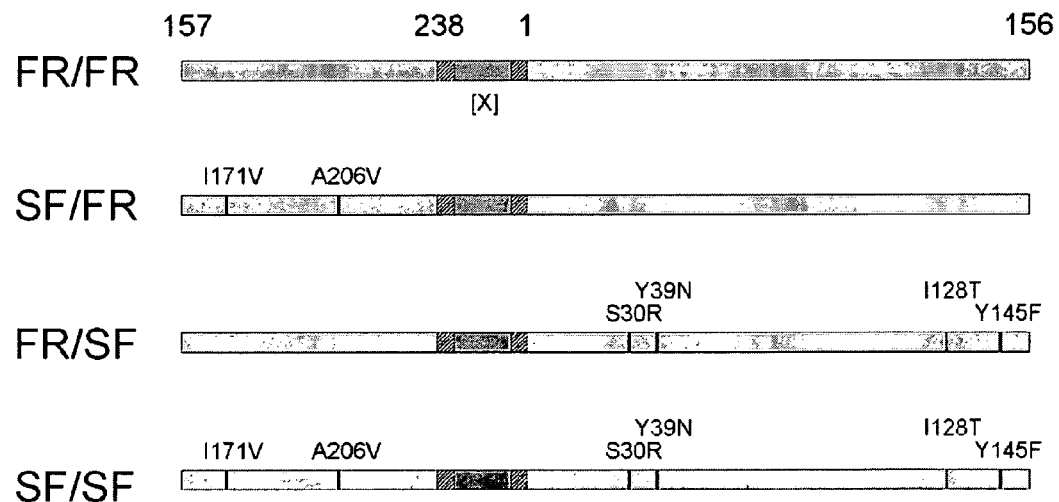

FIG. 6
A
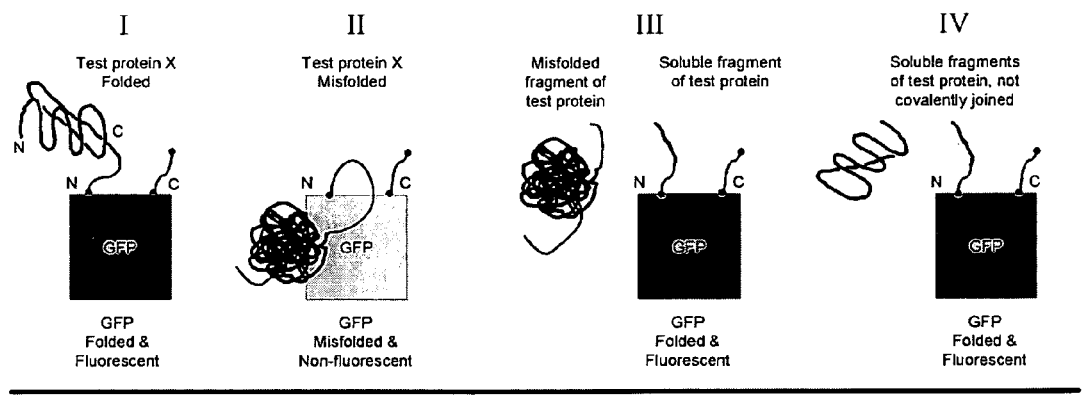
B
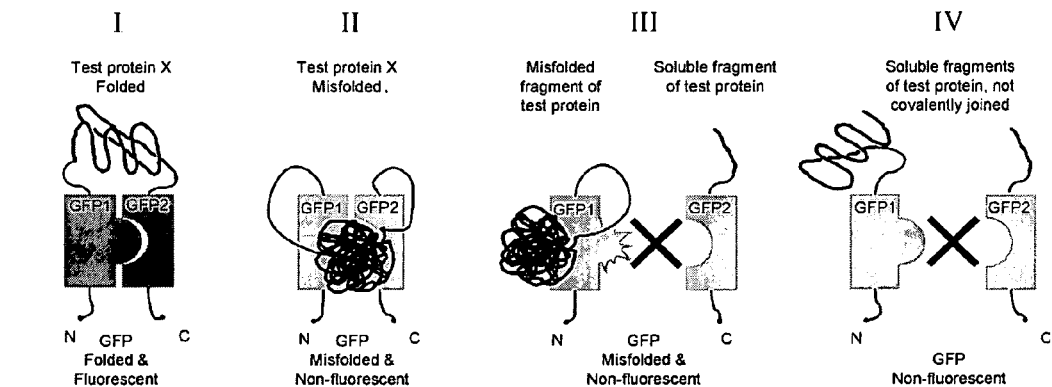

FIG. 10

| Rv# | Functional Assignment | MW kD | % sol | mg per liter |
|---|---|---|---|---|
| Rv0113 | phosphoheptose isomerase | 20.9 | 100 | 40 |
| Rv0237 | β-hexosaminidase A | 39.5 | 100 | 40 |
| Rv0341 | conserved hypothetical protein | 43.9 | 75 | 5 |
| Rv0429c | Polypeptide deformylase | 20.9 | 100 | N/A |
| Rv0557 | conserved hypothetical protein | 41.2 | 0 | 0 |
| Rv1008 | conserved hypothetical protein | 29.1 | 25 | N/A |
| Rv1202 | diaminopimelate desuccinylase | 37.2 | 75 | 15 |
| Rv1385 | orotidine 5'-phosphate decarboxylase | 27.3 | 0 | 0 |
| Rv1665 | polyketide synthase | 37.6 | 0 | 0 |
| Rv2148c | Conserved hypothetical protein | 27.7 | 60 | N/A |
| Rv2610c | Glycosyltransferase | 40.4 | 40 | 10 |
| Rv2895c | vibriobactin uptake | 30.6 | 100 | 15 |
| Rv2911 | penicillin binding protein | 29.8 | 100 | 40 |

FIG. 12

Internal sequence in wild type gene xylanase: TACTCCGTATTGAGTGTT<u>ATG</u>

Insert

| Vector | WT xylanase CGTA | Artifact I AGAA | Artifact II AATA | Artifact III AGTA |
|---|---|---|---|---|
| ΔRBS-X-FR GFP | | | | |
| X-FR GFP | | | | |
| GFPcp9/8_FR/FR | | | | |
| GFPcp9/8_SF/SF | | | | |
| GFPcp9/8_FR/SF | | | | |
| GFPcp9/8_FR/SF | | | | |

4 s Exposure      1 s Exposure

FIG. 13

| Insert | [a]Non-fusion solubility | [b][Trimethoprim] |
|---|---|---|
| Sulfite reductase (dissimilatory subunit) | 1.0 | 128 |
| Translation initiation factor | 1.0 | 128 |
| Chorismate mutase | 0.9 | 128 |
| c-type cytochrome biogenesis factor | 0.6 | 64 |
| Polysulfide reductase subunit | 0.0 | 16 |
| 3-hexulose 6-phosphate synthase | 0.5 | 128 |
| Methyl transferase | 0.0 | 16 |
| Blunt trapper frame shift stuffer CATATGTCAGGCCTTAACTAAGTAATAGGCCTCTGGATCC | | 0.25 |

FIG. 24
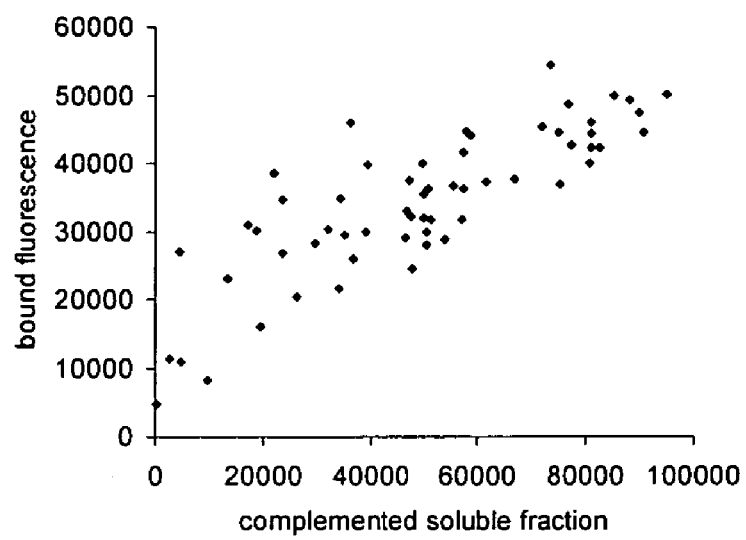
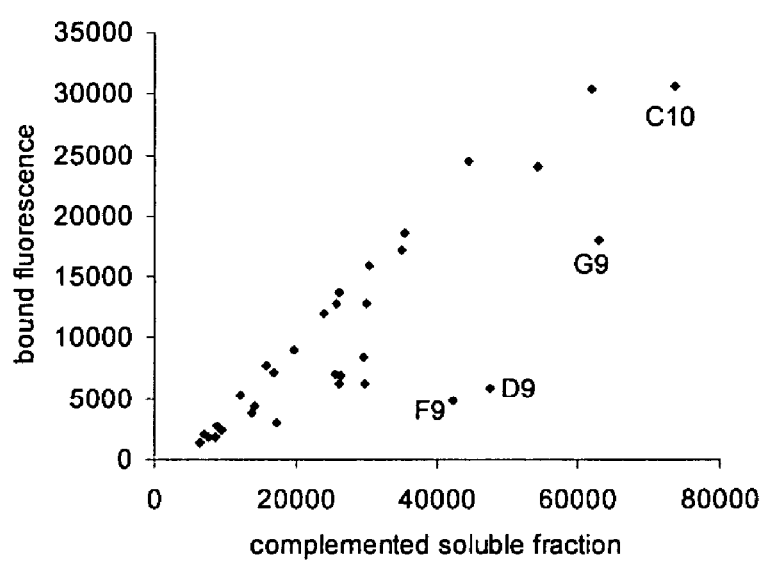

FIG. 27
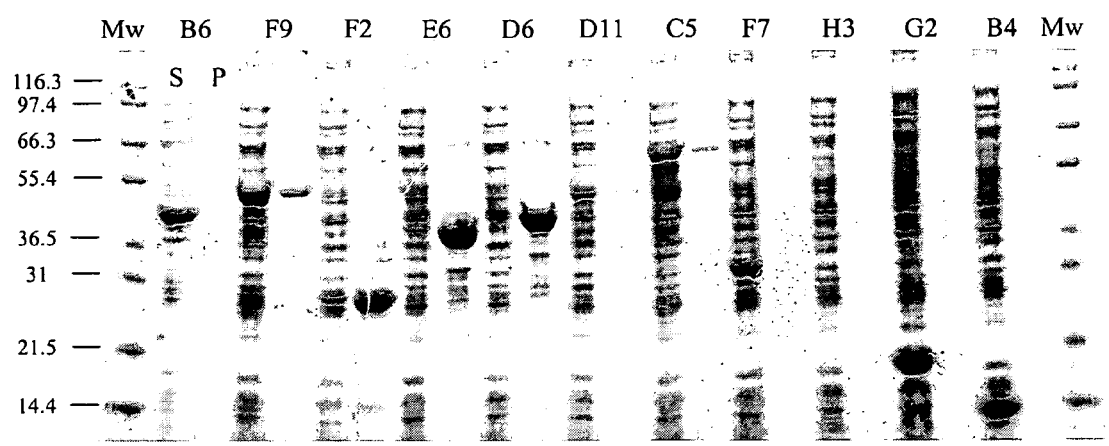
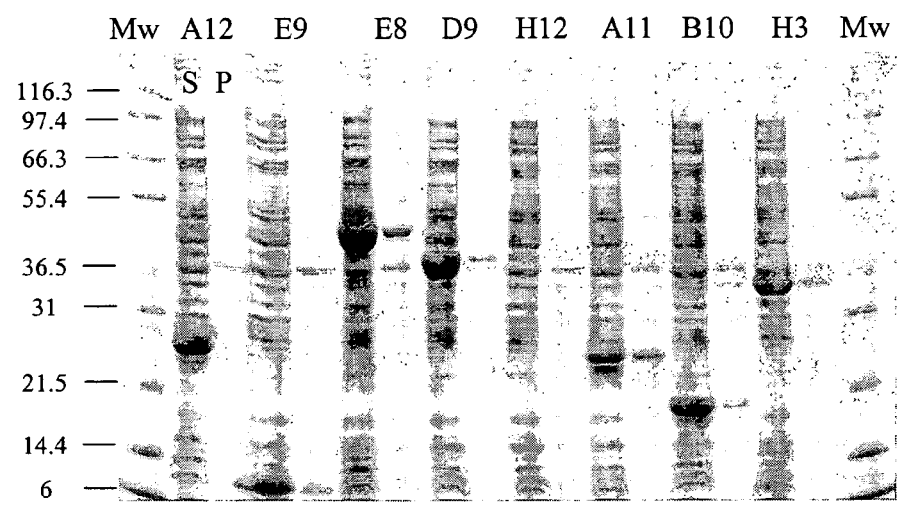

FIG. 28
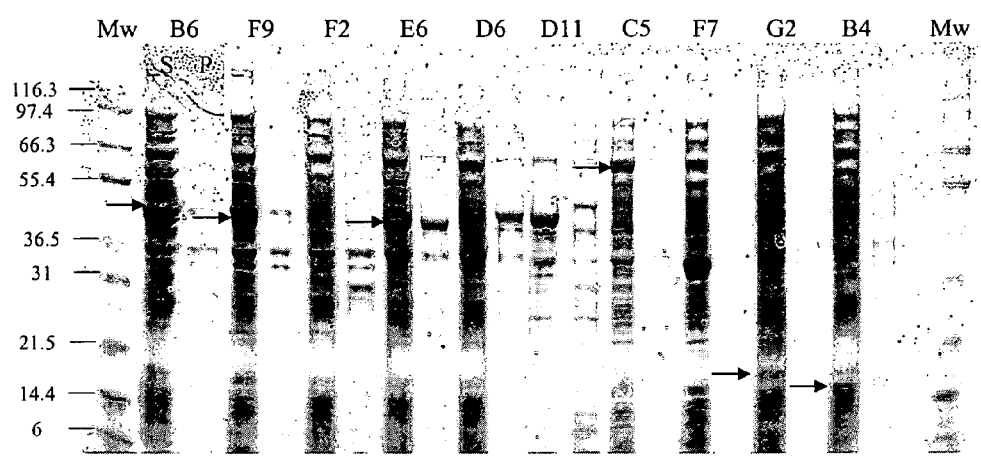
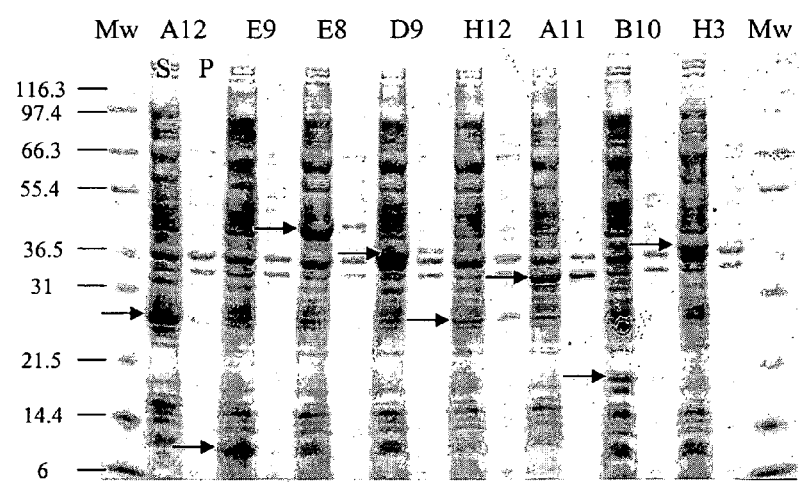

FIG. 29
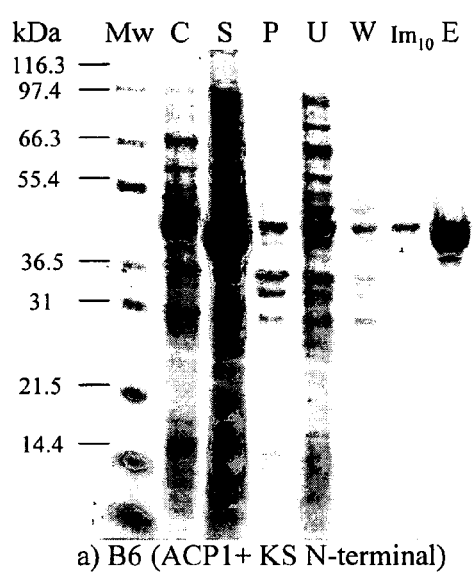
a) B6 (ACP1+ KS N-terminal)
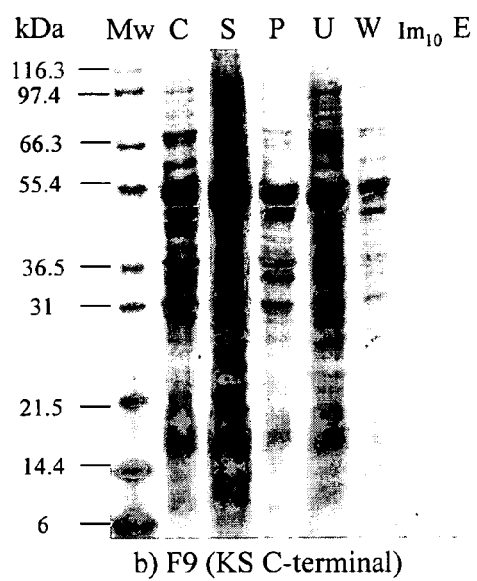
b) F9 (KS C-terminal)
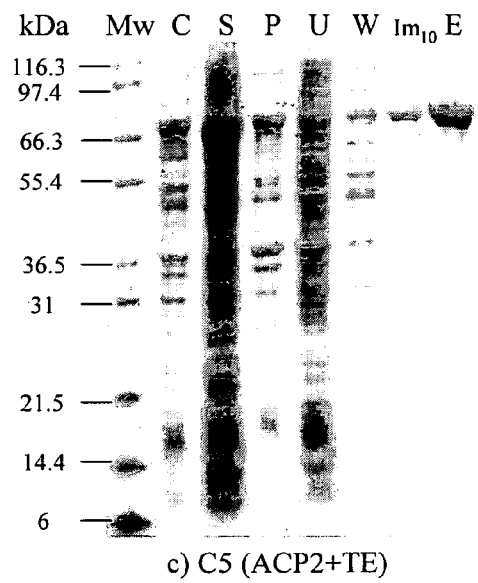
c) C5 (ACP2+TE)
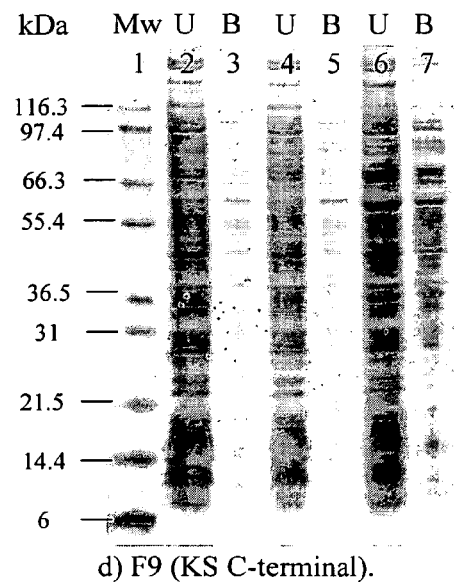
d) F9 (KS C-terminal).

CIRCULAR PERMUTANT GFP INSERTION FOLDING REPORTERS

RELATED APPLICATIONS

This application claims the benefit of U.S. Provisional Application Ser. No. 60/655,284 filed 22 Feb. 2005, and U.S. Provisional Application Ser. No. 60/699,269 filed 13 Jul. 2005.

STATEMENT AS TO RIGHTS TO INVENTIONS MADE UNDER FEDERALLY SPONSORED RESEARCH OR DEVELOPMENT

This invention was made with government support under grant number DE-FG02-98ER62647 from the United States Department of Energy and Contract No. W-7405-ENG-36 awarded by the United States Department of Energy to The Regents of The University of California. The government has certain rights in this invention.

BACKGROUND OF THE INVENTION

Obtaining sufficient amounts of soluble, well-folded recombinant proteins for downstream applications remains a significant bottleneck in many fields that apply protein expression technologies (Makrides 1996; Baneyx 1999; Fahnert, Lilie et al. 2004), including structural genomics projects (Yokoyama 2003; Goh, Lan et al. 2004; Terwilliger 2004). Current approaches for maximizing soluble protein include screening large numbers of protein variants (mutants, fragments, fusion tags, folding partners), and testing many expression or refolding conditions (Armstrong, de Lencastre et al. 1999; Fahnert, Lilie et al. 2004).

GFP and its numerous related fluorescent proteins are now in widespread use as protein tagging agents (for review, see Verkhusha et al., 2003, *GFP-like fluorescent proteins and chromoproteins of the class Anthozoa*. In: Protein Structures: Kaleidescope of Structural Properties and Functions, Ch. 18, pp. 405-439, Research Signpost, Kerala, India). In addition, GFP has been used as a solubility reporter of terminally fused test proteins (Waldo et al., 1999, *Nat. Biotechnol.* 17:691-695; U.S. Pat. No. 6,448,087, entitled 'Method for Determining and Modifying Protein/Peptide Solubility'; U.S. Pat. No. 6,448,087). GFP-like proteins are an expanding family of homologous, 25-30 kDa polypeptides sharing a conserved 11 beta-strand "barrel" structure. The GFP-like protein family currently comprises some 100 members, cloned from various *Anthozoa* and *Hydrozoa* species, and includes red, yellow and green fluorescent proteins and a variety of non-fluorescent chromoproteins (Verkhusha et al., supra). A wide variety of fluorescent protein labeling assays and kits are commercially available, encompassing a broad spectrum of GFP spectral variants and GFP-like fluorescent proteins, including DsRed and other red fluorescent proteins (Clontech, Palo Alto, Calif.; Amersham, Piscataway, N.J.).

SUMMARY OF THE INVENTION

The invention provides methods of assaying and improving protein folding using circular permutants of fluorescent proteins, including circular permutants of GFP variants and combinations thereof. The invention further provides various nucleic acid molecules and vectors incorporating such nucleic acid molecules, comprising polynucleotides encoding fluorescent protein circular permutants derived from superfolder GFP, which polynucleotieds include an internal cloning site into which a heterologous polynucleotide may be inserted in-frame with the circular permutant coding sequence, and which when expressed are capable of reporting on the degree to which a polypeptide encoded by an inserted heterologous polynucleotide is correctly folded by correlation with the degree of fluorescence exhibited.

In contrast to earlier described GFP folding reporter systems, in which a test protein is expressed as a C-terminal fusion with GFP in its native topology, the invention provides for test protein insertion within a circularly permuted fluorescent protein structure, specifically, between the native N- and C-termini of the fluorescent protein structure.

In the practice of the invention, test proteins are expressed as in-frame fusions within the circularly permuted fluorescent protein. The folding characteristics of the test protein translate to the folding of the GFP. For example, poorly folded test proteins will negatively influence the folding of the GFP molecule within which they are expressed, producing reduced or undetectable fluorescence levels. The brighter the cell in which the fusion is expressed, the better folded the test protein.

The invention also provides insertion GFP expression vectors used in the practice of the methods of the invention. In one embodiment, the insertion GFP expression vector encodes a circular permutant of a GFP variant, which contains a cloning site oriented between the native N- and C-termini for insertion of test proteins. Specific embodiments include circular permutants of folding reporter GFP and superfolder GFP, as well as chimeras thereof.

As further described in the Examples herein, exemplary sets of variably-stringent insertion GFP folding reporter vectors are also provided. These sets of insertion GFP folding reporters are particularly useful for the step-wise evolution of soluble variants of insoluble proteins. More specifically, these sets, when used in combination, provide a dynamic range of sensitivities to test protein misfolding. The vectors may be utilized, in seriatim, from the least to the most sensitive, in directed evolution approaches. Beginning with a low-stringency/low sensitivity insertion GFP folding reporter enables one to capture partially soluble variants that would read as insoluble using more stringent reporters. Such partially soluble variants provide the basis for generating further evolved variants. Thus, partially soluble and better folded variants are further evolved using increasingly stringent insertion GFP folding reporters in order to select for the best folded, most soluble variants at each level of stringency. At the end of the evolution strategy, the most stringent insertion GFP folding reporters enable selection of only the best folded variants, excluding even slightly misfolded versions.

In addition, the invention may be extended to other, non-fluorescent proteins. For example, an insertion DHFR folding reporter is exemplified herein. The insertion DHFR reporter also demonstrates the capacity to report on protein folding. Additionally, the insertion DHFR reporter provides a means for efficient open reading frame screening of inserted oplyppetides, proteins and domains, in view of the ability of over-expressed DHFR to confer resistance to the antibiotic trimethoprim in *E. coli*. Thus, out of frame inserted proteins (i.e., containing a stop codon) will not permit the expression of functional DHFR, and the cells in which the reporter fusion is expressed will not survive in media supplemented with the antibiotic. Colonies that survive will all have open reading frame inserts. This "ORF filter" may be used as a rapid initial screen in directed evolution approaches, followed by the use of a fluorescent protein reporter system, including without limitation the insertion GFP folding reporters of the invention and the split GFP reporter systems described in U.S. patent application Ser. No. 10/973,693, and in Cabantous et al., Nature Biotechnology January 2005.

A particular advantage of the insertion folding reporters of the invention is their ability to screen-out protein artifacts, such as those generated from internal ribosome binding sites introduced in directed evolution. C-terminal GFP folding reporters are unable to discriminate between artifact (i.e., a truncated protein) and a full length protein. Thus, the invention provides a more robust folding reporter system, inasmuch as it effectively eliminates the possibility of unwittingly selecting such artifacts.

The insertion GFP folding reporters described herein are particularly useful in directed evolution strategies aimed at improving the folding characteristics of poorly folded proteins, generating soluble variants of insoluble proteins, isolating or "trapping" soluble protein domains, and the like.

BRIEF DESCRIPTION OF THE DRAWINGS

FIG. 2 shows schematic representations of native and circular permutant GFP scaffolds. (A) Native topology of the 238 amino acid green fluorescent protein from *Aequorea victoria*. (B) Circular permutant starting at amino acid 173 and ending at 172, termed GFPcp9/8. (C) Circular permutant starting at 157 and ending at 156, termed GFPcp8/7. Nomenclature refers to beta strand numbers. GFPcp9/8 and GFPcp8/7 were the brightest circular permutants.

FIG. 3 shows the organization of GFP folding reporter constructs and their corresponding topologies. (A) GFPcp9/8 DNA cassette and corresponding reporter topology. (b) GFPcp8/7 DNA cassette and corresponding reporter topology. DNA and protein are shaded to show corresponding sections, light grey denotes the portion of the GFP scaffolding prior to the insert site and dark grey denotes the scaffolding after the insert site. The inserted test protein is attached to the GFP scaffolding via flexible amino acid linkers GGGSGGGS [SEQ ID NO: 25].

FIG. 4 shows schematic representations of GFPcp vectors with varying stringency to test protein X misfolding. The designations to the left of each cassette refer to the GFP scaffolding from which the fragments that bracket the test protein were obtained. FR=folding reporter GFP, SF=superfolder GFP. Thus FR/FR indicates that both GFP fragments came from folding reporter GFP, for example. The corresponding SF mutations indicated above constructs (A) GFPcp9/8 constructs and (B) GFPcp8/7 constructs (see EXAMPLE 1, infra.).

FIG. 6 describes the four main protein expression classes arising from fusion protein expression. The expected expression products derived from C-terminal or GFPcp insertion reporters are denoted for each class. (A) Conventional C-terminal reporters such as the C-terminal GFP can give a false-positive fluorescent signal if test protein is truncated (Class III and Class IV). (B) The circular permutant insertion folding reporter discriminates against Class III and Class IV because the inserted protein must be covalently tethered to both GFP fragments and not misfold in order to be fluorescent (Class I). Note that more than one Class of expression products can be produced simultaneously, such as Class II and Class III, where full-length insoluble protein and short soluble artifacts are expressed from the same construct due to additional internal ribosome binding site in addition to the usual vector-encoded ribosome binding site upstream of the gene in the cloning vector.

FIG. 10 is a table summarizing the results of directed evolution of insoluble M. tb. proteins using the GFPcp reporter(s) via process outlined in FIG. 8. Table shows the Rv designation for the gene in the M. tb genome, the classification of the protein, the predicted molecular weight in kilodaltons, the percentage expressed in the soluble fraction, and the total soluble protein expressed per liter of *E. coli* cell culture. Proteins are expressed without the fused GFP domain, and with N-terminal 6-histidine peptide tags.

FIG. 12 shows the ability of various GFP fusion reporters to discriminate against false positive signals from internal ribosome binding site artifacts in specific clones from the xylanase round three optima pool. Clones were bright expressing constructs with internal ribosome binding sites, as fusions with the C-terminal folding reporter, or as a fusion with the C-terminal folding reporter expressed from a vector without an upstream vector-encoded ribosome binding site. Note that the first column was imaged using a four second exposure while columns two to four were imaged using 1 second exposures, to compensate for very faint wild-type construct. Sequence of putative Shine Delgarno shown in bold above column for wild type and the three artifact clones. Artifact I appears bright in the least-stringent, best folded circular permutant insertion reporter (GFPcp9/8_SF/SF), likely due to the robust folding of the GFP variant.

FIG. 13 is a table showing the maximal concentration of trimethoprim at which *E. coli* expressing insertion DHFR fusion folding reporter with indicated *Pyrobaculum aerophilum* test insert proteins can survive. $^a$Non-fusion solubility of test insert expressed without the fused DHFR domains. $^b$Concentration of trimethoprim (μg/ml).

FIG. 24. Correlation between fluorescence of Talon resin-bound fraction and of complemented soluble fraction. On the left: analysis for library I and II. Right: analysis for library III. The clone number identifies outlined points.

FIG. 27. SDS-PAGE gel images corresponding to soluble (S) and insoluble (P) fractions obtained after expression of eighteen Pks13 domains subcloned into an N6HIS-pET vector. Clones were induced with 1 mM IPTG at 27° C. for 5 h.

FIG. 28. SDS-PAGE gel images corresponding to soluble (S) and insoluble (P) fractions obtained after expression of eighteen Pks13 domains subcloned into N6HIS-pTET vector. Clones were induced at 27° C. for 5 hours. Arrows indicate the overexpressed protein. Mass of molecular weight marker in kD (Mw).

FIG. 29. Talon resin purification of indicated selected domains subcloned in N6HIS pET vector. (a, b, c) The soluble fraction (S) of a 50 ml culture lysate (C: whole cells, S: soluble, P: pellet) was loaded on Talon beads. The unbound fraction (U) was removed by centrifugation. Talon beads were washed with loading buffer (W), and with loading buffer supplemented with imidazole ($Im_{10}$). Histidine tagged proteins were eluted (E) from the beads with 250 mM imidazole, TNG buffer. (d) Binding experiments for two additional constructs of F9 Ksc domain (B: bound fraction, U: unbound) for fragment F9 expressed from pET-C6HIS (lanes 2-5), and from GFP11 vector (lanes 6-7).

DETAILED DESCRIPTION OF THE INVENTION

Definitions

Figure 1:
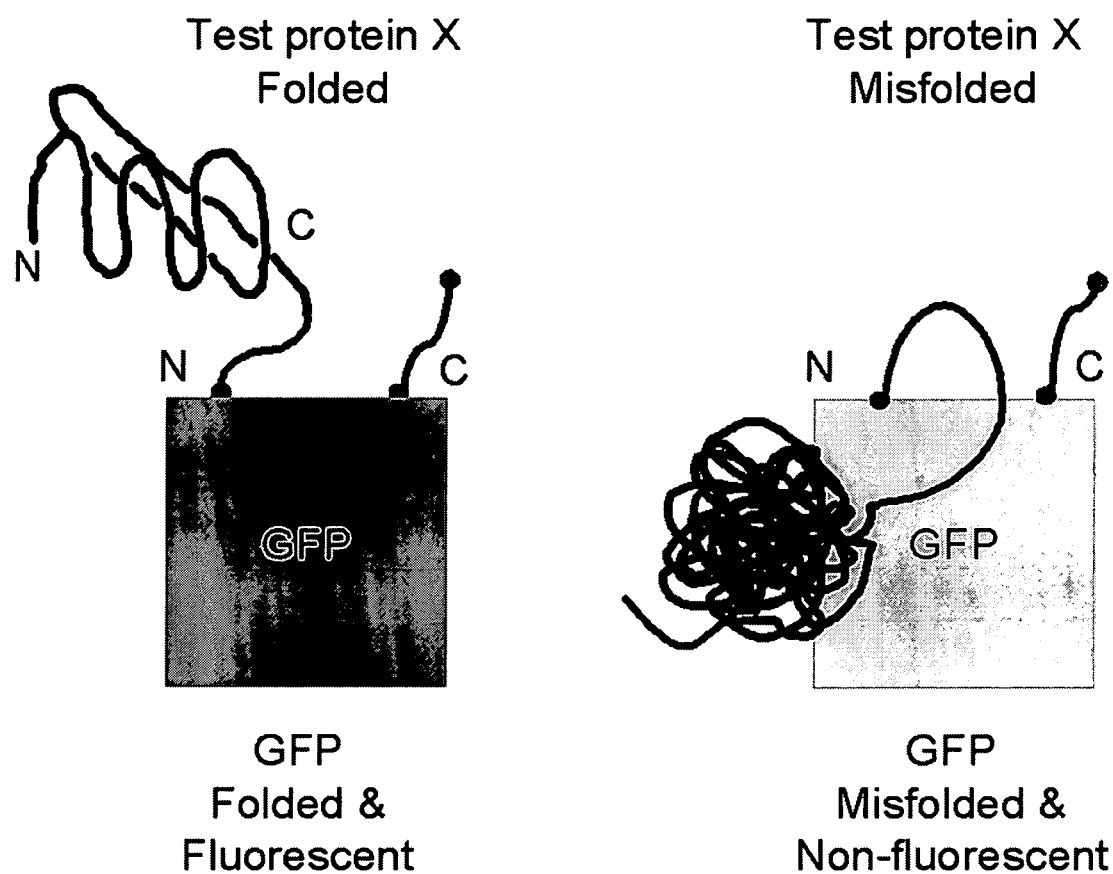
FIG. 1 shows schematic representations of various GFP folding reporter topologies. (left) A construct in which a test protein is expressed fused to the N-terminus of GFP. (right) A construct in which a test protein is expressed as a fusion inserted between two fragments of GFP.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

A "fluorescent protein" as used herein is an *Aequorea victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed). The term "GFP-like fluorescent protein" is used to refer to members of the *Anthozoa* fluorescent proteins sharing the 11-beta strand "barrel" structure of GFP, as well as structural, folding and spectral variants thereof. The terms "GFP-like non-fluorescent protein" and "GFP-like chromophoric protein" (or, simply, "chromophoric protein" or "chromoprotein") are used to refer to the *Anthozoa* and *Hydrozoa* chromophoric proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A "variant" of a fluorescent protein is derived from a "parent" fluorescent protein and retains the 11 beta-strand barrel structure as well as intrinsic fluorescence, and is meant to include structures with amino acid substitutions, deletions or insertions that may impart new or modified biological properties to the protein (i.e., greater stability, improved solubility, improved folding, shifts in emission or excitation spectra, reduced or eliminated capacity to form multimers, etc) as well as structures having modified N and C termini (i.e., circular permutants).

As used herein, the term "circular permutant" refers to recombinant fluorescent proteins which have been modified so that the native N- and C-termini are joined together, in frame, with or without an intervening spacer or linker sequence (also in-frame, typically including a cloning site for the introduction of heterologous polynucleotides in-frame with the sequence of the circular permutant fluorescent protein), and in which new N- and C-termini are created, by the introduction of a start codon in a polynucleotide encoding the circular permutant positioned within one of the loops joining two adjacent beta strand structural elements in the fluorescent protein, such that a new N-terminus is created. Additional cloning sites can be included at permissive sites, typically within one of the loops joining two adjacent beta strand structural elements in the fluorescent protein.

The "folding reporter GFP" (also "GFP$_{FR}$") is a GFP variant, described in U.S. patent application Ser. No. 10/423,688, which contains the amino acid mutations F99S, M153T, V163A (as described by Crameri et al., 1996) as well as F64L and S65T (as described by Patterson et al., 1997).

The "superfolder GFP" (also "GFP$_{SF}$") is a GFP variant described, inter alia, in U.S. patent application Ser. No. 10/423,688, which contains all of the folding reporter GFP mutations as well as the additional mutations S30R, Y39N, N105T, Y145F, I171V, and A206V. The amino acid sequence of superfolder GFP is also provided in the TABLE OF SEQUENCES listing, infra.

As used herein, the term "cloning site" refers to a DNA sequence containing a restriction site for restriction endonuclease-mediated cloning by ligation of a DNA sequence containing compatible cohesive or blunt ends, a region of DNA sequence serving as a priming site for PCR-mediated cloning of insert DNA by homology and extension "overlap PCR stitching", or a recombination site for recombinase-mediated insertion of target DNA sequences by recombination-exchange reaction, or mosaic ends for transposon mediated insertion of target DNA sequences, as well as other techniques common in the art.

The term "complementing fragments" or "complementary fragments" when used in reference to a reporter polypeptide refer to fragments of a polypeptide that are individually inactive (i.e., do not express the reporter phenotype), wherein binding of the complementing fragments restores reporter activity. The terms "self-complementing", "self-assembling", and "spontaneously-associating", when used to describe two or more fluorescent (or chromophoric) protein fragments, mean that the fragments are capable of reconstituting into an intact, fluorescent (or chromophoric) protein when the individual fragments are soluble.

The "MMDB Id: 5742 structure" as used herein refers to the GFP structure disclosed by Ormo & Remington, MMDB Id: 5742, in the Molecular Modeling Database (MMDB), PDB Id: 1EMA PDB Authors: M. Ormo & S. J. Remington PDB Deposition: 1 Aug. 1996 PDB Class: Fluorescent Protein PDB Title: Green Fluorescent Protein From *Aequorea Victoria*. The Protein Data Bank (PDB) reference is Id PDB Id: 1EMA PDB Authors: M. Ormo & S. J. Remington PDB Deposition: 1 Aug. 1996 PDB Class: Fluorescent Protein PDB Title: Green Fluorescent Protein From *Aequorea Victoria*. (see, e.g., Ormo et al. "Crystal structure of the *Aequorea victoria* green fluorescent protein." *Science* 1996 Sep. 6; 273 (5280):1392-5; Yang et al, "The molecular structure of green fluorescent protein." *Nat Biotechnol.* 1996 Oct. 14(10):1246-51).

"Root mean square deviation" ("RMSD") refers to the root mean square superposition residual in Angstroms. This number is calculated after optimal superposition of two structures, as the square root of the mean square distances between equivalent C-alpha-atoms.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, $M=5$, $N=-4$ and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as a fluorescent binding ligand and a display protein or nucleic acid, and serves to place the two molecules in a preferred configuration.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "isolated" and "purified" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

Circular Permutation of Fluorescent Proteins

One aspect of the invention relates to insertional folding reporters constructed from circular permutants of fluorescent proteins, such as GFP and variants thereof. Although the invention is exemplified by the use of GFP variants, GFP-like fluorescent proteins may also be employed. Methods of generating superfolder versions of GFP-like proteins are provided in U.S. application Ser. No. 10/423,688, filed Apr. 24, 2003. Superfolder versions of GFP-like fluorescent proteins may be generated and evaluated for folding characteristics in each of the possible circular permutant topologies, and tested for tolerance to inserted test proteins, as described therein and in Examples 1-3, infra.

Generally, circular permutant topologies which fold well without any inserted guest protein or polypeptide (in a the particular expression environment in which the corresponding folding reporters are to be used) are suitable for generating insertional folding reporters. Topologies which misfold without inserts may produce folding reporters that show dim fluorescence even with inserted, well-folded proteins.

As will be understood by those skilled in the art, the generation of circular permutants of GFP-like proteins may be modeled on the GFP circular permutants described herein (see Example 1). Since GFP and GFP-like proteins share a conserved 11 beta-strand barrel structure, 11 possible circular permutant topologies are possible, wherein new N- and C-termini are introduced within the turns between secondary structure elements and the native N- and C-termini are joined, typically via a short linker polypeptide. The generation of circular permutants of GFP variants may be accomplished using primer-based PCR (and similar methodologies) as described in the Examples herein as well as in U.S. patent application Ser. No. 10/973,693.

Polynucleotides encoding circular permutants of GFP, GFP variants, GFP-like proteins and even non-fluorescent GFP-like proteins may be generated, cloned into any suitable expression vector (i.e., pET, pQE, T7 promoter vectors, etc.), expressed constitutively or transiently in an appropriate host cell (i.e., E. coli) and evaluated for folding and solubility characteristics by measuring fluorescence intensity (or color intensity in the case of chromophoric non-fluorescent GFP-like proteins).

Wild type GFP normally misfolds and is poorly fluorescent when overexpressed in the heterologous host E. coli, and is found predominantly in the inclusion body fraction of cell lysates. The misfolding is incompletely understood, but is thought to result from the increased expression level or rate in E. coli, or the inadequacy of the bacterial chaperone and related folding machinery under conditions of overexpression. The folding yield also decreases dramatically at higher temperatures (37° C. vs. 27° C.). This wild type GFP is a very poor folder, as it is extremely sensitive to the expression environment. Therefore, in preferred embodiments, GFP variants having improved folding and solubility characteristics are employed. In one embodiment, the GFP "superfolder" variant (U.S. Ser. No. 10/973,693) is used to construct circular permutants and insertion GFP folding reporters therefrom. In another embodiment, "folding reporter" GFP is used (see Examples, infra). In other embodiments, domains from different GFPs or different circular permutants may be combined (for example, see FIGS. 4A and 4B).

Fluorescent Proteins

A large number of fluorescent proteins related to GFP have now been described. Any of these may be used to generate insertion folding reporters. One group of fluorescent proteins includes the Green Fluorescent Protein isolated from *Aequorea victoria* (GFP), as well as a number of GFP variants, such as cyan fluorescent protein, blue fluorescent protein, yellow fluorescent protein, etc. (Zimmer, 2002, Chem. Rev. 102: 759-781; Zhang et al., 2002, Nature Reviews 3: 906-918). Typically, these variants share about 80%, or greater sequence identity with SEQ ID NO:2 (or SEQ ID NO:8.) These color-shift GFP mutants have emission colors blue to yellow-green, increased brightness, and photostability (Tsien, 1998, Annual Review of Biochemistry 67: 509-544). One such GFP mutant, termed the Enhanced Yellow Fluorescent Protein, displays an emission maximum at 529 nm. Another recently described mutant, a gold variant, was generated by incorporating a non-natural variant of tryptophan into the cyan variant, and is characterized by a significantly red-shifted emission maximum of 574 nm (Bae et al., 2003, J. Mol. Biol. 328:1071-1081).

Additional GFP-based variants having modified excitation and emission spectra (Tsien et al., U.S. Patent Appn. 20020123113A1), enhanced fluorescence intensity and thermal tolerance (Thastrup et al., U.S. Patent Appn. 20020107362A1; Bjorn et al., U.S. Patent Appn. 20020177189A1), and chromophore formation under reduced oxygen levels (Fisher, U.S. Pat. No. 6,414,119) have also been described. GFPs from the Anthozoans *Renilla reniformis* and *Renilla kollikeri* have also been described (Ward et al., U.S. Patent Appn. 20030013849).

Additionally, over 100 GFP-like fluorescent proteins and non-fluorescent chromoproteins from the class *Anthozoa* have now been identified (for review, see Verkusha et al., 2003, GFP-like fluorescent proteins and chromoproteins of the class *Anthozoa*, In: Protein Structures: Kaleidoscope of Structural Properties and Functions, pp. 405-439, Ed. V. Uversky. Research Signpost Press, Kereala, India). This group of *Anthozoa* proteins includes the red fluorescent protein isolated from *Discosoma* species of coral, DsRed (Matz et al., 1999, Nat. Biotechnol. 17:969-973), and various DsRed variants (e.g., DsRed1, DsRed2). DsRed and the other *Anthozoa* fluorescent proteins share only about 26-30% amino acid sequence identity to the wild-type GFP from *Aequorea victoria*, yet all the crucial motifs are conserved, indicating the formation of the 11-stranded beta-barrel structure characteristic of GFP. The crystal structure of DsRed has also been solved, and shows conservation of the 11-stranded beta-barrel structure of GFP MMDB Id: 5742.

A number of mutants of the longer wavelength red fluorescent protein DsRed have also been described. For example, recently described DsRed mutants with emission spectra shifted further to the red may be employed in the practice of the invention (Wiehler et al., 2001, FEBS Letters 487: 384-389; Terskikh et al., 2000, Science 290: 1585-1588; Baird et al., 2000, Proc. Natl. Acad. Sci. USA 97: 11984-11989). Recently, a monomeric variant of DsRed was described (Campell et al., 2002, Proc. Natl. Acad. Sci USA 99: 7877-7882). This variant, termed "mRFP1", matures quickly (in comparison to wild type DsRed, which matures over a period of 30 hours), has no residual green fluorescence, and has excitation and emission wavelengths of about 25 nm longer than other DsRed variants.

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with structures inferred to be similar to GFP from corals, sea pens, sea squirts, and sea anemones have been described, and may be used in the generation of the insertional folding reporters of the invention (for reviews, see Zimmer, 2002, Chem. Rev. 102: 759-781; Zhang et al., 2002, Nature Reviews 3: 906-918).

Additionally, fluorescent proteins from *Anemonia majano*, *Zoanthus* sp., *Discosoma striata*, *Discosoma* sp. and *Clavularia* sp. have also been reported (Matz et al., supra). A fluorescent protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656). Recently described fluorescent proteins from sea anemones include green and orange fluorescent proteins cloned from *Anemonia sulcata* (Wiedenmann et al., 2000, Proc. Natl. Acad. Sci. USA 97: 14091-14096), a naturally enhanced green fluorescent protein cloned from the tentacles of *Heteractis magnifica* (Hongbin et al., 2003, Biochem. Biophys. Res. Commun. 301: 879-885), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882).

A recently described red fluorescent protein isolated from the sea anenome *Entacmaea quadricolor*, EqFP611, is a far-red, highly fluorescent protein with a unique co-planar and trans chromophore (Wiedenmann et al., 2002, Proc. Natl. Acad. Sci USA 99: 11646-11651). The crystal structure of EqFP611 has been solved, and shows conservation of the 11-stranded beta-barrel structure of GFP MMDB Id: 5742 (Petersen et al., 2003, J. Biol. Chem, Aug. 8, 2003; M307896200).

Still further classes of GFP-like proteins having chromophoric and fluorescent properties have been described. One such group of coral-derived proteins, the pocilloporins, exhibit a broad range of spectral and fluorescent characteristics (Dove and Hoegh-Guldberg, 1999, PCT application WO 00/46233; Dove et al., 2001, Coral Reefs 19: 197-204). Recently, the purification and crystallization of the pocilloporin Rtms5 from the reef-building coral *Montipora efflorescens* has been described (Beddoe et al., 2003, Acta Cryst. D59: 597-599). Rtms5 is deep blue in color, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003, supra; Bulina et al., 2002, BMC Biochem. 3: 7; Lukyanov et al., 2000, supra). Various other coral-derived chromoproteins closely related to the pocilloporins are also known (see, for example, Lukyanov et al. 2000, J. Biol. Chem. 275: 25879-82; Gurskaya et al., 2001, FEBS Letters 507: 16-20).

Any fluorescent protein that has a structure with a root mean square deviation of less than 5 angstroms, often less than 3, or 4 angstroms, and preferably less than 2 angstroms from the 11-stranded beta-barrel structure of MMDB Id:5742 may be used in the development of insertion fluorescent protein folding reporters. In some cases, fluorescent proteins exist in multimeric form. For example, DsRed is tetrameric (Cotlet et al., 2001, Proc. Natl. Acad. Sci. USA 98: 14398014403). As will be appreciated by those skilled in the art, structural deviation between such multimeric fluorescent proteins and GFP (a monomer) is evaluated on the basis of the monomeric unit of the structure of the fluorescent protein.

As appreciated by one of ordinary skill in the art, such a suitable fluorescent protein or chromoprotein structure can be identified using comparison methodology well known in the art. In identifying the protein, a crucial feature in the alignment and comparison to the MMDB ID:5742 structure is the conservation of the beta-barrel structure (i.e., typically comprising 11 beta strands, but in at least one case, fewer beta strands (see, Wiedenmann et al., 2000, supra), and the topology or connection order of the secondary structural elements (see, e.g., Ormo et al. "Crystal structure of the *Aequorea victoria* green fluorescent protein."Yang et al, 1996, Science 273: 5280, 1392-5; Yang et al., 1996 Nat Biotechnol. 10:1246-51). Typically, most of the deviations between a fluorescent protein and the GFP structure are in the length(s) of the connecting strands or linkers between the crucial beta strands (see, for example, the comparison of DsRed and GFP in Yarbrough et al., 2001, Proc Natl Acad Sci USA 98:462-7). In Yarbrough et al., alignment of GFP and DsRed is shown pictorially. From the stereo diagram, it is apparent that the 11 beta-strand barrel is rigorously conserved between the two structures. The c-alpha backbones are aligned to within 1 angstrom RMSD over 169 amino acids, although the sequence identity is only 23% comparing DsRed and GFP.

In comparing structure, the two structures to be compared are aligned using algorithms familiar to those in the art, using for example the CCP4 program suite. COLLABORATIVE COMPUTATIONAL PROJECT, NUMBER 4. 1994. "The CCP4 Suite: Programs for Protein Crystallography". Acta Cryst. D50, 760-763. In using such a program, the user inputs the PDB coordinate files of the two structures to be aligned, and the program generates output coordinates of the atoms of the aligned structures using a rigid body transformation (rotation and translation) to minimize the global differences in position of the atoms in the two structures. The output aligned coordinates for each structure can be visualized separately or as a superposition by readily-available molecular graphics programs such as RASMOL, Sayle and Milner-White, September 1995, Trends in Biochemical Science (TIBS), Vol. 20, No. 9, p. 374.), or Swiss PDB Viewer, Guex, N and Peitsch, M. C., 1996 Swiss-PdbViewer: A Fast and Easy-to-use PDB Viewer for Macintosh and PC. Protein Data Bank Quarterly Newsletter 77, pp. 7.

In considering the RMSD, the RMSD value scales with the extent of the structural alignments and this size is taken into consideration when using the RMSD as a descriptor of overall structural similarity. The issue of scaling of RMSD is typically dealt with by including blocks of amino acids that are aligned within a certain threshold. The longer the unbroken block of aligned sequence that satisfies a specified criterion, the 'better' aligned the structures are. In the DsRed example, 164 of the c-alpha carbons can be aligned to within 1 angstrom of the GFP. Typically, users skilled in the art will select a program that can align the two trial structures based on rigid body transformations, for example, as described in Dali et al., Journal of Molecular Biology 1993, 233, 123-138. The output of the DALI algorithm are blocks of sequence that can be superimposed between two structures using rigid body transformations. Regions with Z-scores at or above a threshold of $Z=2$ are reported as similar. For each such block, the overall RMSD is reported.

The RMSD of a fluorescent protein or chromoprotein for use in the invention is within 5 angstroms for at least 80% of the sequence within the 11 beta strands. Preferably, RMSD is within 2 angstroms for at least 90% of the sequence within the 11 beta strands (the beta strands determined by visual inspection of the two aligned structures graphically drawn as superpositions, and comparison with the aligned blocks reported by DALI program output). As appreciated by one of skill in the art, the linkers between the beta strands can vary considerably, and need not be superimposable between structures.

In preferred embodiments, the fluorescent protein or chromoprotein is a mutated version of the protein or a variant of the protein that has improved folding properties or solubility in comparison to the protein. Often, such proteins can be identified, for example, using methods described in WO0123602 and other methods to select for increased folding.

For example, to obtain a fluorescent protein with increased folding properties, a "bait" or "guest" peptide that decreases the folding yield of the fluorescent protein is linked to the fluorescent protein. The guest peptide can be any peptide that, when inserted, decreases the folding yield of the fluorescent protein. A library of mutated fluorescent proteins is created. The bait peptide is inserted into the fluorescent protein and the degree of fluorescence of the protein is assayed. Those clones exhibit increased fluorescence relative to a fusion protein comprising the bait peptide and parent fluorescent protein are selected (the fluorescent intensity reflects the amount of properly folded fluorescent protein). The guest peptide may be linked to the fluorescent protein at an end, or may be inserted at an internal site.

In a particular embodiment, wild-type and mutant fluorescent proteins and chromoproteins useful in the practice of the invention may be experimentally "evolved" to produce extremely stable, "superfolding" variants. The methods described in co-pending, co-owned U.S. patent application Ser. No. 10/423,688, filed Apr. 24, 2003, hereby incorporated by reference in its entirety, may be employed for the directed evolution of GFP, DsRed, and any number of related fluorescent proteins and chromoproteins. Such superfolding variants may be preferred because of their expected increased tolerance to circular permutation.

Use of DHFR and Other Reporter Proteins

The concept of the invention may be extend to other proteins capable of displaying a detectable phenotype. In one exemplified embodiment, an insertional DHFR folding reporter construct was generated. The folding characteristics of inserted proteins and polypeptides transduce to the folding of the DHFR-inserted protein fusion (see Examples 6-9, infra).

The insertion DHFR reporter is also particularly useful as an open reading frame screen, enabling rapid elimination of out of frame inserts from large random libraries. In view of the ability of over-expressed DHFR to confer resistance to the antibiotic trimethoprim in E. coli, out of frame inserts will result in the expression of out of frame DHFR, and the cells in which the fusion is expressed will not survive in media supplemented with trimetheprim. Colonies that survive will all have open reading frame inserts. This "ORF filter" may be used as a rapid initial screen in directed evolution approaches, followed by the use of a fluorescent protein reporter system, including without limitation the insertion GFP folding reporters of the invention and the split GFP reporter systems described in U.S. patent application Ser. No. 10/973,693, and in Cabantous et al., Nature Biotechnology January 2005.

Other proteins which may be used in a similar way include, for example, chloramphenicol, acetyl transferase, and beta-lactamase.

Nucleic Acid and Expression Vector Constructs

The invention also provides polynucleotides encoding circular permutants of GFP variants and GFP-like proteins, expressible cassettes encoding circular permutants into which cloning sites (and test proteins, fragments and domains) have been introduced, and expression vectors containing such cassettes, as well as host cells into which such expression vectors have been introduced.

In the practice of the invention, test proteins are expressed as in-frame fusions within circularly permuted fluorescent proteins, such as GFP circular permutants. This accomplished by introducing polynucleotides encoding the test protein (or fragment or domain) into the insertion site of a polynucleotide encoding the circular permutant. This construct is either part of or is cloned into an expression vector capable of directing the expression of the resulting fusion protein in a given host cell. For fluorescent proteins such as GFP, E. coli is generally an appropriate host cell. However, GFP and GFP-like proteins may be expressed in any type of host cell, both eukaryotic and prokaryotic, using a wide variety of expression vectors, promoters, etc., as is generally known in the art. In one embodiment, insertional fluorescent protein folding reporter vectors may be based on a pET vector (see Examples infra).

The precise construction of the cassette encoding the insertional folding reporter may vary according to the particular fluorescent protein(s), restriction sites, linkers, and the like used in the construction, as will be appreciated by those skilled in the art. In the construction of circular permutants, the native N- and C-termini coding sequences of the fluorescent protein may be joined directly or via a polypeptide linker or linkers. In the embodiments exemplified herein, polynucleotides encoding short conformationally flexible polypeptide linkers comprising amino acids without bulky side-chains (i.e., GGGSGGGS) are used to join the two native termini. The introduction of a cloning site within this junction is a preferred method of providing an insertion point for test coding sequences. In one embodiment, two linkers are used to flank the insertion site (see Examples herein).

Generation of Variably-Stringent Reporters

The insertional folding reporter concept of the invention lends itself to the generation and application of variably-stringent reporters having different levels of sensitivity to inserted protein/polypeptide misfolding. Reporter stringency may be controlled using a number of techniques, including without limitation the use different fluorescent proteins or variants thereof for the construction of the circular permutants, the use of combined domains from circular permutants having different levels of stringency, the gross topology of the circular permutant, and expression temperature. As illustrated in Examples 2 and 3 herein, sets of insertion GFP reporters were generated, each more or less stringent than the next, thus creating a dynamic range of stringency useful in connection with protein evolution methodologies. This was accomplished by using circular permutants from two different GFP variants, each having different sensitivities to inserted protein misfolding, and by combining domains from each to form intermediate stringency versions.

The relative location of the inserted protein or polypeptide within the circular permutant fluorescent protein also may influence stringency. In particular, with reference to circular permutants of GFP variants (see Example 1), the closer the insertion point is to the new N-terminus, and the farther away it is from the C-terminus, the more stringent the reporter. A likely explanation for this is that misfolded proteins that are expressed closer to the N-terminus have a greater influence on the folding of the larger C-terminal part of the circular permutant. In other words, the longer the sequence downstream of the insert, the more chance for folding interference by a misfolded inserted protein.

In addition, the temperature at which the insertional folding reporter-inserted test protein fusion is expressed may influence stringency. In this regard, it has been observed that insertional GFP folding reporters appear to be more stringent when used at higher expression temperatures (i.e., 37° C. vs. 27° C.; see FIG. 9 and Example 4).

Such sets of variably-stringent folding reporter vectors may be utilized, in seriatim, from the least to most sensitive vectors in directed evolution approaches. Beginning with a low-stringency/low sensitivity insertion GFP folding reporter enables one to capture partially soluble variants that would read as insoluble using more stringent reporters. Such partially soluble variants provide the basis for generating further evolved variants. Thus, partially soluble and better folded variants are further evolved using increasingly stringent insertion GFP folding reporters in order to select for the best folded, most soluble variants at each level of stringency. At the end of the evolution strategy, the most stringent insertion GFP folding reporters enable selection of only the best folded variants, excluding even slightly misfolded versions.

Folding Reporter Assays

The use of the insertional folding reporters of the invention is straightforward. A polynucleotide encoding the test polypeptide, protein, protein fragment, domain, etc., is cloned into the insertion vector (i.e., GFPcp9/8_FR/FR; see Examples and FIG. 4) and the fusion protein encoded thereby is expressed in a suitable host cell. Where the insertional folding reporter is based on a GFP or variant thereof, or a GFP-like fluorescent protein, folding of the test protein (or fragment, domain, etc.) correlates with the folding of the GFP or fluorescent protein, which can be directly observed and/or quantified by measuring fluorescence from the cell(s). Well folded proteins, fragments or domains will not disrupt productive folding of the fluorescent protein, and therefore the expressed fusion displays the fluorescent phenotype. Poorly folded proteins, on the other hand, will disrupt folding, resulting in a fusion that will not display a fluorescent phenotype. Partially or incompletely folded proteins may have a slight or moderate interference on the folding of the fluorescent protein (and the fusion), which may be observed as a diminished (but not undetectable) level of fluorescence relative to the reporter protein expressed without the inserted protein.

The insertional folding reporters of the invention may be applied to assays for protein folding, soluble domain trapping and in the context of directed evolution of better-folded and more soluble variants of misfolded proteins/polypeptides. In one embodiment, the insertion GFP reporters described herein are used to screen for soluble proteins, domains, or fragments. Screening may be conducted on a high-throughput basis, for example, to screen a library of proteins, protein domains, or random protein fragment libraries. See infra.

Methods for Isolating Folding and Solubility Enhanced Variants

The insertional folding reporters of the invention may be used in connection with the generation of evolved mutants of poorly folded proteins. A number of directed evolution strategies may be used in combination with screening for folding using single-stringency insertional folding reporters or various combinations of variably-stringent folding reporters. An initial screen for ORF inserts may employed, such as the DHFR ORF filter described herein. These approaches are readily adapted to high-throughput methodologies.

Any method known in the art for generating a library of mutated protein or polypeptide variants may be used to generate candidate test proteins which may be expressed as fusions within the insertional folding reporter. The target protein or polypeptide is usually mutated by mutating the nucleic acid, using various techniques well known in the art, inclusing without limitation, error-prone PCR, chemical mutagenesis, and cassette mutagenesis. Alternatively, matador strains of host cells may be employed to add mutational frequency (Greener and Callahan (1995) *Strategies in Mol. Biol.* 7: 32). For example, error-prone PCR (see, e.g., Amusable, supra) uses low-fidelity polymerization conditions to introduce a low level of point mutations randomly over a long sequence.

Other mutagenesis methods include, for example, recombination (WO98/42727); oligonucleotide-directed mutagenesis (see, e.g., the review in Smith, *Ann. Rev. Genet.* 19: 423-462 (1985); Botstein and Shortle, *Science* 229: 1193-1201 (1985); Carter, *Biochem. J.* 237: 1-7 (1986); Kunkel, "The efficiency of oligonucleotide directed mutagenesis" in Nucleic acids & Molecular Biology, Eckstein and Lilley, eds., Springer Verlag, Berlin (1987), *Methods in Enzymol.* 100: 468-500 (1983), and *Methods in Enzymol.* 154: 329-350 (1987)); phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16:791-802 (1988); Sayers et al., *Nucl. Acids Res.* 16: 803-814 (1988)), mutagenesis using uracil-containing templates (Kunkel, *Proc. Nat'l. Acad. Sci. USA* 82: 488-492 (1985) and Kunkel et al., Methods in Enzymol. 154:367-382, 1987); mutagenesis using gapped duplex DNA (Kramer et al., *Nucl. Acids Res.* 12: 9441-9456 (1984); Kramer and Fritz, *Methods in Enzymol.* 154:350-367 (1987); Kramer et al., *Nucl. Acids Res.* 16: 7207 (1988)); and Fritz et al., *Nucl. Acids Res.* 16: 6987-6999 (1988)). Additional methods include point mismatch repair (Kramer et al., *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415-423 (1986)), mutagenesis by total gene synthesis (Nambiar et al., Science 223: 1299-1301 (1984); Sakamar and Khorana, *Nucl. Acids Res.* 14: 6361-6372 (1988); Wells et al., *Gene* 34:315-323 (1985); and Grundstrom et al., *Nucl. Acids Res.* 13: 3305-3316 (1985). Kits for mutagenesis are commercially available (e.g., Bio-Rad, Amersham International). More recent approaches include codon-based mutagenesis, in which entire codons are replaced, thereby increasing the diversity of mutants generated, as exemplified by the RID method described in Murakami et al., 2002, Nature Biotechnology, 20: 76-81.

Soluble Domain Trapping

The insertional folding reporters of the invention are particularly useful for isolating, or "trapping", soluble domains of proteins that are recalcitrant to expression in soluble form. Indeed, the structural resolution of a number of large and/or poorly folded proteins has been severely limited by misfolding and insolubility problems. Various methods are currently used in attempts to identify soluble domains of such proteins, including for example, limited proteolysis and bioinformatics/predictive algorithms. However, these methods are extremely time consuming and problematic. The invention's insertional folding reporter system enables a far more efficient and effective methodology for identifying soluble domains. Briefly, the invention's method of soluble domain trapping involves the creation of a large DNA fragment library from the coding sequence or gene or the protein of interest. This may be accomplished, for example, by partially digesting the DNA with DNase, mechanically shearing the DNA, or by using recombination techniques. The resulting DNA fragments are cloned into the insertional folding reporter vector, and the "fragment" library is expressed. Detectable fluorescence correlates with the expression of folded or partially-folded domain polypeptides. This method is illustrated in Example 10, wherein fragments of DNA encoding Nod2, a normally insoluble human protein when expressed in *E. coli*, were cloned into the insertion GFP vectors, resulting in the isolation of 12 soluble domains in a matter of days (see FIG. 15). Optionally, an ORF filter such as the DHFR ORF filter described, infra, is used to provide an initial screen for clones containing open reading frame inserts (as was done in the case of the Nod2 protein).

Kits

Another aspect of the invention provides insertional folding reporter kits useful in conducting the various assays and methods described, supra. Kits of the invention may facilitate the use of insertional folding reporters of the invention. Various materials and reagents for practicing the assays of the invention may be provided. Kits may contain reagents including, without limitation, expression vectors, cell transformation or transfection reagents, as well as other solutions or buffers useful in carrying out the assays and other methods of the invention. Kits may also include control samples, materials useful in calibrating the assays of the invention, and containers, tubes, microtiter plates and the like in which assay reactions may be conducted. Kits may be packaged in containers, which may comprise compartments for receiving the contents of the kits, instructions for conducting the assays, etc.

For example, kits may provide one or more polynucleotides, vectors and/or expression vectors of the invention, cell strains suitable for propagating the vector and/or expressing fusion proteins using the polynucleotides of the invention, cells pre-transformed or stably transfected with such vectors, and associated reagents for use in employing the methods of the invention.

EXAMPLES

Various aspects of the invention are further described and illustrated by way of the several examples which follow, none of which are intended to limit the scope of the invention.

Example 1

Generation of GFP Circular Permutants—Selection of Suitable Topologies

Circular permutants of superfolder GFP and folding reporter GFP variants were generated for each of eleven possible topologies, expressed in *E. coli*, and evaluated for folding/fluorescence as described (U.S. patent applications Ser. Nos. 10/423,688 and 10/973,693). The GFP structure comprises an eleven-stranded beta barrel (see FIG. 2 A). Circular permutants of GFP were generated by ligating the coding sequences of the native N and C termini, and splicing in new translation start sites at eleven different positions between strands. The constructs and proteins encoded thereby were designated by the strands that begin and end the permutated sequence (i.e., 5' coding/N-termini protein and 3' coding/C-termini protein). Thus, for example, circular permutant GFPcp9/8 has strand 9 at the N-terminus and strand 8 at the C-terminus (i.e., amino acids 173 and 172 of the native GFP structure are, respectively, the N-terminal and C-terminal residues of the GFPcp9/8 circular permutant (see FIG. 2 B). Circular permutant GFPcp8/7 has strand 8 at the N-terminus and strand 7 at the C-terminus (i.e., amino acids 157 and 156 of the native GFP structure are, respectively, the N-terminal and C-terminal residues of the GFPcp8/7 circular permutant (see FIG. 2 C). The brightest circular permutants were GFPcp9/8 and GFPcp8/7 (FIGS. 2B, 2C), as previously observed (U.S. application. Ser. No. 10/423,688). These were selected for further study as folding reporters (vide infra).

Insertion GFP reporters were generated from GFPcp9/8 and GFPcp8/7, by inserting a cloning site for test proteins between the native N and C-termini using primer-based PCR methods of gene construction well known in the art (FIG. 3). Test proteins are inserted into the cloning site using the NdeI and BamHI cloning sites. The primers used to PCR amplify the test protein DNA for cloning are devoid of stop codons and are designed such that the test protein is in-frame with the sequence of the flanking GFP domains. A frame-shift stuffer with stop codons is provided between the NdeI and BamHI site to guard against false-positives arising from undigested plasmid. Thus constructs without the cloned test insert are non-fluorescent since only the first fragment of the GFP scaffolding (in front of the cloning site) is translated.

Example 2

Engineering Variably Stringent GFP Insertion Vectors

Using the GFPcp9/8 and GFPcp8/7 topologies, four vectors corresponding to each topology were generated by combining domains from the two GFP variants, $GFP_{SF}$ and $GFP_{FR}$ (U.S. application Ser. Nos. 10/423,688 and 10/973,693). More specifically, for each topology, a cloning site was introduced between the native N and C-termini residue sequences dividing the GFP molecule into two domains. Two vectors were generated by using domains from the same GFP variant, while another two were generated by combining domains from the two variants (FIG. 4). These eight insertion GFP reporter constructs were evaluated for tolerance to inserted test proteins in *E. coli* (see EXAMPLE 3 infra, and FIG. 7).

For both the GFPcp9/8 and GFPcp8/7 topologies, the insertion GFP vectors display variable sensitivities to test protein misfolding (EXAMPLE 3, infra). Accordingly, the invention provides sets of insertion GFP reporters which enable protein folding and solubility testing at variable stringencies.

The GFPcp9/8 and GFPcp8/7 insertion vectors, and were applied to the problem of evolving better-folded variants of misfolded proteins (EXAMPLE 4 and EXAMPLE 5 infra), and were tested for protein artifact discrimination capability (EXAMPLE 6, infra).

Example 3

GFP Insertion Vectors Display Variable Stringencies

Figure 7:
FIG. 7 shows reporter stringency for X-FR (conventional C-terminal folding reporter GFP), four variants of GFPcp9/8, and four variants of GFPcp8/7. Reporter abbreviation above each column designates the identity of the GFP variant from which the flanking fragment is derived. For example, GFPcp9/8_FR/SF means that the GFP fragment in front of the guest insert protein is derived from folding reporter GFP, and the designation SF means the fragment of GFP after the guest insert protein is derived from superfolder GFP. Each row corresponds to one of four test proteins with progressively worse folding. #1=sulfite reductase (dissimilatory subunit); #2=translation initiation factor; #3=3-hexulose 6-phosphate synthase; and 4=polysulfide reductase subunit (Waldo, G. S., Standish, B. M., Berendzen, J. & Terwilliger, T. C. Rapid protein-folding assay using green fluorescent protein. Nature Biotech. 17, 691-695 (1999)). Expressed alone #1 is fully soluble, #2 and #3 are partially soluble, and #4 is totally insoluble. Conventional C-terminal GFP reporter cannot discriminate between folding status of protein #1 and #2 (#2 and #1 are equally bright for C-terminal GFP). In contrast, GFPcp9/8_FR/FR reporter distinguishes that protein #2 is more poorly folded than protein #1 (#2 is fainter than #1 in the case of GFPcp9/8_FR/FR).

The set of four GFP insertion vectors corresponding to each of the GFPcp9/8 and GFPcp8/7 circular permutant topologies were tested for sensitivity to test protein misfolding. Briefly, the coding sequences of four test proteins from the hyperthermophile *Pyrobaculum aerophilum* with known and variable solubilities were inserted into the vectors. Protein #1=sulfite reductase (dissimilatory subunit); #2=translation initiation factor; #3=3-hexulose 6-phosphate synthase; and 4=polysulfide reductase subunit (Waldo, G. S., Standish, B. M., Berendzen, J. & Terwilliger, T. C. Rapid protein-folding assay using green fluorescent protein. Nature Biotech. 17, 691-695 (1999)). Expressed alone #1 is fully soluble, #2 and #3 are partially soluble, and #4 is totally insoluble. Each of the vectors was tested by inserting the *Pyrobaculum* protein and expressing the colonies on nitrocellulose membranes on agar plates using IPTG as described (Waldo et al., 1999). Expression of the insertion constructs displayed variable fluorescence, showing clear differences in the sensitivities of the vectors, as shown in FIG. 7. Neither the C-terminal GFP reporter nor the GFPcp9/8_SF/SF or GFPcp8/7_SF/SF discriminate between folding status of fully soluble protein #1 and partially soluble protein #2 (#2 and #1 give colonies that are equally bright for C-terminal GFP, GFPcp9/8_SF/SF or GFPcp8/7_SF/SF). In contrast, both GFPcp9/8_FR/FR and GFPcp8/7_FR/FR reporters distinguish that protein #2 is more poorly folded than protein #1 (#2 is fainter than #1 in the case of GFPcp9/8_FR/FR and GFPcp8/7_FR/FR).

Example 4

Application of Variably Stringent Vectors in Protein Engineering

This example further illustrates how the insertion GFP vectors of the invention discriminate against internal ribosome binding sites in directed evolution strategies, wherein soluble variants of an insoluble *Mycobacterium tuberculosis* protein, Rv0113, were isolated by directed evolution using a step-wise application of insertion GFP folding vectors with increasing stringency.

Figure 8:
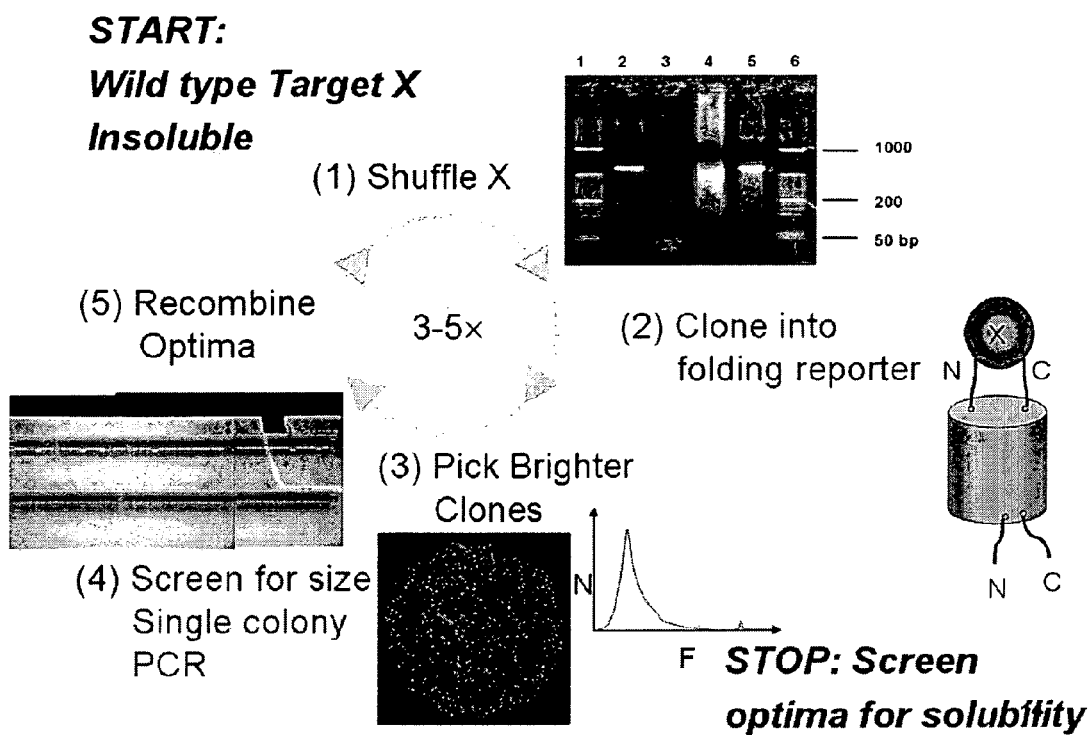
FIG. 8 shows the cyclical four-step directed evolution strategy used to evolve proteins with improved folding using the GFPcp reporters. (1) DNA sequences coding for test protein X is randomly mutated and recombined by DNA shuffling. (2) The library of mutants is cloned into the GFPcp reporter plasmid, transformed into *E. coli*, and the colonies induced with IPTG to express the X-GFPcp fusion protein. (3) Brighter clones are picked and propagated to recover DNA. (4) DNA is screened by single-colony PCR and clones encoding full-length inserts are recombined by DNA shuffling for additional rounds. The process is repeated until there is no further improvement in the fluorescence of colonies.
Figure 9:
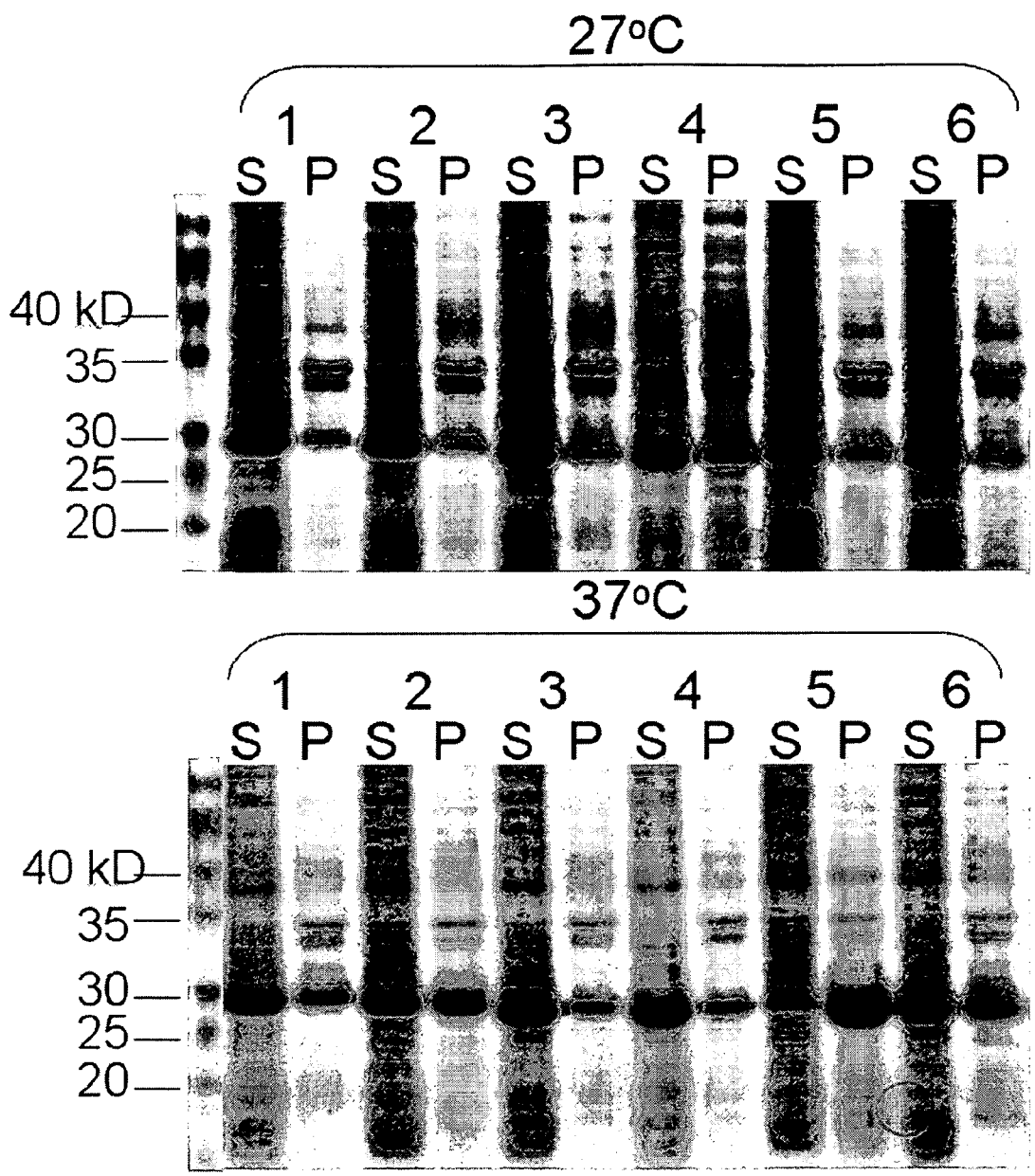
FIG. 9 shows that several independent clones of the evolved Rv0113 are substantially soluble expressed at either 27° C. or 37° C. without the fused GFP. Wild-type Rv0113 is totally insoluble. SDS-PAGE gels of S=soluble fraction or P=insoluble pellet fraction of cell lysates.

The Rv0113 protein was initially subjected to molecular evolution using the C-terminal GFP reporter system. However, this approach only yielded internal ribosome binding site artifacts, and therefore, Rv0113 provided a strong test of the ability of the insertion GFP vectors of the invention to reject internal ribosome binding sites. Three rounds of evolution using a directed evolution protocol, illustrated in FIG. 8, using the moderately-stringent GFPcp9/8_FR/SF vector (FIG. 4 and FIG. 7) gave brightly fluorescent optima expressing partially soluble, full-length fusion protein. SDS-PAGE of soluble and insoluble fractionated cell lysates showed that this evolved Rv0113 was still insoluble expressed alone without the fused GFP domains. After two additional rounds of evolution in the most stringent reporter, GFPcp9/8_FR/FR (FIG. 4 and FIG. 7), SDS-PAGE of fractionated E. coli cell lysates expressing each of several evolved variants of the protein were isolated and shown to be soluble when expressed alone without the fused GFP domains (FIG. 9). All six of these soluble optima of Rv0113 were sequenced, revealing shared consensus mutations V12E, N54D, A106D/T, G109R, and S176F. The mutation N54D occurred only after the additional rounds in the most stringent vector, and is likely key to the improved solubility relative to the first rounds in GFPcp9/8_FR/SF.

Example 5

Application of GFP Insertion Vectors and Directed Evolution to Generate Soluble Variants of Insoluble Proteins The suite of GFP insertion vectors described in EXAMPLE 2 and EXAMPLE 3, supra, were applied to the problem of engineering soluble variants of a set of twelve insoluble proteins from the *Mycobacterium tuberculosis* organism. False positives were completely eliminated, establishing a fundamental advantage of the invention relative to C-terminal GFP reporter systems. In addition, ten of the thirteen proteins were substantially soluble expressed at 27° C. after the application of the directed evolution strategy outline in FIG. 8.

Example 6

GFP Insertion Vectors Discriminate Protein Artifacts

Figure 11:
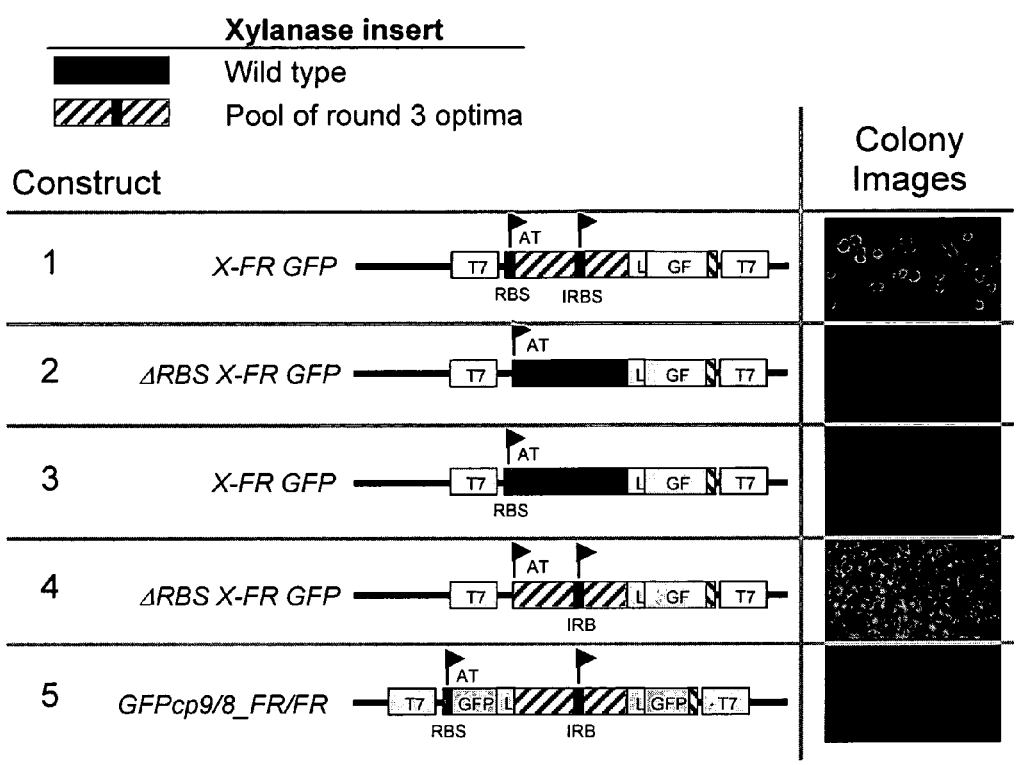
FIG. 11 shows five cases demonstrating the ability of various GFP fusions to discriminate against inserts with internal ribosome binding sites. (1) Pool of optima from round three of evolution of xylanase were bright, but SDS-PAGE showed that the clones expressed truncated protein. (2) Clones expressing wild type xylanase in C-terminal folding reporter vector with no ribosome binding site were non-fluorescent as expected. (3) Clones expressing wild-type xylanase in standard C-terminal folding reporter were weakly fluorescent as expected. (4) Pool of optima were bright expressed from C-terminal folding reporter with no vector ribosome binding site, indicating presence of internal ribosome binding site in xylanase variant. (5) Clones expressing optima pool from circular permutant insertion GFP were faint, as expected, since only the second-half of the GFPcp scaffolding would be fused to a short, soluble truncated protein expressed from the internal ribosome binding site of the xylanase variant.

An insoluble fungal xylanase was subjected to three rounds of directed evolution using the C-terminal GFP reporter described in Waldo et al., 1999. However, SDS-PAGE revealed no full-length protein, even though many clones were bright (FIG. 10, construct 1). Clones expressing the same optima from a modified C-terminal GFP without the vector ribosome binding site were also bright (FIG. 11, construct 4), indicating translation from internal ribosome binding sites within the optima. The same optima subcloned into the GFPcp9/8_FR/FR were non-fluorescent, as expected (FIG. 11, construct 5). This clearly demonstrates the advantage of the present invention in avoiding selection of false-positive truncated artifacts caused by internal translation sites. These sites can arise by mutagenesis during directed evolution or may be present in native constructs.

The experiment was repeated on specific optima (Artifacts I to III, FIG. 12) rather than the entire pool. Again, the circular permutant insertion GFP was able to discriminate against the artifacts (FIG. 12). Sequencing the wild type and bright artifact clones revealed a likely consensus ribosome binding site in the artifacts (FIG. 12).

Example 7

Generation of DHFR Insertion Vector

This example describes the generation of a DHFR insertion vector. *E. coli* dihydrofolate reductase (DHFR) is sensitive to the antibiotic trimethoprim (TMP). Mammalian DHFR is immune to inhibition by TMP, and using it would be expected to provide little discrimination between soluble and insoluble protein fusions. Wild-type *E. coli* expresses a very small amount of DHFR from its genome as part of its metabolism, and *E. coli* is normally sensitive to >0.5 µg/ml of TMP. Over-expression of large amounts of folded *E. coli* DHFR from a pET vector expression system allow *E. coli* to survive in media containing up to 256 µg/ml TMP.

Figure 5:
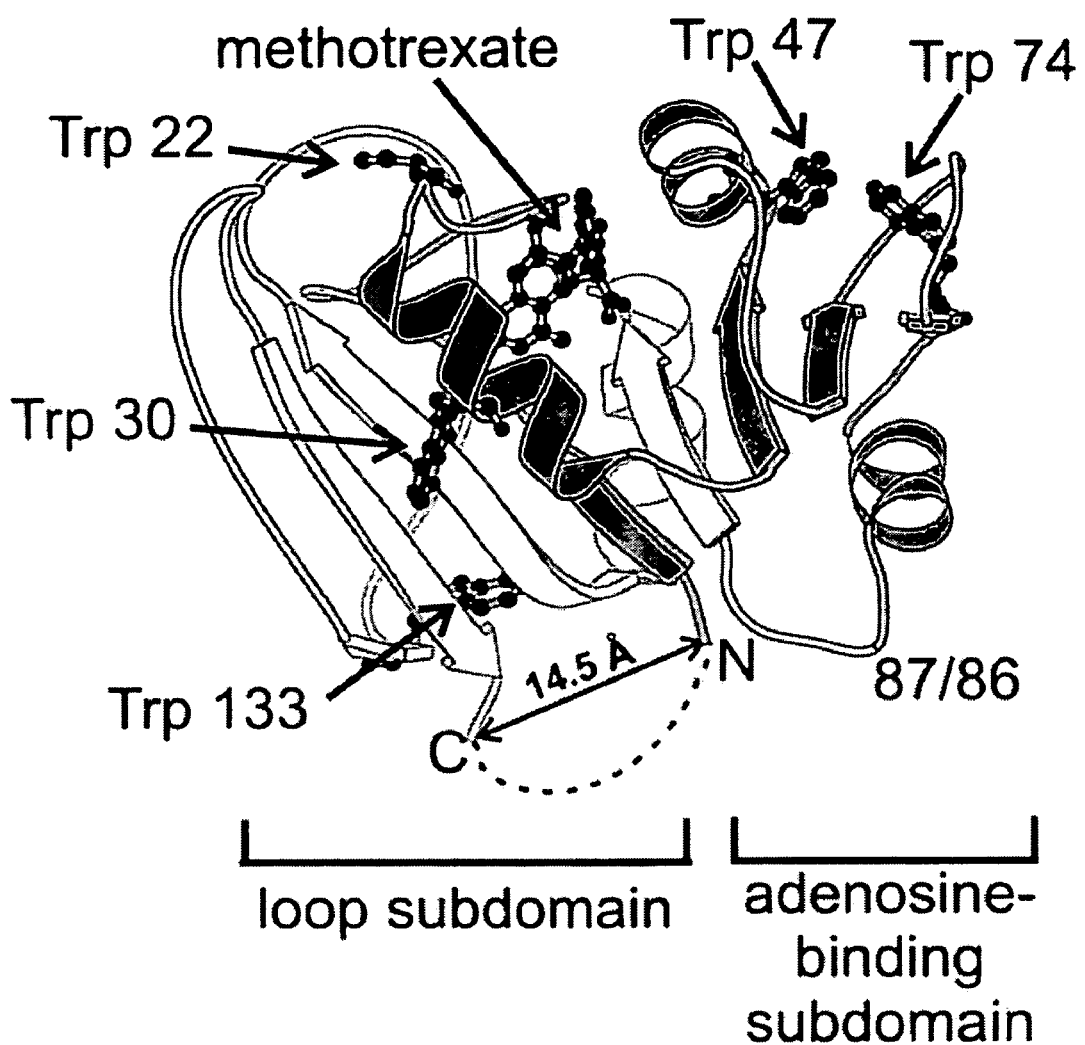
FIG. 5 shows a ribbon-diagram representation of the three-dimensional structure of *E. coli* dihydrofolate reductase. Amino acids 87/86 are denoted near the linker site (amino acid 87) used for insertion of guest proteins. Structure reproduced from (Smith and Matthews 2001).

*E. coli* DHFR has been studied to find permissible circular permutant start sites (Iwakura, Nakamura et al. 2000; Murai, Mori et al. 2000; Maki and Iwakura 2001; Smith and Matthews 2001; Arai, Maki et al. 2003) that can serve as sites for the insertion of foreign polypeptides. *E. coli* DHFR is a modular protein with a flexible linker connecting two domains at amino acid 88 (see FIG. 5).

The internal EcoR-1 restriction site in *E. coli* DHFR was eliminated by silent mutagenesis, cloned into a pET vector, and engineered to contain a cloning site by PCR at amino acid 88 using primer cassette mutagenesis. The resulting structure of the vector in the vicinity of the construct is:

5'-T7promoter::RBS/ATG::Nco-1::DHFR1-87:: LINKER::NdeI(Frame-shift stuffer)BamHI:: LINKER::DHFR 88-158(Stop codon)::Xho-1-3'

(RBS=ribosome binding site in commercial pET vector, Novagen, Madison Wis.).

The structure of the expressed protein fusion (with inserted protein X) is:

$NH_2$-DHFR1-88-LINKER-HM-Protein X-GS-LINKER-DHFR88-158-COOH

The "LINKER" referenecd above has the amino acid sequence:

GGGSGGGS [SEQ ID NO: 25]

See also TABLE OF SEQUENCES, infra, for complete DNA and amino acid sequences.

Example 8

Positive Correlation Between Non-Fusion Solubility and Survival of Insertional DHFR Fusions in Trimethoprim-Containing Media To test the utility of the DHFR insertion reporter for selecting proteins based on solubility, eight different *Pyrobaculum aerophilum* proteins were expressed as insertion fusions in the DHFR reporter vector described in Example 7, supra. The solubility of the non-fusion genes expressed in *E. coli* at 37° C. had been previously determined (Waldo, Standish et al. 1999).

The genes were clone using NdeI and BamHI restriction sites, and clones were grown in Luria-Bertani (LB) liquid culture to ca. 1.0 OD 600 nm, then induced with 10 µM isopropylthiogalactoside (IPTG) for 1 h at 37° C. A 96-well tissue culture plate was set up in which each of the eight rows was assigned to a gene, and each of the twelve columns contained increasing amounts of trimethoprim (0.25, 0.5, 1.0, 2, 4, 8, 15, 32, 64, 128, 256, 512 µg/ml) in LB media containing 10 µM IPTG. The 1.0 stocks were diluted 1000-fold into the tissue culture plate, and grown overnight at 30° C. shaking at 350 orbits per minute. The optical density at 600 nm was measured after overnight growth using FL600 Microplate Fluorescence Reader (Bio-Tek, Winooski, Vt.). Optical density at 600 nm greater than or equal to 0.1 was interpreted as indicating cell survival and growth.

As expected, survival was positively correlated with insert solubility, with the exception of tyrosine t-RNA synthetase (see FIG. 13). This gene is involved in *E. coli* protein translation and could potentially interfere with cell survival over extended periods of time.

Example 9

DHFR Insertion Reporter Used as ORF (Open Reading Frame) Filter

Using the protocol outlined in Example 8, *E. coli* cells expressing a DHFR insertion reporter containing a frame-shifting insert with stop codons in all three frames were tested for survival at several concentrations of trimethoprim. Expression of the DHFR frame-shift insert construct failed to generate surviving *E. coli* cells, even at very low concentrations of trimethoprim (see FIG. 13). This is expected since only the first 88 amino acids fragment of the DHFR construct was over-expressed, due to the presence of the stop codons in the insert. In contrast, DHFR expressing the inserted, very poorly soluble polysulfide reductase subunit survive up to 16 ug/ml trimethoprim (see FIG. 13). Thus, the DHFR insertion reporter is useful for selecting in-frame inserts containing no stop codons, regardless of solubility, by exposing the expressing *E. coli* cells to very low concentrations of trimethoprim (ca. 0.25-8.0 μg/ml). Under these conditions, inserts which are out-of-frame or contain stop codons, as well as *E. coli* containing no DHFR plasmids (untransformed *E. coli*) are killed, while *E. coli* cells expressing DHFR with even poorly folded inserted proteins survive (see FIG. 13). Inserts passing through such an ORF filter assay may be screened for solubility using any type type of solubility reporter, including for example the GFP insertion reporters of the invention and the split GFP systems described in U.S. patent application Ser. No. 10/973,693 and in Cabantous, S., Terwilliger, T. C. & Waldo, G. S. (2005) "Protein tagging and detection with engineered self-assembling fragments of green fluorescent protein." Nat. Biotech. 23(1): 102-7. Published online 5 Dec. 2004; doi:10.1038/nbt1044.

Example 10

Trapping Soluble Domains of Proteins Using the DHFR Insertion Reporter

This example demonstrates the succeful use of the DHFR insertion reporter to trap soluble domains of the human Nod2 protein. The full-length protein is normally insoluble when expressed in *E. coli*.

Figure 14:
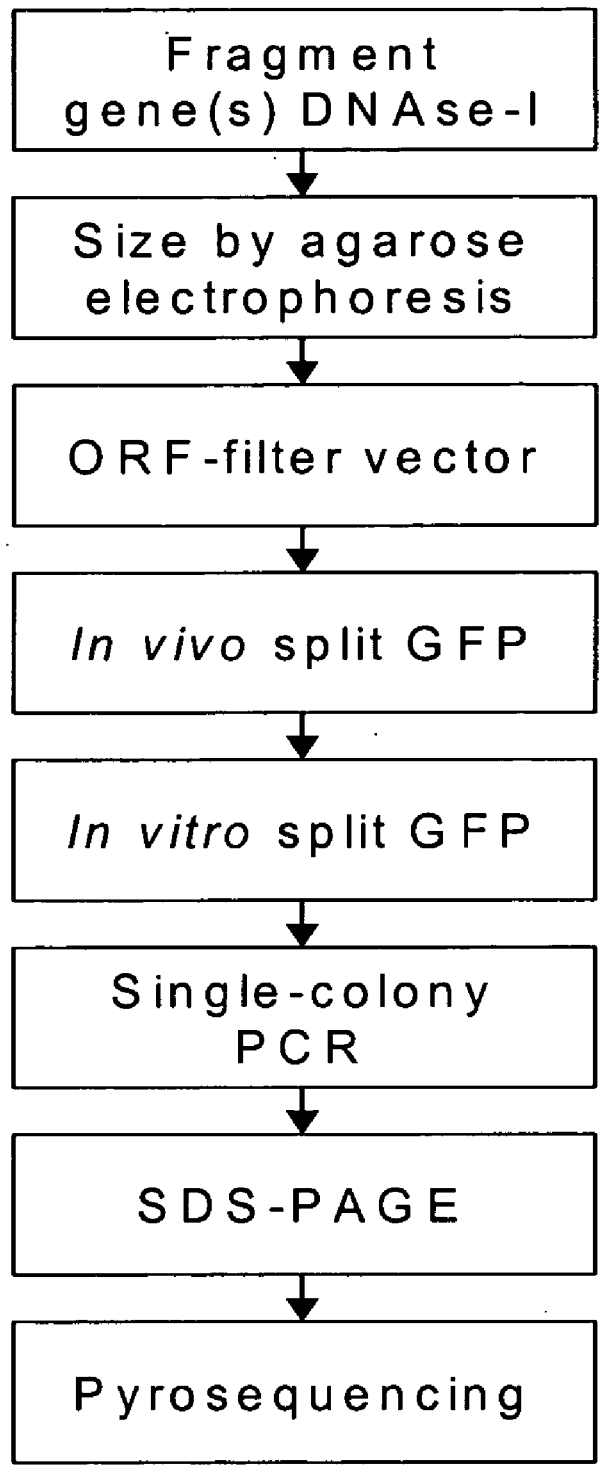
FIG. 14 shows the strategy for trapping soluble domains of proteins or genomes. DNA is fragmented, cloned into the DHFR insertion reporter and selected on low concentration (0.2 to 5 ug/ml) trimethoprim to select in-frame fragments, which are subcloned into the split-GFP solubility reporter, evaluated for in-vivo solubility. The brightest, most soluble clones are screened for in vitro solubility using the split GFP complementation assay, and sequenced to determine the boundaries of the fragment by reference to the known gene or genomic DNA sequence.

The approach used is illustrated by the flowchart shown in FIG. 14. Briefly, Nod2 encoding DNA was amplified by PCR, fragmented using DNAse-I, blunted using proof-reading polymerase Vent (New England Biolabs), and fragments of between about 200 and 1000 bp were isolated by preparative agarose gel electrophoresis. Only one in three fragments are expected to have the 5' end in-frame with the upstream DHFR scaffolding. Only one in three fragments are expected to have the 3' end in-frame with the downstream DHFR scaffolding. Since the fragments are blunt-cloned into the Stu-I site of the DHFR vector insert cloning site, only one in two are in the correct orientation. Thus only 1 in 18 fragments were expected to be in-frame and in the correct orientation, so the fragment library was inserted into the DHFR insertional reporter (denoted as "ORF-filter vector" in the flow-chart FIG. 14) and expressed in *E. coli* grown in media containing 8 μg/ml trimethoprim. Selection with this concentration of trimethoprim is effective at selecting in-frame clones regardless of solubility (see FIG. 13).

Figure 15:
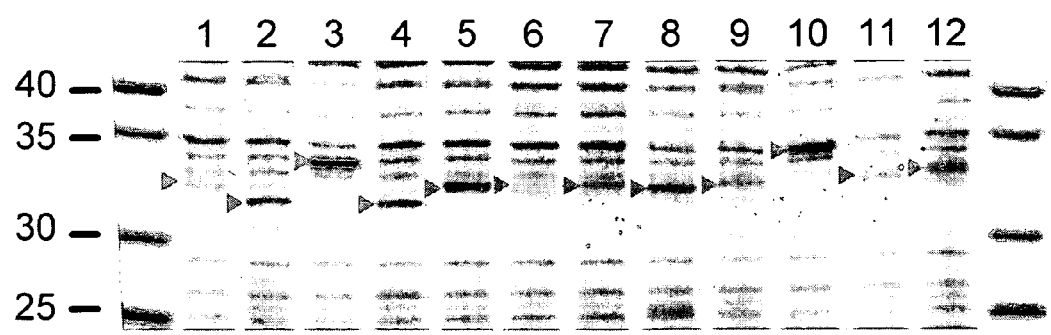
FIG. 15 shows an SDS-PAGE gel image of trapped soluble domains of Nod2, identified according to the protocol outlined in FIG. 14. Clones are expressed from the tet promoter and have a C-terminal GFP M3 split GFP tag (Cabantous et al., 2004). (soluble fraction). Lanes 2, 3, 4, 5, 8, and 10 are well expressed.

Inserts from surviving clones were subcloned into a split GFP tagging vector using the flanking NdeI and BamHI sites, with a ColE1 origin, spectinomycin selectable marker, containing an N-terminal 6-HIS tag and C-terminal GFP strand 11 tag "GFP S11 M3" (SEQ ID NO: 15, U.S. patent application Ser. No. 10/973,693, and Cabantous et al., 2004) and transiently expressed in *E. coli* containing a pET vector with p15 origin and kanamycin-selectable marker expressing the optimized GFP 1-10 OPT fragment from the T7 promoter. Following expression of the GFP 1-10 OPT using IPTG (as described in Cabantous et al., 2005, approximately 20,000 clones were screened in vivo for the 96 brightest clones. Briefly, clones were plated on nitrocelluose and grown overnight to ca. 0.5 mm diameter, cells on membranes were incubated for 1.5 h on a plate containing 250 ng/ml AnTet at 32° C., 1 h on a resting plate, and finally 1 h on 1 mM IPTG plate at 37° C. These clones were grown in liquid culture, induced only with AnTet at 32° C. to express just the GFP S11 M3 constructs, and lysates were screened in vitro using the split GFP system to precisely quantify total expression and solubility, as described in Cabantous et al. 2004, and the clones were verified to bind metal affinity resin via the N-terminal 6HIS tag, by fluorescence of the reconstituted C-terminal GFP, thereby fluorescence confirmed that they were full-length. Soluble fractions from the 12 best candidates (most soluble and best-expressed) were analyzed by SDS-PAGE (FIG. 15).

Example 11

Trapping Soluble Domains of the *Mycobacterium tuberculosis* pks13 Gene Using DHFR Insertion Reporter and Split GFP Assays This example shows the combined use of the DHFR ORF filter and split GFP solubility assay technologies to isolate soluble domains of the pks13 gene from *Mycobacterium tuberculosis*. The split GFP technology utilized is described in published U.S. patent application no. 20050221343 A1.

Figure 16:
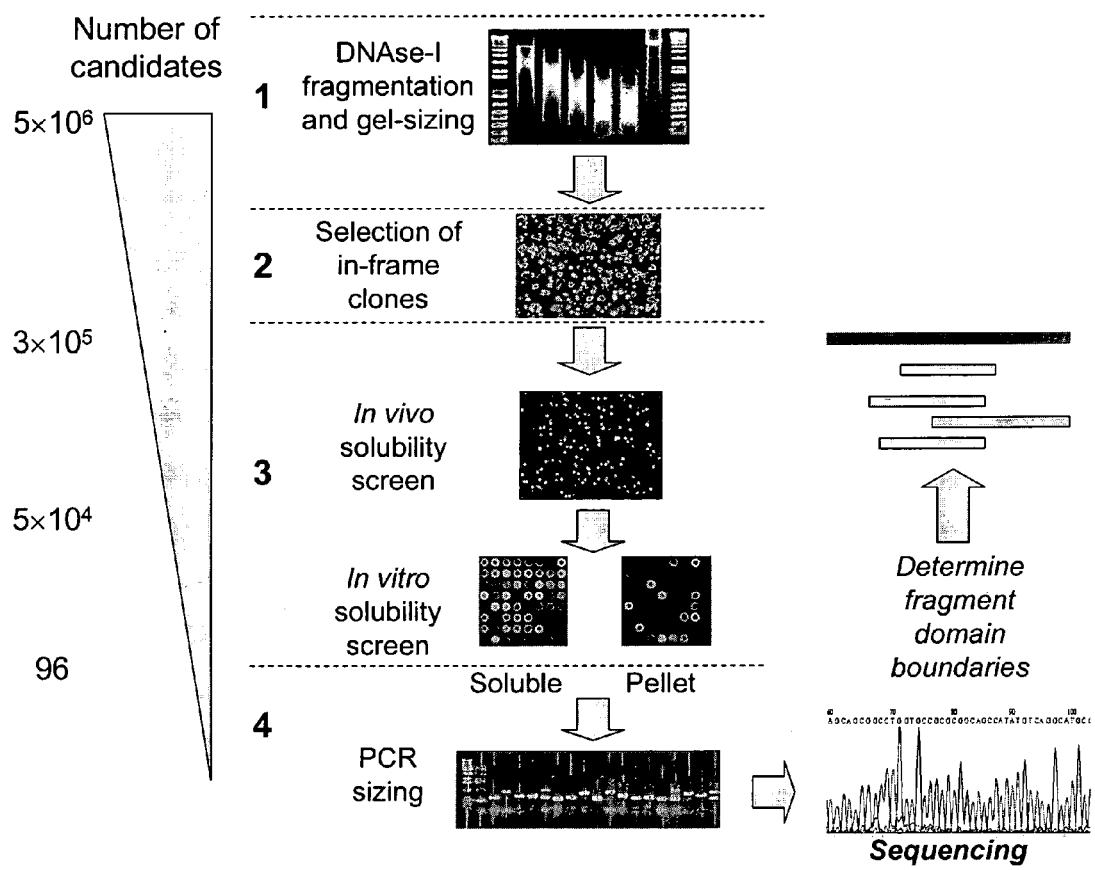
FIG. 16. Screening protein domain solubility using ORF filter and split-GFP. (1) Gene is fragmented by DNase-I and sized by preparative agarose gel electrophoresis. (2) DHFR ORF-filter selects in-frame blunt-cloned fragments. (3) In-vivo split GFP solubility reporter identifies clones likely expressing soluble protein, while the in vitro split GFP assay quantifies soluble and insoluble protein expressed in small liquid cultures. (4) PCR is used to sort fragments by size, and sequencing precisely determines the fragment boundaries, which are aligned on the original ORF. Results are combined with bio-informatics to select candidates for crystallization.

The multi-step strategy used comprises four distinct steps as described below. False positives at any given step are effectively eliminated by the following step, since each step provides more detailed information than the previous step. Each step has a progressively lower throughput, so the arrangement of the multi-tier approach tailors the number of candidates to match the screening or selection capacity at the following step. This reduces false-negatives and eliminates potential false positives (FIG. 16).

Gene fragmentation: a diversity of protein fragments is created by fragmentation of a PCR amplified gene using DNaseI; and fragments of the desired size are recovered by preparative agarose gel electrophoresis.

Selection of clones containing "in-frame" inserts using the DHFR insertional vector or "ORF-filter" vector using low concentration of trimethoprim (0.25 to 8.0 μg/ml). This selects in-frame fragments regardless of solubility. When an ORF is randomly fragmented and blunt-cloned into a fusion-protein destination vector, only 1 in 18 of

- the fragments will be in the original reading frame of the parent ORF, and also in the frame of the reporter destination vector.
- Selection of soluble clones with two successive in vivo and in vitro screenings using the "split-GFP" technology. The brightest, most soluble clones selected in vivo are screened for in vitro solubility using the split GFP complementation assay.
- Characterization of the fragments size by single colony PCR. DNA sequencing is used to determine the boundaries of the fragment by reference to the known gene or genomic DNA sequence.

MATERIALS AND METHODS

Fragmentation of pks13 Gene

Amplification of pks 13 Gene:

The pks13 gene from *Mycobacterium tuberculosis* cloned NdeI/HindIII in a pET26b plasmid (Novagen, Madison, Wis.) resulting in the PWM35 plasmid was provided by Christian Chalut (Ghuilot team, IPBS, Toulouse). Gene amplification tests were performed by conventional PCR (25 cycles of 94° C. 45', 57° C. 45', 72° C. 1 min/kb for Vent and Platinum, 2 min/kb for Pfu) using the PWM35 plasmid as starting template and pET28a vectors specific primers:

```
                                        [SEQ ID NO: 26]
5'primer: ATGGTGCATGCAAGGAGATGGCGCCCAACA
(4899+)

[SEQ ID NO: 27]
3'primer: GAGGCCTCTAGAGGTTATGCTAGTTATTGC.
(02129811)
```

Several polymerases were tested: Vent® exo+ (New England Biolabs, Beverly, Mass.), Pfu® (Stratagene, La Jolla, Calif.) and Platinum Taq Polymerase® (Invitrogen, Carlsbad, Calif.). A larger PCR reaction was set up with Platinum Taq Polymerase (300 μl) and cleaned with Qiaquick PCR purification kit (Qiagen Inc. USA, Valencia, Calif.).

Optimization of Dnase I Digestion Conditions:

Three samples of desoxyribonuclease I (DNase I) were diluted in appropriate buffer (10×BSA, 10 mM Tris pH 7.4) in a ratio of 1/16, 1/8 or 1/4 from a 1 AU/μl stock solution (Invitrogen, Carlsbad, Calif.) to a final volume of 25 μl. For testing reaction times, 25 μl of cleaned PCR product were mixed with 3 μl of 0.5M Tris pH 7.4, 0.5 μl 100 mM $CoCl_2$ and incubated in a PCR block at 15° C. for 15 min. At t=0, 0.3 μl of diluted DNase I were added and mixed thoroughly to start the reaction. 3 μl aliquots of the digestion reaction were taken out at defined time-points and mixed with 3 μl of Quenching Buffer to stop the reaction (80 μl 6×-DNA Buffer (Maniotis), 20 μl EDTA 0.5M pH 8.0). At the end of time digestion analysis, the different samples were resolved on 0.7% agarose/TAE gel electrophoresis. Digestion products were visualized using ethidium bromide staining.

Gene Fragmentation and Sizing

Large Scale DNase I Digest:

Three large scale reactions were set up in 85 μl reaction volume using the same ratio of reagent/DNA sample as described above. After incubation at 15° C., 1 μl of 1/8 diluted DNase I was added and the samples were incubated during optimal digest times previously determined (2 min, 4 min and 8 min). The reactions were stopped by mixing the reaction volume with 850 μl of PB buffer (Qiagen Inc. USA, Valencia, Calif.), and cleaning through a QiaquickPCR purification column.

Creating Blunt-End DNA Fragments:

Extremities of the cleaved products were polished using 3'-5'exonuclease activity of Vent® polymerase (New England Biolabs, Beverly, Mass.). 77 μl of sample were mixed in 1× Thermopol® buffer, 0.25 mM dNTPS, 10 mM $MgSO_4$ and 1.4 μl Vent exo+, and incubated at 72° C. for 20 min.

Sizing the Fragment Library on Gel Electrophoresis:

Preparative gel electrophoresis was used to size the fragments in the desired range. Pools of blunted fragments were cleaned, precipitated with EtOH, 0.5 mM $MgCl_2$ and loaded on a 0.7% Agarose/TAE preparative gel. The gel bands were cleaned through a QiaquickPCR gel extraction kit.

Selection of In-Frame Fragments

Construction of DHFR Insertion Library:

Fragments were ligated in a StuI-digested DHFR insertion pET vector (38/10 μl insert/vector ratio) for 12 h at 16° C., and used to transform electro-competent *E. coli* DH10B cells. The transformed cells were plated on LB (Lenox Brox) media containing 35 μg/ml Kanamycin, and were grown at 37° C. for 14 h. The lawn of cells was washed off the plates, and used to make a plasmid prep, which was then transformed into chemically competent *E. coli* BL21 (DE3) Tuner cells. After overnight growth at 32° C. on Kanamycin selective media, BL21 (DE3) Tuner cells were diluted into LB, 20% Glycerol for a 1.0 $OD_{600}$ frozen stock.

Trimethoprim Selection of In-Frame Fragments in DHFR Insertion Vector:

40 μl of the 1.0 OD frozen expression libraries were used to seed a 3 ml LB/35 μg/ml Kan culture. Cells were propagated for about 2 h30. When $OD_{600}$=0.5 was reached, cells were induced with 20 μM IPTG for another 2-3 h. At the end of the induction, *E. coli* cells were diluted in 1 ml LB to a density of $10\times10^8$ cells/ml and plated on LB media containing 6 μg/ml trimethoprim (TMP) and 20 μM IPTG. To compare the CFU number in conditions of TMP selection and no selection, cells were further diluted to 1/160000 and plated onto LB media containing 6 μg/ml TMP and 20 μM IPTG, or on LB media containing only 20 μM IPTG. All plates were incubated overnight at 33° C.

Selection for Solubility Using Split GFP

Subcloning of Fragments from DHFR Vector to Split-GFP Vector:

The recovered DHFR libraries were diluted in 20% glycerol LB for a −80° C. frozen stock and cell aliquots were simultaneously used to make plasmid preps. The plasmids were restricted using NdeI/BamHI, and released fragments were sized on preparative electrophoresis in the same size range as they were after the fragmentation step and blunting step (above). To avoid excessive diffusion of fragments through the gel, electrophoresis was completed in ca. 5 min. Gel extracted and cleaned inserts were ligated in an NdeI/BamHI-digested pTET ColE1 GFP 11 vector.

In Vivo and In Vitro Solubility Assay:

In vivo solubility screening was performed as described in published U.S. patent application no. 20050221343 A1. Thirty two clones exhibiting different levels of in vivo fluorescence were picked for each library. The same clones were used as starter cultures in tissue culture plates, used to inoculate 1 ml deep well plates which were grown and induced for 3 h at 27° C., with 300 ng/ml AnTET only. The soluble and pellet fraction was fractionated and both soluble and pellet protein quantity was assessed using in vitro complementation split GFP assay. Moles of expressed protein were estimated using a calibration of fluorescence from standards of GFP 11 tagged sulfite reductase.

Talon 6HIS Affinity Bead-Binding:

40 µl of a 50% v/v slurry of metal affinity resin beads (Talon resin, Clontech, Palo Alto, Calif.) in TNG buffer was added to the microplate complemented soluble fraction. The beads and the samples were mixed on a shaker for 10 minutes and centrifuged briefly. The unbound fraction was removed using vaccum. The same operation was repeted by mizing the beads with 200 µl of TNG buffer. Finally, the beads were diluted 200 µl with TNG and the beads fluorescence (λexc=488 nm, λem=530 nm) was monitored with a FL600 Microplate Fluorescence reader (Bio-Tek). The background fluorescence of a blank sample (TNG+beads) was substracted from the final fluorescence values.

Characterization of the Fragments:

Single Colony PCR:

The equivalent of 2 µl of glycerol stocks from the clones screened in vivo for solubility were used as a template for the specific PCR amplification of the Pks13 fragments. Primers specific of the tet promoter,

[SEQ ID NO: 28]
TAGAGATACTGAGCACATCAGCAGGACGCACTGACC and of the GFP 11 tag,

[SEQ ID NO: 29]
TACTTCGGTACCTGTAATCCCAGCAGCAGTTACAAA were used, in 12 µl PCR reactions with Vent exo+DNA polymerase (NEB). Single colony reactions were loaded on agarose gel electrophoresis, and visualized after EtBr staining. Gel bands sizes were determined by comparison with 1 kb Plus DNA ladder (Invitrogen) using Biorad Densitometer Software Quantityone®.

DNA Sequencing:

A subset of clones was selected from the single colony PCR and solubility analysis. 50 µl PCR reactions were set up similarly as for the colony PCR screening. For each sample, 10 µl sequencing reactions used 3 µl of the cleaned PCR product and 1 µl of forward primer (primer specific of tet promoter, above) or reverse primer (primer specific of GFP 11, above). Cleaned DNA samples were sequenced at the Plant Microbe genomics Facility (Ohio State University, OH), which uses an Applied Biosystems 3730 DNA Analyzer and BigDye™ cycle sequencing terminator chemistry. DNA sequences were analyzed using BioEdit® software. Sequences alignments were performed individually with the full length gene Rv3800 (http://www.tbgenomics.org) to determine the exact boundaries from the forward sequence (start of the fragment) and reverse sequence (end of the fragment).

Expression and Solubility Tests

Expression of the Domains in Two Expression Vectors:

Selected domains subcloned from a pTET-GFP11 plasmid into a pET-N6HIS and pTET-N6HIS vectors bearing the cloning cassette: NcoI-6HIS-NdeI-frame shift-BamHI-stop-XhoI-XbaI via NcoI/XbaI restriction sites. The resulting clones were grown at 37° C. in 3 ml cultures using either $Spec^R$ (PTET expression) or $Km^R$ (pET expression). Cells were induced in the exponential phase with 250 ng/ml AnTET for 5 h for the pTET-N6HIS constructs, or 1 mM IPTG for 5 h for pET-N6HIS constructs. 3 ml cell culture pellets of eighteen subcloned domains were separately suspended in 1.5 ml TNG buffer and sonicated. The lysate was fractionated by centrifugation to yield the soluble and the pellet fractions. The pellet fraction was washed once with 500 µl TNG, centrifuged and resuspended again in the same starting volume.

6HIS Affinity Resin Purification of Selected Domains:

50 ml cultures of BL21(DE3) cells expressing each domain were grown to $OD_{600}$~0.5, induced with 1 mM IPTG for 5 h at 25° C., pelleted by centrifugation, resuspended in 2 ml TNG, and sonicated. 1.5 ml of the soluble extract was mixed with an equal volume of 50% v/v slurry of metal affinity resin beads (Talon resin, Clontech, Palo Alto, Calif.) in TNG buffer for 10 minutes and centrifuged briefly. The unbound fraction was removed by pipetting and the beads were washed twice with 10 volumes of TNG loading buffer. After an additional wash with TNG buffer supplemented with 10 mM imidazole, HIS-tagged proteins were eluted with 250 mM imidazole in TNG buffer. For each purification step, the proteins elution samples were resolved on a 4-20% gradient Criterion SDS-PAGE gel (Bio-Rad, Hercules, Calif.). The protein samples were stained using Gel Code Blue stain reagent (Pierce, Rockford, Ill.) and imaged using a GS-800 Calibrated Densitometer (Biorad, Hercules, Calif.).

Solubility Determinations by SDS-PAGE:

15 µl of the soluble and pellet fractions were mixed with 15 µl of 2×SDS-denaturing buffers and were heated for 15 min at 100° C. The denaturated samples were resolved on a 4-20% gradient Criterion SDS-PAGE (Biorad, Hercules, Calif.). The protein samples were stained using Gel Blue Code reagent (Pierce, Rockford, Ill.) and quantified using a GS-800 Calibrated Densitometer (Biorad, Hercules, Calif.). The total expressed protein content was estimated by adding the densities of the soluble (Ds) and the pellet fraction (Dp) and the solubility was defined as S=Ds/(Ds+Dp).

Results: Trapping Soluble Domains of pks13

Figure 17:
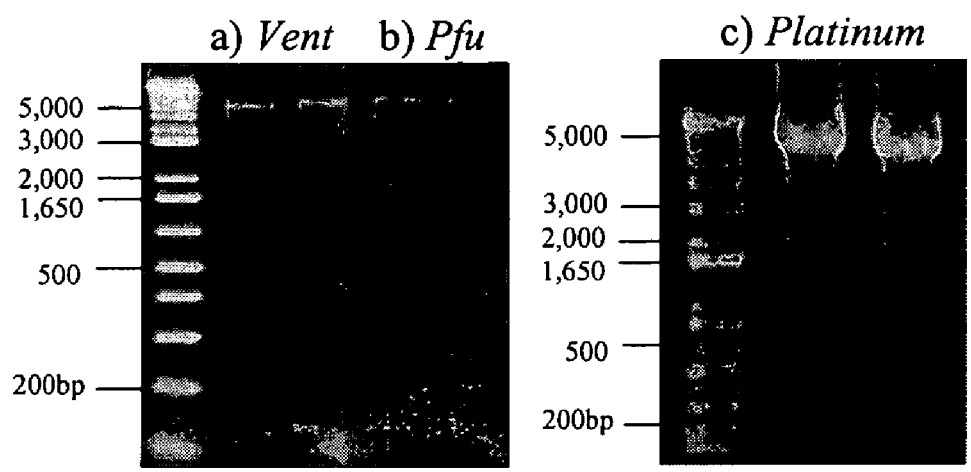
FIG. 17 Amplification of the pks13 gene using different DNA polymerases. (a) Vent (NEB). (b) Pfu (Stratagene). (c) Platinum Taq High Fidelity (Invitrogen).

Optimization of PCR Amplification:

DNase I gene fragmentation requires ca. 1-2 µg of target DNA. The large size of the pks13 gene (5 kb) and its high GC content rendered it difficult to amplify. Amplification tests using classical DNA polymerases like Vent or Pfu (Stratagene, La Jolla, Calif.) produced insufficient PCR product (FIG. 17a, b). Acceptable amplification was achieved using Platinum Taq DNA polymerase High fidelity (Invitrogen, Carlsbad, Calif.) (FIG. 17c).

Figure 18:
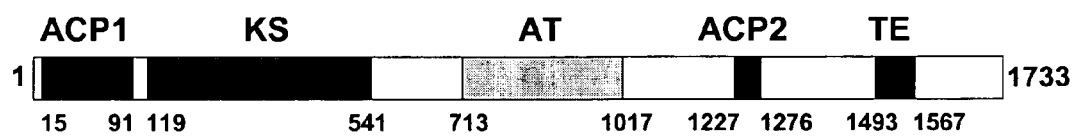
FIG. 18 shows a representation of the Pks13 enzyme and its functional domains.
Figure 19:
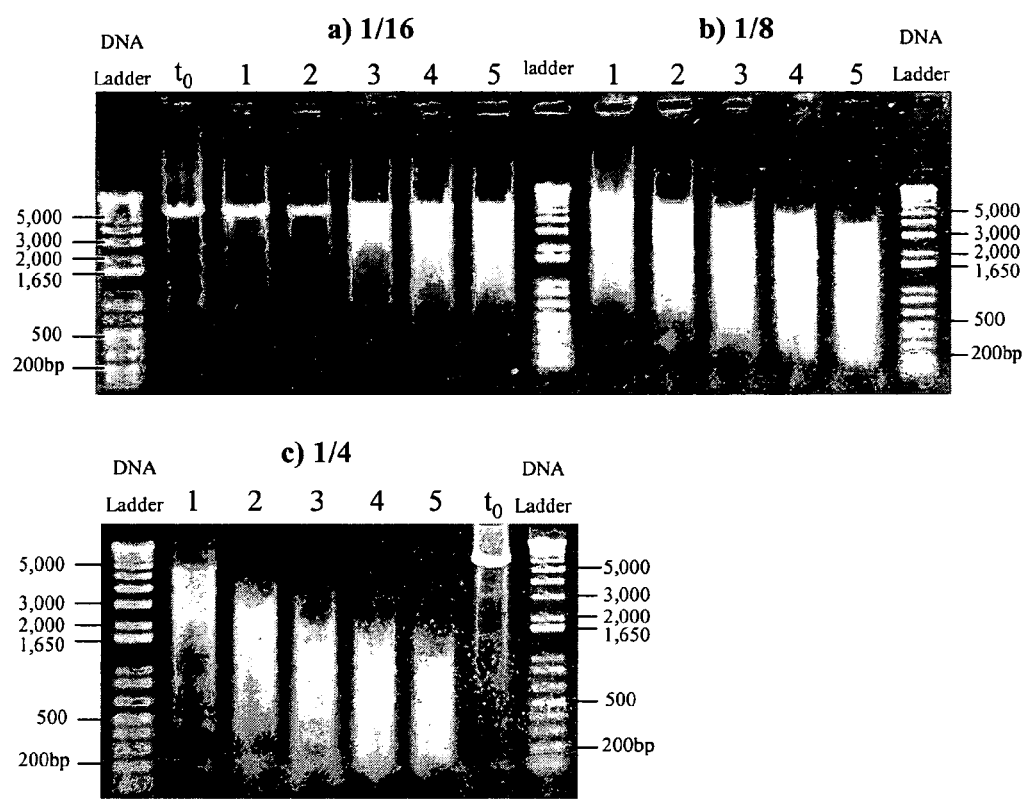
FIG. 19. Adjusting DNaseI digestion reaction conditions. The reaction was stopped at different times (1, 2, 3, 4, 5 minutes). Three differents dilutions of DNase I enzyme stock solution (1 unit/μl) were tested. (a) DNase I diluted 16-fold. (b) DNase I diluted 8-fold. (c) DNase I diluted 4-fold. A large scale digest (75 μl) was performed in optimal digest conditions: 8 min incubation time for the 300-1500 kb range (library I), 4 min incubation time for the medium 1000-3000 bp range (library II), and 2 min digestion time for the high 1500 to 4000 bp fragment range (library III).

Optimization of DNAse I Digestion Conditions:

The size of the predicted functional domains of Pks13 varies from 500 bp to 2000 bp, and two consecutive domains may reach 3 kb in size (FIG. 18). Since DNA ligation efficiency varies inversely with the size of the insert, to avoid biased ligation of small fragments, three individual libraries of fragments were created: from 500 bp to 1500 bp, from 1000 bp to 2000 bp, and from 1500 bp to 4000 bp. The two larger fragment size libraries would let us "fish" candidate soluble double-domains or large single-domains, whereas the smaller fragment size library would favor the selection of smaller soluble domains or sub-domains. DNase I reaction conditions were optimized in order to create a high concentration of fragments in the desired size range. Small aliquots of concentrated PCR products were incubated in reaction buffer with decreasing amounts of DNase I. The reaction was stopped at five different incubation time-points (1, 2, 3, 4, 5 min) (see Methods) and digestion products were analyzed by agarose gel electrophoresis (FIG. 19).

Figure 20:
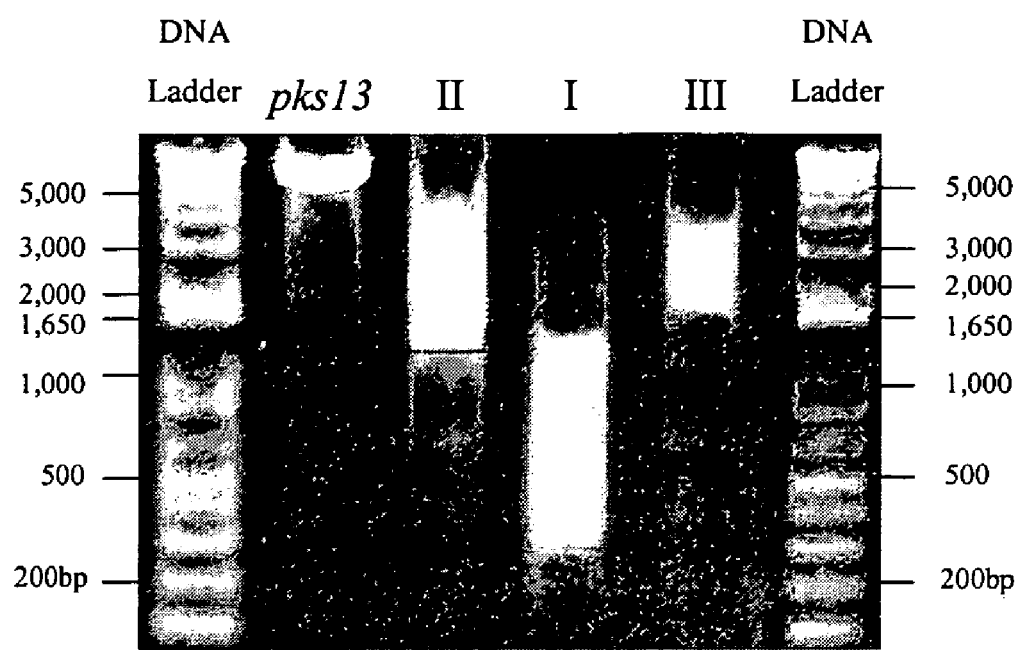
FIG. 20. Analytical gel electrophoresis of recovered blunted DNA fragment libraries after sizing by preparative gel electrophoresis.

Sizing Preparative Gel Electrophoresis:

Immediately after DNase I digestion, the fragments were blunted using Vent exo+polymerase (New Englad Biolabs, Beverly, Mass.) (see Methods) and sized by preparative gel electrophoresis to yield three fragment pools: Library I (300 bp-1500 bp), Library II (1000 bp-3000 bp) and Library III (1500 bp-4000 bp) (FIG. 20).

Selection of In-Frame Fragments: Construction of cDNA Library in DHFR Insertion Vector:

The three independent pools of blunted pks13 fragments were cloned into a StuI pre-digested DHFR insertional vector and transformed into *E. coli* DH10B cells (Calvin and Hanawalt 1988; Dower, Miller et al. 1988). The plasmids were individually pooled for each of the three libraries, which each contained about 5.106 clones, and used to transform *E. coli* BL21 Tuner™ (DE3) competent cells (Novagen, San Diego, Calif.). BL21Tuner™ (DE3) contains the lacY permease mutation to ensure the uniform induction of the cells by IPTG during the subsequent selection for in-frame clones. Lawns of transformants were recovered and stored as 1 OD stocks in 20% glycerol at −80° C.

Figure 21:
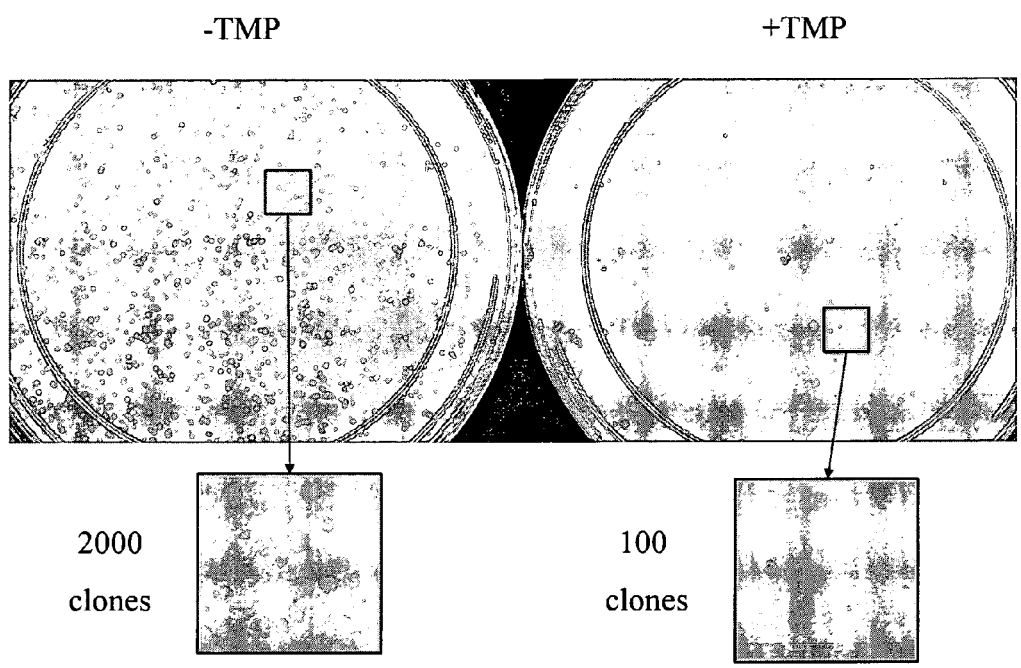
FIG. 21. Effect of the trimethprim selection on the DHFR insertion expression library survival. After overnight growth at 32° C., the selection plate (right) displayed about 1/20 of the clones present in the control plate (left).

Fragments that do not contain stop-codons will produce a functional DHFR and survive on selective media containing TMP (See Chapter VI). Expression libraries were grown in liquid culture and induced for 1 h at 32° C. with 20 μM IPTG before plating on solid media containing the selective agent TMP at 6 μg/ml. A sample of each library was diluted and plated on media with and without TMP for accurate colony counts (FIG. 21). The number of surviving clones on TMP+ plates was approximately $1/20^{th}$ that of TMP− plates, corresponding well with the expected number of in-frame clones (1 in 18) (FIG. 21).

Figure 22:
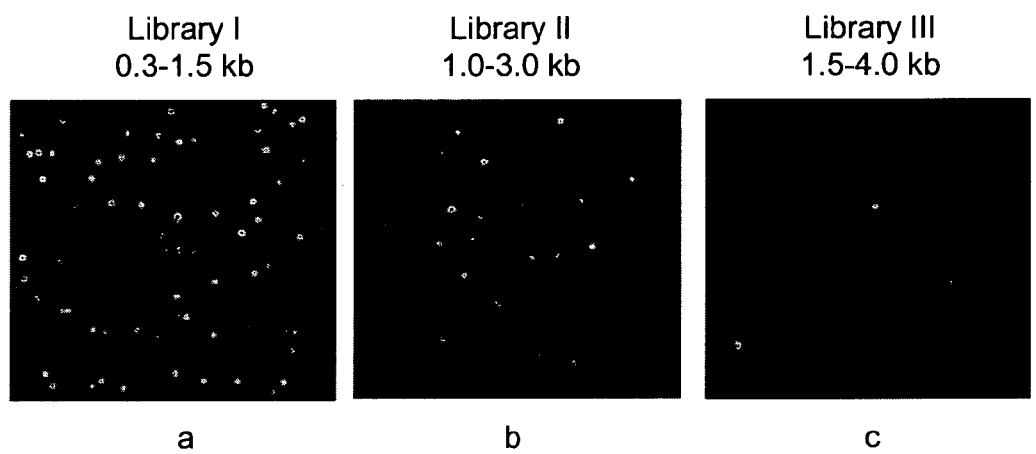
FIG. 22. In vivo solubility screening using split-GFP. Images showing cell colony fluorescence upon complementation of split GFP fragments for the three selected libraries: (a) Library I, (b) Library II, (c) Library III.

In Vivo Solubility Screen:

Pools of "in-frame" fragments were sub-cloned from the DHFR insertion vector, sized by agarose electrophoresis, and subcloned into the pTET-GFP 11 solubility vectors by restriction cloning using NdeI and BamHI sites. BL21 (DE3) expression libraries containing pET GFP (1-10) and pTET GFP 11 plasmids were subsequently screened for soluble expression using an in vivo split-GFP complementation assay. After transient induction of the tagged fragments, GFP 1-10 was induced to detect soluble proteins. All the libraries displayed a diversity of fluorescence phenotypes, forming a continuous distribution of fluorescence from very bright to essentially non fluorescent clones (FIG. 22). As expected, libraries with smaller fragments (see Library I, FIG. 20) contained a larger number of bright clones (FIG. 22a).

Figure 23:
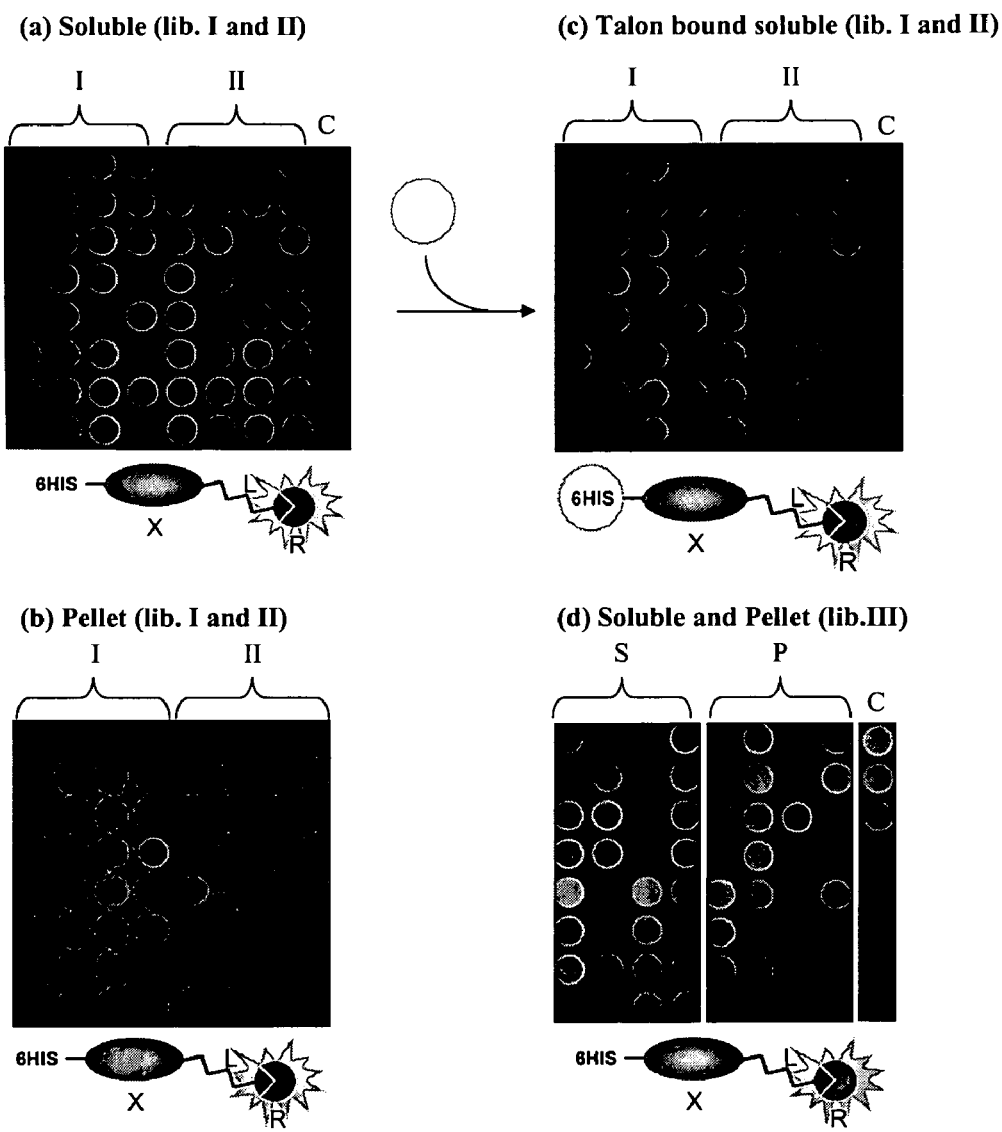
FIG. 23. In vitro complementation assay for 64 candidate soluble fragments isolated from in vivo solubility screen of libraries I and II. a) Fluorescence after complementation of the assayed soluble fraction in vitro. Column C corresponds to a serial dilution of a soluble standard protein. b) Fluorescence obtained after complementation of urea solubilized pellets. c) Fluorescence of Talon resin-bound complemented soluble fraction. d) Soluble and pellet fluorescence from in vitro complementation assay of library III clones.

The in vivo solubility screening provides information on soluble expression, but does not indicate the fraction of the protein expressed in the soluble phase. Clones producing highly expressed but poorly soluble proteins could potentially appear as bright as clones bearing weakly expressed but mostly soluble proteins. From each library, 8 bright, 8 moderately bright, 8 medium bright, and 8 faint clones were picked and maintained as freezer stocks for subsequent in vitro solubility screening a In Vitro Solubility Assay and Expression Quantification:

To determine soluble and total expression in vitro, the same clones were grown in liquid culture for expression of the GFP 11 tagged protein fusions for assay in vitro. Candidate optima from libraiies I and II were grown and induced at 27° C. first because they seemed to contain more soluble clones than library III (FIG. 22). After cell fractionation, both soluble and pellet fractions were quantified in vitro by complementation with an excess of purified GFP 1-10. For library I and II, most of the candidates were largely soluble as expected, consistent with the in vivo screen (FIG. 23a) very few had significant pellet fraction (FIG. 23b). Calibration with a soluble control protein allowed the estimation of the total number of moles of each protein sample (soluble and pellet) (Table 1). Library III was processed the same way but later on. As expected from the in vivo assay, it showed more fluorescence in the pellet fraction (FIG. 23d). A different calibration (FIG. 23d) was used to calculate the protein content (Table 1).

TABLE I

Summary worksheet for first 48 of 96 clones picked using in vivo split-GFP solubility screen.

| | Index | C:R | Frag size bp | Start Amino Acid | Stop Amino Acid | Size Amino Acids | Soluble Fs | Soluble mg/l | Pellet Fp | Pellet mg/l | Total mg/l | % soluble |
|---|---|---|---|---|---|---|---|---|---|---|---|---|
| Library I | 1 | A1 | 1442 | 1213 | 1694 | 482 | 1372 | 0.4 | 326 | 0.2 | 0.6 | 67 |
| | 2 | B1 | 432 | 1069 | 1213 | 145 | 36682 | 9.2 | 120 | 0.1 | 9.3 | 99 |
| | 3 | C1 | 559 | 1284 | 1470 | 187 | 41278 | 18.5 | 40 | 0.0 | 18.5 | 100 |
| | 4 | D1 | 521 | 1299 | 1472 | 174 | 3597 | 1.0 | 946 | 0.6 | 1.6 | 65 |
| | 5 | E1 | 713 | 1213 | 1450 | 238 | 29413 | 7.4 | 176 | 0.1 | 7.5 | 99 |
| | 6 | F1 | 841 | 1080 | 1360 | 281 | 50565 | 12.7 | 236 | 0.1 | 12.9 | 99 |
| | 7 | G1 | 805 | 1204 | 1472 | 269 | 38532 | 11.2 | −20 | 0.0 | 11.2 | 100 |
| | 8 | H1 | 712 | 1213 | 1450 | 238 | 31900 | 9.2 | −82 | 0.0 | 9.2 | 100 |
| | 9 | A2 | 317 | 1 | 107 | 107 | 38092 | 3.7 | −52 | 0.0 | 3.7 | 100 |
| | 10 | B2 | 853 | 1080 | 1364 | 285 | 29724 | 8.0 | −26 | 0.0 | 8.0 | 100 |
| | 11 | C2 | 841 | 1080 | 1360 | 281 | 27286 | 7.9 | 84 | 0.1 | 8.0 | 99 |
| | 12 | D2 | 529 | 1047 | 1223 | 177 | 44904 | 7.6 | 90 | 0.0 | 7.6 | 100 |
| | 13 | E2 | 487 | 1220 | 1382 | 163 | 33347 | 8.4 | −20 | 0.0 | 8.4 | 100 |
| | 14 | F2 | 710 | 633 | 870 | 238 | 23309 | 6.5 | 854 | 0.5 | 7.0 | 93 |
| | 15 | G2 | 373 | 1 | 125 | 125 | 25830 | 3.8 | 102 | 0.0 | 3.9 | 99 |
| | 16 | H2 | 663 | 619 | 840 | 222 | 23514 | 6.1 | 560 | 0.3 | 6.4 | 95 |

TABLE I-continued

Summary worksheet for first 48 of 96 clones picked using in vivo split-GFP solubility screen.

|  | Index | C:R | Frag size bp | Start Amino Acid | Stop Amino Acid | Size Amino Acids | Soluble Fs | Soluble mg/l | Pellet Fp | Pellet mg/l | Total mg/l | % soluble |
|---|---|---|---|---|---|---|---|---|---|---|---|---|
| Library I | 17 | A3 | 925 | 1423 | 1731 | 309 | 46286 | 13.0 | 4 | 0.0 | 13.0 | 100 |
|  | 18 | B3 | 559 | 1020 | 1206 | 187 | 27285 | 7.1 | 2166 | 1.1 | 8.3 | 86 |
|  | 19 | C3 | 721 | 1204 | 1444 | 241 | 35053 | 9.5 | 396 | 0.2 | 9.7 | 98 |
|  | 20 | D3 | 547 | 1049 | 1231 | 183 | 34534 | 9.0 | 2636 | 1.4 | 10.4 | 87 |
|  | 21 | E3 | 802 | 1033 | 1300 | 268 | 9197 | 2.6 | 4376 | 2.5 | 5.0 | 51 |
|  | 22 | F3 | 737 | 1204 | 1450 | 247 | 23235 | 3.9 | 420 | 0.1 | 4.1 | 96 |
|  | 23 | G3 | 685 | 1406 | 1634 | 229 | 32867 | 8.6 | −34 | 0.0 | 8.6 | 100 |
|  | 24 | H3 | 712 | 1145 | 1382 | 238 | 37021 | 11.1 | 212 | 0.1 | 11.2 | 99 |
|  | 25 | A4 | 261 | 1047 | 1134 | 88 | 39032 | 10.6 | 1762 | 1.0 | 11.5 | 92 |
|  | 26 | B4 | 280 | 3 | 96 | 94 | 33352 | 4.3 | −64 | 0.0 | 4.3 | 100 |
|  | 27 | C4 | 841 | 1080 | 1360 | 281 | 28586 | 8.6 | 72 | 0.1 | 8.6 | 99 |
|  | 28 | D4 | 582 | 941 | 1135 | 195 | 8877 | 2.5 | 15996 | 9.0 | 11.4 | 22 |
|  | 29 | E4 | 288 | 1 | 96 | 96 | 36517 | 4.7 | 188 | 0.1 | 4.8 | 99 |
|  | 30 | F4 | 556 | 945 | 1130 | 186 | 8987 | 2.5 | 3214 | 1.8 | 4.3 | 58 |
|  | 31 | G4 | 313 | 3 | 107 | 105 | 25283 | 4.3 | −52 | 0.0 | 4.2 | 100 |
|  | 32 | H4 | 937 | 493 | 805 | 313 | 6661 | 1.9 | 3744 | 2.2 | 4.1 | 47 |
| Library II | 33 | A5 | 907 | 1145 | 1447 | 303 | 30004 | 8.4 | 498 | 0.3 | 8.7 | 97 |
|  | 34 | B5 | 916 | 1020 | 1325 | 306 | 32858 | 9.5 | 1182 | 0.7 | 10.2 | 93 |
|  | 35 | C5 | 1698 | 1154 | 1720 | 567 | 29282 | 17.1 | 1358 | 1.6 | 18.7 | 91 |
|  | 36 | D5 | 1042 | 1384 | 1731 | 348 | 44882 | 13.0 | 248 | 0.2 | 13.1 | 99 |
|  | 37 | E5 | 739 | 1204 | 1450 | 247 | 37159 | 11.1 | 8214 | 4.9 | 16.1 | 69 |
|  | 38 | F5 | 993 | 1402 | 1733 | 332 | 33066 | 14.8 | −32 | 0.0 | 14.8 | 100 |
|  | 39 | G5 | 421 | 1072 | 1212 | 141 | 40698 | 6.0 | 406 | 0.1 | 6.2 | 98 |
|  | 40 | H5 | 739 | 1204 | 1450 | 247 | 41269 | 11.2 | 700 | 0.4 | 11.5 | 97 |
|  | 41 | A6 | 907 | 1145 | 1447 | 303 | 27123 | 7.6 | 108 | 0.1 | 7.7 | 99 |
|  | 42 | B6 | 1158 | 1 | 386 | 386 | 21393 | 7.9 | 528 | 0.4 | 8.3 | 95 |
|  | 43 | C6 | 862 | 1051 | 1338 | 288 | 40881 | 12.2 | −58 | 0.0 | 12.2 | 100 |
|  | 44 | D6 | 1069 | 866 | 1222 | 357 | 21087 | 9.4 | 3410 | 3.1 | 12.5 | 75 |
|  | 45 | E6 | 1400 | 740 | 1207 | 468 | 14337 | 7.8 | 998 | 1.1 | 8.9 | 88 |
|  | 46 | F6 | 766 | 1069 | 1324 | 256 | 17935 | 5.0 | 52 | 0.0 | 5.1 | 99 |
|  | 47 | G6 | 787 | 1063 | 1325 | 263 | 26596 | 7.2 | 22 | 0.0 | 7.2 | 100 |
|  | 48 | H6 | 825 | 1171 | 1446 | 276 | 18448 | 5.3 | −44 | 0.0 | 5.3 | 100 |
| Library II | 49 | A7 | 0 | 0 | 0 | 0 | 1155 | 0.0 | 15 | 0.0 | −0.1 | N/A |
|  | 50 | B7 | 1042 | 1384 | 1731 | 348 | 40152 | 15.8 | 1158 | 0.9 | 16.7 | 94 |
|  | 51 | C7 | 612 | 0 | 204 | 205 | 14431 | 5.3 | 72 | 0.1 | 5.4 | 99 |
|  | 52 | D7 | 0 | 0 | 0 | 0 | 1186 | 0.0 | 15 | 0.0 | −0.1 | N/A |
|  | 53 | E7 | 1527 | 941 | 1450 | 510 | 27988 | 17.2 | 396 | 0.5 | 17.7 | 97 |
|  | 54 | F7 | 863 | 1444 | 1731 | 288 | 45416 | 14.3 | 8 | 0.0 | 14.3 | 100 |
|  | 55 | G7 | 742 | 1203 | 1450 | 248 | 41272 | 10.1 | 16 | 0.0 | 10.1 | 100 |
|  | 56 | H7 | 1097 | 997 | 1362 | 366 | 44113 | 18.9 | 268 | 0.2 | 19.2 | 99 |
|  | 57 | A8 | 435 | 1042 | 1187 | 146 | 41876 | 9.3 | 1098 | 0.5 | 9.8 | 95 |
|  | 58 | B8 | 403 | 1042 | 1176 | 135 | 31299 | 6.1 | 1872 | 0.7 | 6.9 | 89 |
|  | 59 | C8 | 954 | 1045 | 1363 | 319 | 42026 | 15.4 | 860 | 0.6 | 16.1 | 96 |
|  | 60 | D8 | 905 | 1146 | 1447 | 302 | 24530 | 9.8 | 2470 | 2.0 | 11.8 | 83 |
|  | 61 | E8 | 1090 | 1020 | 1383 | 364 | 35397 | 18.4 | 188 | 0.2 | 18.7 | 99 |
|  | 62 | F8 | 907 | 1145 | 1447 | 303 | 26434 | 9.7 | 162 | 0.1 | 9.8 | 99 |
|  | 63 | G8 | 792 | 1076 | 1340 | 265 | 24889 | 7.3 | 504 | 0.3 | 7.6 | 96 |
|  | 64 | H8 | 1031 | 1104 | 1447 | 344 | 32070 | 13.0 | 706 | 0.6 | 13.6 | 96 |
| Library III | 65 | A9 | 1131 | 1020 | 1397 | 378 | 20971 | 13.2 | 30462 | 19.2 | 32.4 | 41 |
|  | 66 | B9 | 1499 | 945 | 1445 | 501 | 10736 | 6.8 | 3952 | 2.5 | 9.3 | 73 |
|  | 67 | C9 | 430 | 1033 | 1176 | 144 | 36359 | 22.9 | 53022 | 33.3 | 56.2 | 41 |
|  | 68 | D9 | 1010 | 1204 | 1541 | 338 | 64948 | 40.8 | 9080 | 5.8 | 46.6 | 88 |
|  | 69 | E9 | 264 | 1084 | 1172 | 89 | 82206 | 51.7 | 3836 | 2.5 | 54.1 | 95 |
|  | 70 | F9 | 1231 | 218 | 628 | 411 | 37475 | 23.6 | 8624 | 5.5 | 29.1 | 81 |
|  | 71 | G9 | 412 | 1033 | 1170 | 138 | 63795 | 40.1 | 18418 | 11.6 | 51.7 | 78 |
|  | 72 | H9 | 731 | 932 | 1175 | 244 | 1415 | 0.9 | 1958 | 1.3 | 2.2 | 42 |
|  | 73 | A10 | 613 | 599 | 803 | 205 | 11587 | 7.3 | 30772 | 19.4 | 26.7 | 27 |
|  | 74 | B10 | 328 | 1423 | 1532 | 110 | 28668 | 18.1 | 88490 | 55.6 | 73.7 | 25 |
|  | 75 | C10 | 538 | 1278 | 1457 | 180 | 91014 | 57.2 | 17814 | 11.2 | 68.4 | 84 |
|  | 76 | D10 | 460 | 1304 | 1457 | 154 | 59113 | 37.2 | 14042 | 8.9 | 46.1 | 81 |
|  | 77 | E10 | 502 | 1375 | 1542 | 168 | 10937 | 6.9 | 29656 | 18.7 | 25.6 | 27 |
|  | 78 | F10 | 536 | 925 | 1103 | 179 | 8541 | 5.4 | 16692 | 10.5 | 16.0 | 34 |
|  | 79 | G10 | 328 | 1067 | 1176 | 110 | 28406 | 17.9 | 3086 | 2.0 | 19.9 | 90 |
|  | 80 | H10 | 334 | 163 | 274 | 112 | 2377 | 1.6 | 8202 | 5.2 | 6.8 | 23 |

TABLE I-continued

Summary worksheet for first 48 of 96 clones picked using in vivo split-GFP solubility screen.

| | Index | C:R | Frag size bp | Start Amino Acid | Stop Amino Acid | Size Amino Acids | Soluble Fs | Soluble mg/l | Pellet Fp | Pellet mg/l | Total mg/l | % soluble |
|---|---|---|---|---|---|---|---|---|---|---|---|---|
| | *81 | A11 | 550 | N/A | N/A | 180 | 4345 | 2.0 | 8232 | 3.7 | 5.7 | 35 |
| | 82 | B11 | 185 | 1383 | 1445 | 63 | 4882 | 2.2 | 2026 | 1.0 | 3.2 | 70 |
| | 83 | C11 | 1132 | 1020 | 1397 | 378 | 4463 | 2.0 | 25610 | 11.5 | 13.6 | 15 |
| | 84 | D11 | 1383 | 984 | 1445 | 462 | 3786 | 1.7 | 7402 | 3.4 | 5.1 | 34 |
| | 85 | E11 | 1099 | 1078 | 1444 | 367 | 45578 | 20.5 | 1750 | 0.8 | 21.3 | 96 |
| | 86 | F11 | 380 | 1318 | 1445 | 128 | 44300 | 19.9 | 14274 | 6.4 | 26.4 | 76 |
| | 87 | G11 | 613 | 1017 | 1221 | 205 | 26687 | 12.0 | 5668 | 2.6 | 14.6 | 82 |
| Library III | 88 | H11 | 397 | 1042 | 1174 | 133 | 38748 | 17.4 | 13986 | 6.3 | 23.7 | 73 |
| | 89 | A12 | 538 | 1278 | 1457 | 180 | 70038 | 31.5 | 6676 | 3.0 | 34.5 | 91 |
| | 90 | B12 | 352 | 1340 | 1457 | 118 | 31262 | 14.1 | 8482 | 3.8 | 17.9 | 79 |
| | 91 | C12 | 385 | 1064 | 1192 | 129 | 29919 | 13.5 | 22300 | 10.0 | 23.5 | 57 |
| | 92 | D12 | 346 | 1355 | 1470 | 116 | 40130 | 18.0 | 2696 | 1.3 | 19.3 | 94 |
| | 93 | E12 | 316 | 1361 | 1466 | 106 | 19973 | 9.0 | 2458 | 1.1 | 10.1 | 89 |
| | 94 | F12 | 451 | 1183 | 1333 | 151 | 12841 | 5.8 | 1182 | 0.6 | 6.4 | 91 |
| | 95 | G12 | 400 | 3 | 136 | 134 | 24969 | 11.2 | 2972 | 1.4 | 12.6 | 89 |
| | 96 | H12 | 487 | 1267 | 1429 | 163 | 31314 | 14.1 | 5242 | 2.4 | 16.5 | 85 |

Unsorted fragments ("Sequencing", left) showing number of fragment (Index); column/row index (C:R); the size of fragment in nucleotides (frag size bp); amino acid position of fragment in gene starting amino acid number (start amino acid); ending amino acid number (end amino acid); size of fragment in amino acids (size amino acids).
Raw data for solubility calculation ("Split-GFP assay", right) indicate the fluorescence after in vitro complementation of the soluble (Soluble Fs) and pellet fractions (Pellet Fp), with the corresponding protein concentration of the soluble (Soluble mg/l) and pellet fractions (Pellet mg/l), and total protein expression (Total mg/l) calculated using a standard calibration (see supplementary information, Chapter VIII). Pellet assay sample volume 10 μl, soluble assay sample volume20 μl.
*For sample 81, index A11, sequencing failure precluded position determination. Only for sample A11, the insert fragment size (bp DNA) was estimated by size of PCR amplicon (agarose gel), and the corresponding amino acid length extimated by dividing bp by 3. The heavy strait line indicates that the data below come from separate experiment and analysis.

Binding of the Complemented Soluble Fraction by Talon 6HIS Affinity Resin:

The complemented soluble samples (soluble GFP 11+GFP 1-10) of library I and II were tested for metal affinity resin binding via the N-terminal 6HIS tag. Talon beads (Clontech) were added to the soluble assay plate and incubated (See scheme FIG. 23c). After two washes, the fluorescence of the Talon-bound fraction was proportional to the soluble complementation assay, demonstrating that all clones expressed fragments with intact termini and were thus full-length (N-terminal 6HIS, C-terminal GFP 11) (FIG. 24). However, some fragments from library III showed a different behavior, and didn't bind tightly to cobalt beads (FIG. 24, lower graph). These fragments are more likely to be aggregated after complementation.

Figure 25:
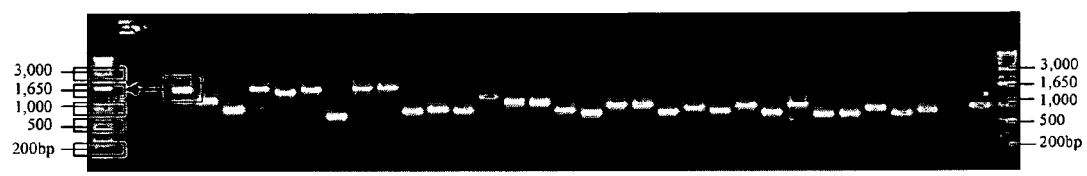
FIG. 25. Analytical agarose gel of PCR amplified inserts (example for library II). The average size of the fragments was evaluated by comparison to standard DNA ladders.

Characterization of the Fragments: Estimation of the Size of the Fragment by Single Colony PCR:

Single-colony PCR was performed on cell frozen stocks of all 96 clones picked during the in vivo split-GFP assay in order to estimate insert size. Unique primers specific to the pTET plasmid flanking the insert (tet promoter upstream and downstream plasmid terminator sequence) insured specific amplification of the fragments from the pTET plasmid, even though the cells also contained the pET GFP 1-10 plasmid. The reactions were visualized by agarose electrophoresis and the size of the PCR products were estimated by blob analysis relative to a calibrated set of molecular weight standards (FIG. 25). The size of each fragment was tabulated along with the fluorescence data from the in vitro solubility assay, the approximate mg/l of total expressed protein, and the fraction soluble (See Table I).

Characterization of the Fragments: DNA Sequencing of the Fragments and Ranking by Size and Solubility:

Sequences of the 96 clones were determined from individual PCR samples by the Plant-Microbe Genomics Facility (Ohio State University, USA). Multiple sequence alignment analysis with the pks13 gene was performed using BIO-EDIT® software. Both forward and reverse strand sequence information were used to determine exact boundaries of the fragments (Table I).

Figure 26:
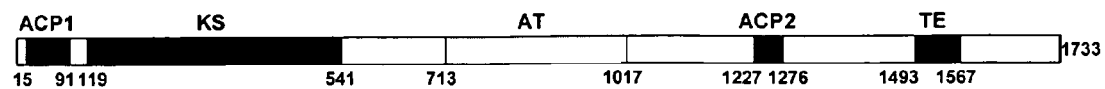
FIG. 26. Map of soluble domains of the pks13 gene selected by the "domain trapping" method. The identity of selected subcloned domains is indicated next to the corresponding fragment.
Figure 26:
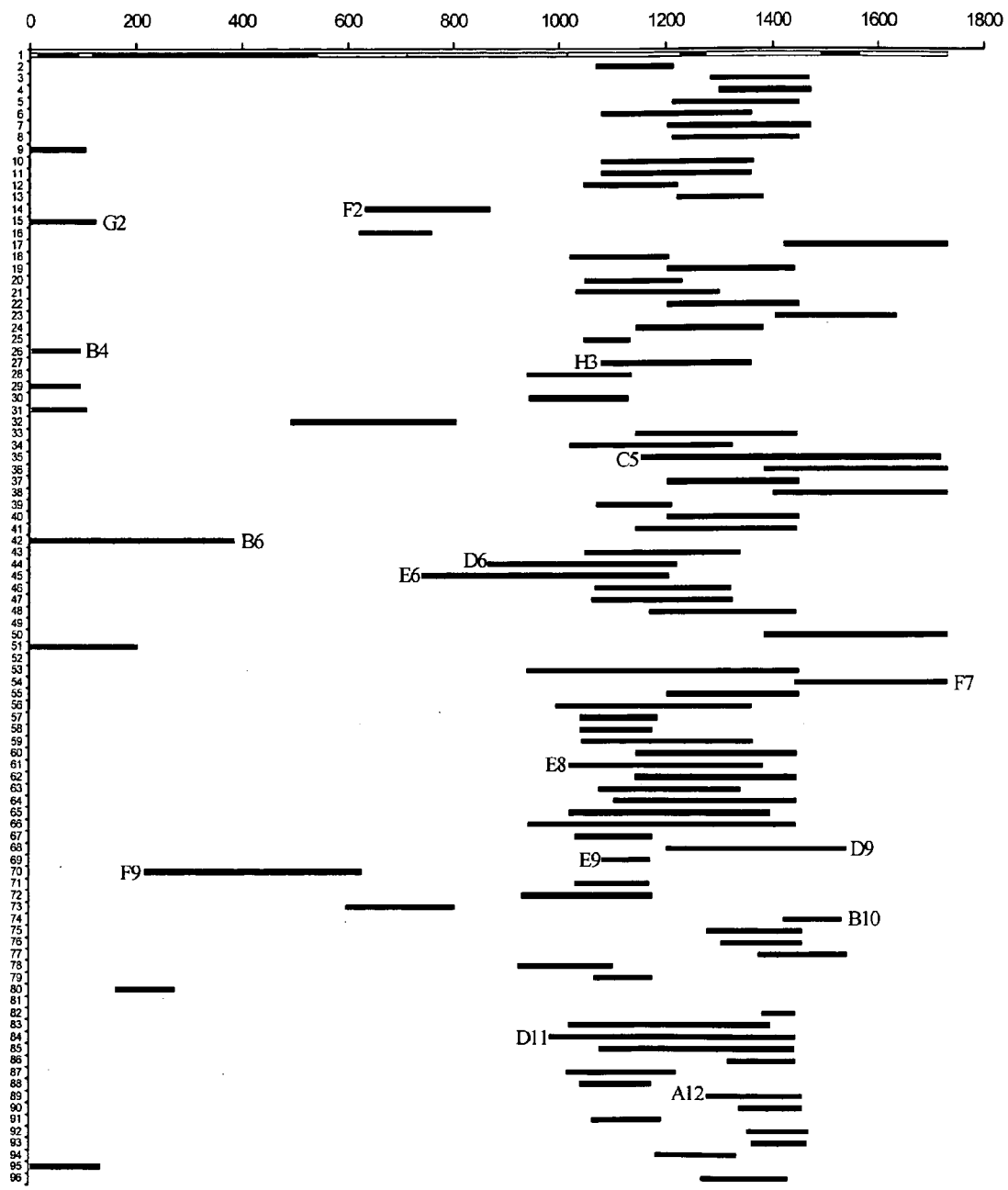

Characterization of the Fragments: Mapping the Fragments on Pks13:

Based on sequencing information, the boundaries of the different fragments were mapped onto the Pks13 sequence compared with the domain organization of the full length protein. All Pks13 domains are covered by one or more of the fragments (FIG. 26). A large fraction of these domains originated from the C-terminal part of the gene (FIG. 26). All the sequenced domains were in the authentic reading frame.

Subcloning into High Level Expression Vectors and Solubility Tests:

To compare the small scale expression in vitro screens with large scale over expression, eighteen soluble fragments were selected among the 96 sequenced clones, and subcloned from the PTET vectors into a pET an expression vector without the GFP 11 tag. The solubility of the subcloned domains were then be compared to the solubility determined using the in vitro split GFP. One receiving vector consisted of a pET T7 expression vector, bearing a N-terminal histidine tag (N6HIS-pET). A second receiving vector was an N6HIS pTET construct with no C-terminal GFP 11. This allowed us to explore differences in solubility due to expression level (T7 promoter is stronger than Tet promoter) and the influence of the GFP 11 tag. The constructs were induced at 27° C. for five hours. After culture, the soluble fraction and pellet fraction were isolated by sonication and centrifugation, and analyzed by SDS-PAGE densitometry (FIGS. 27 & 28).

The solubility of each of the 18 test fragments in the original pTET vector (N6HIS+C-terminal GFP 11) was compared with the subcloned N6HIS pET and N6HIS PTET constructs (Table II). Subcloned fragments were well-expressed in both pTET and pET (FIGS. 27 & 28). In the pET system, three fragments were mostly insoluble (F2, E6, D6), one was partially soluble (A11), while the other fourteen fragments were mostly soluble. As expected, expression levels of the pTET system were slightly lower than in the pET system for the same corresponding fragment. In the case of the pTET expression, most fragments were soluble. Fragments E6 and D6, insoluble expressed from pET, were ca. 50% soluble expressed from pTET (FIG. 28, Table II), consistent with the reduced expression rate of pTET relative to pET.

TABLE II

Expression and solubility at 27° C. of 18 Pks13 domains expressed in original N6HIS pTET GFP 11 pTET vector, or subcloned into pET and pTET vectors.

| | | N6HIS-pTET GFP11 in vitro assay | | N6HIS-pTET | | N6HIS-pET | |
|---|---|---|---|---|---|---|---|
| # | Plate RC Stock | total expression [a](mg/l) | % solubility | total expression [b](TQ) | % solubility | total expression [b](TQ) | % solubility |
| 1 | B6 | 8.3 | 95 | 0.60 | 90 | 1.60 | 95 |
| 2 | F9 | 29.1 | 80 | 0.20 | 90 | 2.76 | 75 |
| 3 | F2 | 7.0 | 90 | undet | undet | 3.4 | 22 |
| 4 | E6 | 8.9 | 90 | 0.63 | 50 | 3.93 | 15 |
| 5 | D6 | 12.5 | 75 | 0.52 | 25 | 3.34 | 15 |
| 6 | D11 | 5.1 | 35 | 0.74 | 20 | undet | undet |
| 7 | C5 | 18.7 | 90 | 0.25 | 90 | 1.55 | 80 |
| 8 | F7 | 14.3 | 100 | 0.52 | 100 | 2.18 | 90 |
| 9 | G2 | 3.9 | 100 | undet | 100 | 3.24 | 90 |
| 10 | B4 | 4.3 | 100 | undet | 100 | 3.28 | 90 |
| 11 | A12 | 34.5 | 90 | 0.52 | 85 | 0.93 | 95 |
| 12 | E9 | 54.1 | 95 | 0.30 | 90 | 0.88 | 80 |
| 13 | E8 | 18.7 | 100 | 0.80 | 90 | 1.62 | 75 |
| 14 | D9 | 46.6 | 90 | 0.63 | 90 | 0.88 | 90 |
| 15 | H12 | 16.5 | 85 | 0.36 | 76 | undet | undet |
| 16 | A11 | 5.7 | 35 | 1.03 | 65 | 1.08 | 75 |
| 17 | B10 | 73.7 | 25 | 0.28 | 90 | 1.20 | 90 |
| 18 | H3 | 11.1 | 100 | 0.55 | 75 | 0.52 | 100 |

[a]Total expression calculated from split GFP in vitro assay using soluble sulfite reductase-GFP 11 of known concentration.
[b]A trace quantity (TQ) of 1.0 in SDS-PAGE corresponds to ca. 10 mg/l expression.

In general, fragment solubility in the source N6HIS-X-GFP 11 pTET vector is similar to the solubility of the same fragment subcloned into either of the "destination" N6HIS vectors without a C-terminal GFP 11 tag. In some cases, the solubility decreased slightly when the fragment was subcloned. For example, fragment E8 (Table II) was fully soluble in the GFP 11 PTET vector, 90% soluble in the N6HIS pTET, and 75% soluble expressed from N6HIS pET expression. This effect is likely to come from the expression rates or expression levels, which are generally doubled in the pET expression relative to PTET. Interestingly, in some cases, the same fragment expressed from the N6HIS-X-GFP 11 pTET was more soluble that when expressed from the N6HIS PTET vector without the C-terminal tag. For instance, fragment D6 was 75% soluble with the GFP 11 tag and 25% soluble in PTET without GFP11 (Table II). C-terminal peptide extensions have been reported to increase protein solubility (Sati, Singh et al. 2002).

Large Scale Expression of a Selected Subset of Domains for Purification:

The bioinformatics-predicted boundaries of Pks13 were utilized to select a subset of the soluble domains for large-scale purification. The identity of each chosen domain and its boundaries are shown in Table III. Most of the functional regions of the Pks13 protein were represented in the soluble domain map (FIG. 26). Some AT partial domains could only be solubly expressed from pTET, while all other domains were solubly expressed from both pTET and pET.

TABLE III

Summary table of subcloned domains boundaries and solubility data from N6HIS-pET and N6HIS-pTET vectors 27° C. expressions.

| # | Domains | Plate RC Stock | First residue | Last residue | Number of residues | % Soluble N6HIS-pTET | % Soluble N6HIS-pET | Selected for large-scale production |
|---|---|---|---|---|---|---|---|---|
| 1 | ACP1-KSn | B6 | 1 | 386 | 386 | 90 | 100 | x |
| 2 | KSc | F9 | 218 | 628 | 410 | 90 | 75 | x |
| 3 | ATn | F2 | 633 | 870 | 237 | undet | 25 | |
| 4 | ATc | E6 | 740 | 1207 | 467 | 50 | 15 | x |
| 5 | ATc | D6 | 866 | 1222 | 356 | 26 | 16 | |
| 6 | ATc-ACP2 | D11 | 984 | 1445 | 461 | 20 | undet | |

TABLE III-continued

Summary table of subcloned domains boundaries and solubility data from N6HIS-pET and N6HIS-pTET vectors 27° C. expressions.

| # | Domains | Plate RC Stock | First residue | Last residue | Number of residues | % Soluble N6HIS-pTET | % Soluble N6HIS-pET | Selected for large-scale production |
|---|---|---|---|---|---|---|---|---|
| 7 | ACP2-TE | C5 | 1154 | 1720 | 566 | 90 | 80 | x |
| 8 | TE | F7 | 1444 | 1731 | 288 | 100 | 90 | x |
| 9 | ACP1 | G2 | 1 | 125 | 125 | 100 | 90 | x |
| 10 | ACP1 | B4 | 3 | 96 | 93 | 100 | 90 | x |
| 11 | Linker AT/ACp2 | A12 | 1278 | 1457 | 179 | 90 | 95 | |
| 12 | Linker AT/ACp2 | E9 | 1084 | 1172 | 88 | 90 | 80 | |
| 13 | junction AT/ACP2 | E8 | 1020 | 1383 | 363 | 90 | 75 | x |
| 14 | ACP2 | D9 | 1204 | 1541 | 337 | 95 | 90 | x |
| 15 | ACP2 | H12 | 1267 | 1429 | 162 | 75 | undet | |
| [a]16 | linker AT/ACp2 | A11 | ND | ND | ND | 65 | 75 | |
| 17 | ACP2 | B10 | 1423 | 1532 | 109 | 90 | 90 | x |
| 18 | ACP2 | H3 | 1145 | 1382 | 237 | 80 | 100 | |

An "x" in the column headed "Selected for large scale production" indicates that a bioinformatic analysis shows the fragment encompasses the indicated predicted domain, and was chosen for large scale production in preparation for structural determination.

[a]Fragment #16, plate row/column index A11, poor sequencing data precluded determination of the boundaries of the fragment.

Three large fragments (B6, F9, and C5) were grown in 50 ml cultures and induced at 27° C. The soluble fraction was isolated and tested for binding on Talon beads. After several washes with starting buffer, partially purified proteins were eluted and analyzed by SDS-PAGE (FIG. 29). Two fragments B6 and C5 could be easily purified and yielded high amounts of >95% pure protein (FIG. 29 a,c). Even worse than our previous observations, the fragment F9 corresponding to the KSc domain did not bind Talon beads when solubly expressed without a C-terminal GFP 11 tag (FIG. 29 b). The binding of the fragment F9 expressed with a C-terminal GFP 11 tag and N-terminal 6HIS was again tested, and found to detectably bind Talon resin, suggesting partial accessibility of the N6HIS tag GFP 11 (FIG. 29 d). Since the fragment F9 was quantified as a mostly soluble using the split-GFP assay in accordance with the SDS-PAGE (FIG. 29 b), a C-terminal extension could be potentially more accessible. The KSc domain was therefore cloned in a pET vector bearing a polyhistidine tag at the C-terminal end of the domain. This fragment was not expressed suggesting that the N-terminal 6HIS must relieve translation initiation inhibition due to mRNA secondary structure (FIG. 21 d).

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE OF SEQUENCES

SEQ ID NO: 1
GFP folding reporter nucleotide sequence:
ATGAGCAAAGGAGAAGAACTTTTCACTGGAGTTGTCCCAATTCTTGTTGA
ATTAGATGGTGATGTTAATGGGCACAAATTTTCTGTCAGTGGAGAGGGTG
AAGGTGATGCTACATACGGAAAACTCACCCTTAAATTTATTTGCACTACT
GGAAAACTACCTGTTCCATGGCCAACACTTGTCACTACTCTGACCTATGG
TGTTCAATGCTTTTCCCGTTATCCGGATCACATGAAACGGCATGACTTTT
TCAAGAGTGCCATGCCCGAAGGTTATGTACAGGAACGCACTATATCTTTC
AAAGATGACGGGAACTACAAGACGCGTGCTGAAGTCAAGTTTGAAGGTGA
TACCCTTGTTAATCGTATCGAGTTAAAAGGTATTGATTTTAAAGAAGATG
GAAACATTCTCGGACACAAACTCGAGTACAACTATAACTCACACAATGTA
TACATCACGGCAGACAAACAAAAGAATGGAATCAAAGCTAACTTCAAAAT
TCGCCACAACGTTGAAGATGGTTCCGTTCAACTAGCAGACCATTATCAAC
AAAATACTCCAATTGGCGATGGCCCTGTCCTTTTACCAGACAACCATTAC
CTGTCGACACAATCTGCCCTTTCGAAAGATCCCAACGAAAGCGTGACCA
CATGGTCCTTCTTGAGTTTGTAACTGCTGCTGGGATTACACATGGCATGG
ATGAGCTCTACAAA SEQ ID NO: 2
GFP folding reporter amino acid sequence:
MSKGEELFTGVVPILVELDGDVNGHKFSVSGEGEGDATYGKLTLKFICTT
GKLPVPWPTLVTTLTYGVQCFSRYPDHMKRHDFFKSAMPEGYVQERTISF
KDDGNYKTRAEVKFEGDTLVNRIELKGIDFKEDGNILGHKLEYNYNSHNV
YITADKQKNGIKANFKIRHNIEDGSVQLADHYQQNTPIGDGPVLLPDNHY
LSTQSALSKDPNEKRDHMVLLEFVTAAGITHGMDELYK SEQ ID NO: 3
GFP superfolder nucleotide sequence:
ATGAGCAAAGGAGAAGAACTTTTCACTGGAGTTGTCCCAATTCTTGTTGA
ATTAGATGGTGATGTTAATGGGCACAAATTTTCTGTCCGTGGAGAGGGTG
AAGGTGATGCTACAAACGGAAAACTCACCCTTAAATTTATTTGCACTACT
GGAAAACTACCTGTTCCATGGCCAACACTTGTCACTACTCTGACCTATGG
TGTTCAATGCTTTTCCCGTTATCCGGATCACATGAAACGGCATGACTTTT
TCAAGAGTGCCATGCCCGAAGGTTATGTACAGGAACGCACTATATCTTTC
AAAGATGACGGGACCTACAAGACGCGTGCTGAAGTCAAGTTTGAAGGTGA
TACCCTTGTTAATCGTATCGAGTTAAAAGGTATTGATTTTAAAGAAGATG
GAAACATTCTCGGACACAAACTCGAGTACAACTTTAACTCACACAATGTA
TACATCACGGCAGACAAACAAAAGAATGGAATCAAAGCTAACTTCAAAAT
TCGCCACAACGTTGAAGATGGTTCCGTTCAACTAGCAGACCATTATCAAC
AAAATACTCCAATTGGCGATGGCCCTGTCCTTTTACCAGACAACCATTAC
CTGTCGACACAATCTGTCCTTTCGAAAGATCCCAACGAAAGCGTGACCA

TABLE OF SEQUENCES

CATGGTCCTTCTTGAGTTTGTAACTGCTGCTGGGATTACACATGGCATGG
ATGAGCTCTACAA

SEQ ID NO: 4:
GFP superfolder amino acid sequence:
MSKGEELFTGVVPILVELDGDVNGHKFSVRGEGEGDATNGKLTLKFICTT
GKLPVPWPTLVTTLTYGVQCFSRYPDHMKRHDFFKSAMPEGYVQERTISF
KDDGTYKTRAEVKFEGDTLVNRIELKGIDFKEDGNILGHKLEYNFNSHNV
YITADKQKNGIKANFKIRHNVEDGSVQLADHYQQNTPIGDGPVLLPDNHY
LSTQSVLSKDPNEKRDHMVLLEFVTAAGITHGMDELYK SEQ ID NO: 5:
Nucleotide GFPcp9/8_FR/FR v2:
ACCATGGGTGGCGGTACTAGCGGAGGCGGTAGCGCTAGTGATGGTTCCGT
TCAACTAGCAGACCATTATCAACAAAATACTCCAATTGGCGATGGCCCTG
TCCTTTTACCAGACAACCATTACCTGTCGACACAATCTGCCCTTTCGAAA
GATCCCAACGAAAGCGTGACCACATGGTCCTTCTTGAGTTTGTAACTGC
TGCTGGGATTACACATGGCATGGATGAACTCTACAAAGGCGGTGGGTCGG
GCGGGGGCTCCCATATGGGCGGTTCAGGATCCGGTGGAGGGTCAGGGGGC
GGATCAAGCAAAGGAGAAGAACTTTTCACTGGAGTTGTCCCAATTCTTGT
TGAATTAGATGGTGATGTTAATGGGCACAAATTTTCTGTCAGTGGAGAGG
GTGAAGGTGATGCTACATACGGAAAACTCACCCTTAAATTTATTTGCACT
ACTGGAAAACTACCTGTTCCATGGCCAACACTTGTCACTACTCTGACCTA
TGGTGTTCAATGCTTTTCCCGTTATCCGGATCACATGAAACGGCATGACT
TTTTCAAGAGTGCCATGCCCGAAGGTTATGTACAGGAACGCACTATATCT
TTCAAAGATGACGGGAACTACAAGACGCGTGCTGAAGTCAAGTTTGAAGG
TGATACCCTTGTTAATCGTATCGAGTTAAAGGGTATTGATTTTAAAGAAG
ATGGAAACATTCTCGGACACAAACTCGAGTACAACTATAACTCACACAAT
GTATACATCACGGCAGACAAACAAAGAATGGAATCAAAGCTAACTTCAA
AATTCGCCACAACATTGAAGATGGTACCTAA SEQ ID NO: 6:
GFPcp9/8_FR/FR amino acid sequence:
TMGGGTSGGGSASDGSVQLADHYQQNTPIGDGPVLLPDNHYLSTQSALSK
DPNEKRDHMVLLEFVTAAGITHGMDELYKGGGSGGGSHMGGSGSGGGSGG
GSSKGEELFTGVVPILVELDGDVNGHKFSVSGEGEGDATYGKLTLKFICT
TGKLPVPWPTLVTTLTYGVQCFSRYPDHMKRHDFFKSAMPEGYVQERTIS
FKDDGNYKTRAEVKFEGDTLVNRIELKGIDFKEDGNILGHKLEYNYNSHN
VYITADKQKNGIKANFKIRHNIEDGT*

SEQ ID NO: 7:
GFPcp9/8_SF/SF nucleotide sequence:
ACCATGGGTGGCGGTACTAGCGGAGGCGGTAGCGCTAGTGATGGTTCCGT
TCAACTAGCAGACCATTATCAACAAAATACTCCAATTGGCGATGGCCCTG
TCCTTTTACCAGACAACCATTACCTGTCGACACAATCTGTCCTTTCGAAA
GATCCCAACGAAAGCGTGACCACATGGTCCTTCTTGAGTTTGTAACTGC
TGCTGGGATTACACATGGCATGGATGAGCTCTACAAAGGCGGTGGGTCGG
GCGGGGGCTCCCATATGGGCGGTTCAGGATCCGGTGGAGGGTCAGGGGGC
GGATCAAGCAAAGGAGAAGAACTTTTCACTGGAGTTGTCCCAATTCTTGT
TGAATTAGATGGTGATGTTAATGGGCACAAATTTTCTGTCAGAGGAGAGG
GTGAAGGTGATGCTACAAACGGAAAACTCACCCTTAAATTTATTTGCACT
ACTGGAAAACTACCTGTTCCATGGCCAACACTTGTCACTACTCTGACCTA
TGGTGTTCAATGCTTTTCCCGTTATCCGGATCACATGAAACGGCATGACT
TTTTCAGGAGTGCCATGCCCGAAGGTTATGTACAGGAACGCACTATATCT
TTCAAAGATGACGGGAACTACAAGACGCGTGCTGAAGTCAAGTTTGAAGG
TGATACCCTTGTTAATCGTATCGAGTTAAAGGGTACTGATTTTAAAGAAG
ATGGAAACATTCTCGGACACAAACTCGAGTACAACTTTAACTCACACAAT
GTATACATCACGGCAGACAAACAAAGAATGGAATCAAAGCTAACTTCAA
AATTCGCCACAACGTTGAAGATGGTACCTAA SEQ ID NO: 8:
GFPcp9/8_SF/SF amino acid sequence:
TMGGGTSGGGSASDGSVQLADHYQQNTPIGDGPVLLPDNHYLSTQSVLSK
DPNEKRDHMVLLEFVTAAGITHGMDELYKGGGSGGGSHMGGSGSGGGSGG
GSSKGEELFTGVVPILVELDGDVNGHKFSVRGEGEGDATNGKLTLKFICT
TGKLPVPWPTLVTTLTYGVQCFSRYPDHMKRHDFFRSAMPEGYVQERTIS
FKDDGNYKTRAEVKFEGDTLVNRIELKGTDFKEDGNILGHKLEYNFNSHN
VYITADKQKNGIKANFKIRHNVEDGT*

SEQ ID NO: 9:
GFPcp9/8_FR/SF nucleotide sequence:
ACCATGGGTGGCGGTACTAGCGGAGGCGGTAGCGCTAGTGATGGTTCCGT
TCAACTAGCAGACCATTATCAACAAAATACTCCAATTGGCGATGGCCCTG
TCCTTTTACCAGACAACCATTACCTGTCGACACAATCTGCCCTTTCGAAA
GATCCCAACGAAAGCGTGACCACATGGTCCTTCTTGAGTTTGTAACTGC
TGCTGGGATTACACATGGCATGGATGAGCTCTACAAAGGCGGTGGGTCGG
GCGGGGGCTCCCATATGGGCGGTTCAGGATCCGGTGGAGGGTCAGGGGGC
GGATCAAGCAAAGGAGAAGAACTTTTCACTGGAGTTGTCCCAATTCTTGT
TGAATTAGATGGTGATGTTAATGGGCACAAATTTTCTGTCAGAGGAGAGG
GTGAAGGTGATGCTACAAACGGAAAACTCACCCTTAAATTTATTTGCACT
ACTGGAAAACTACCTGTTCCATGGCCAACACTTGTCACTACTCTGACCTA
TGGTGTTCAATGCTTTTCCCGTTATCCGGATCACATGAAACGGCATGACT
TTTTCAGGAGTGCCATGCCCGAAGGTTATGTACAGGAACGCACTATATCT
TTCAAAGATGACGGGAACTACAAGACGCGTGCTGAAGTCAAGTTTGAAGG
TGATACCCTTGTTAATCGTATCGAGTTAAAGGGTACTGATTTTAAAGAAG
ATGGAAACATTCTCGGACACAAACTCGAGTACAACTTTAACTCACACAAT
GTATACATCACGGCAGACAAACAAAGAATGGAATCAAAGCTAACTTCAA
AATTCGCCACAACGTTGAAGATGGTACCTAA SEQ ID NO: 10:
GFPcp9/8_FR/SF amino acid sequence:
TMGGGTSGGGSASDGSVQLADHYQQNTPIGDGPVLLPDNHYLSTQSALSK
DPNEKRDHMVLLEFVTAAGITHGMDELYKGGGSGGGLHMGGSGSGGGSGG
GSSKGEELFTGVVPILVELDGDVNGHKFSVRGEGEGDATNGKLTLKFICT
TGKLPVPWPTLVTTLTYGVQCFSRYPDHMKRHDFFRSAMPEGYVQERTIS
FKDDGNYKTRAEVKFEGDTLVNRIELKGIDFKEDGNILGHKLEYNFNSHN
VYITADKQKNGIKANFKIRHNVEDGT*

SEQ ID NO: 11:
GFPcp9/8_SF/FR nucleotide sequence:
ACCATGGGTGGCGGTACTAGCGGAGGCGGTAGCGCTAGTGATGGTTCCGT
TCAACTAGCAGACCATTATCAACAAAATACTCCAATTGGCGATGGCCCTG
TCCTTTTACCAGACAACCATTACCTGTCGACACAATCTGTCCTTTCGAAA
GATCCCAACGAAAGCGTGACCACATGGTCCTTCTTGAGTTTGTAACTGC
TGCTGGGATTACACATGCATGGATGAGCTCTACAAAGGCGGTGGGTCGG
GCGGGGGCTCCCATATGGGCGGTTCAGGATCCGGTGGAGGGTCAGGGGGC
GGATCAAGCAAAGGAGAAGAACTTTTCACTGGAGTTGTCCCAATTCTTGT
TGAATTAGATGGTGATGTTAATGGGCACAAATTTTCTGTCAGTGGAGAGG
GTGAAGGTGATGCTACATACGGAAAACTCACCCTTAAATTTATTTGCACT
ACTGGAAAACTACCTGTTCCATGGCCAACACTTGTCACTACTCTGACCTA
TGGTGTTCAATGCTTTTCCCGTTATCCGGATCACATGAAACGGCATGACT
TTTTCAAGAGTGCCATGCCCGAAGGTTATGTACAGGAACGCACTATATCT
TTCAAAGATGACGGGAACTACAAGACGCGTGCTGAAGTCAAGTTTGAAGG
TGATACCCTTGTTAATCGTATCGAGTTAAAGGGTATTGATTTTAAAGAGG
ATGGAAACATTCTCGGACACAAACTCGAGTACAACTATAACTCACACAAT
GTATACATCACGGCAGACAAACAAAGAATGGAATCAAAGCTAACTTCAA
AATTCGCCACAACATTGAAGATGGTACCTAA SEQ ID NO: 12:
GFPcp9/8_SF/FR nucleotide sequence:
TMGGGTSGGGSASDGSVQLADHYQQNTPIGDGPVLLPDNHYLSTQSVLSK
DPNEKRDHMVLLEFVTAAGITHGMDELYKGGGSGGGSHMGGSGSGGGSGG
GSSKGEELFTGVVPILVELDGDVNGHKFSVSGEGEGDATYGKLTLKFICT
TGKLPVPWPTLVTTLTYGVQCFSRYPDHMKRHDFFKSAMPEGYVQERTIS
FKDDGNYKTRAEVKFEGDTLVNRIELKGIDFKEDGNILGHKLEYNYNSHN
VYITADKQKNGIKANFKIRHNIEDGT*

SEQ ID NO: 13:
GFPcp8/7_FR/FR nucleotide sequence:
ACCATGGGTGGCGGTACTAGCGGAGGCGGTAGCGCTAGTCAAAAGAATGG
AATCAAAGCTAACTTCAAAATTCGCCACAACATTGAAGATGGTTCCGTTC
AACTAGCAGACCATTATCAACAAAATACTCCAATTGGCGATGGCCCTGTC
CTTTTACCAGACAACCATTACCTGTCGACACAATCTGCCCTTTCGAAGA
TCCCAACGAAAGCGTGACCACATGGTCCTTCTTGAGTTTGTAACTGCTG
CTGGGATTACACATGGCATGGATGAACTCTACAAAGGCGGTGGGTCGGGC
GGGGGCTCCCATATGGGCGGTTCAGGATCCGGTGGAGGGTCAGGGGGCGG
ATCAAGCAAAGGAGAAGAACTTTTCACTGGAGTTGTCCCAATTCTTGTTG
AATTAGATGGTGATGTTAATGGGCACAAATTTTCTGTCAGTGGAGAGGGT
GAAGGTGATGCTACATACGGAAAACTCACCCTTAAATTTATTTGCACTAC
TGGAAAACTACCTGTTCCATGGCCAACACTTGTCACTACTCTGACCTATG
GTGTTCAATGCTTTTCCCGTTATCCGGATCACATGAAACGGCATGACTTT
TTCAAGAGTGCCATGCCCGAAGGTTATGTACAGGAACGCACTATATCTTT
CAAAGATGACGGGAACTACAAGACGCGTGCTGAAGTCAAGTTTGAAGGTG
ATACCCTTGTTAATCGTATCGAGTTAAAGGGTATTGATTTTAAAGAGGAT
GGAAACATTCTCGGACACAAACTCGAGTACAACTATAACTCACACAATGT
ATACATCACGGCAGACAAACAAGGTACCTAA SEQ ID NO: 14:
GFPcp8/7_FR/FR amino acid sequence:
TMGGGTSGGGSASQKNGIKANFKIRHNIEDGSVQLADHYQQNTPIGDGPV
LLPDNHYLSTQSALSKDPNEKRDHMVLLEFVTAAGITHGMDELYKGGGSG
GGSHMGGSGSGGGSGGGSSKGEELFTGVVPILVELDGDVNGHKFSVSGEG
EGDATYGKLTLKFICTTGKLPVPWPTLVTTLTYGVQCFSRYPDHMKRHDF

TABLE OF SEQUENCES

FKSAMPEGYVQERTISFKDDGNYKTRAEVKFEGDTLVNRIELKGIDFKED
GNILGHKLEYNYNSHNVYITADKQGT*

SEQ ID NO: 15:
GFPcp8/7_SF/SF nucleotide sequence:
ACCATGGGTGGCGGTACTAGCGGAGGCGGTAGCGCTAGTCAAAAGAATGG
AATCAAAGCTAACTTCAAAATTCGCCACAACGTTGAAGATGGTTCCGTTC
AACTAGCAGACCATTATCAACAAAATACTCCAATTGGCGATGGCCCTGTC
CTTTTACCAGACAACCATTACCTGTCGACACAATCTGTCCTTTCGAAAGA
TCCCAACGAAAAGCGTGACCACATGGTCCTTCTTGAGTTTGTAACTGCTG
CTGGGATTACACATGGCATGGATGAGCTCTACAAAGGCGGTGGGTCGGGC
GGGGGCTCCCATATGGGCGGTTCAGGATCCGGTGGAGGGTCAGGGGGCGG
ATCAAGCAAAGGAGAAGAACTTTTCACTGGAGTTGTCCCAATTCTTGTTG
AATTAGATGGTGATGTTAATGGGCACAAATTTTCTGTCAGAGGAGAGGGT
GAAGGTGATGCTACAAACGGAAAACTCACCCTTAAATTTATTTGCACTAC
TGGAAAACTACCTGTTCCATGGCCAACACTTGTCACTACTCTGACCTATG
GTGTTCAATGCTTTTCCCGTTATCCGGATCACATGAAACGGCATGACTTT
TTCAAGAGTGCCATGCCCGAAGGTTATGTACAGGAACGCACTATATCTTT
CAAAGATGACGGGAACTACAAGACGCGTGCTGAAGTCAAGTTTGAAGGTG
ATACCCTTGTTAATCGTATCGAGTTAAAGGGTACTGATTTTAAAGAAGAT
GGAAACATTCTCGGACACAAACTCGAGTACAACTTTAACTCACACAATGT
ATACATCACGGCAGACAAACAAGGTACCTAA SEQ ID NO: 16:
GFPcp8/7_SF/SF amino acid sequence:
TMGGGTSGGGSASQKNGIKANFKIRHNVEDGSVQLADHYQQNTPIGDGPV
LLPDNHYLSTQSVLSKDPNEKRDHMVLLEFVTAAGITHGMDGLYKGGGSG
GGSHMGGSGSGGGSGGGSSKGEELFTGVVPILVELDGDVNGHKFSVRGEG
EGDATNGKLTLKFICTTGKLPVPWPTLVTTLTYGVQCFSRYPDHMKRHDF
FKSAMPEGYVQERTISFKDDGNYKTRAEVKFEGDTLVNRIELKGTDFKED
GNILGHKLEYNFNSHNVYITADKQGT*

SEQ ID NO: 17:
GFPcp8/7_FR/SF nucleotide sequence:
ACCATGGGTGGCGGTACTAGCGGAGGCGGTAGCGCTAGTCAAAAGAATGG
AATCAAAGCTAACTTCAAAATTCGCCACAACATTGAAGATGGTTCCGTTC
AACTAGCAGACCATTATCAACAAAATACTCCAATTGGCGATGGCCCTGTC
CTTTTACCAGACAACCATTACCTGTCGACACAATCTGCCCTTCGAAAGA
TCCCAACGAAAAGCGTGACCACATGGTCCTTCTTGAGTTTGTAACTGCTG
CTGGGATTACACATGGCATGGATGAGCTCTACAAAGGCGGTGGGTCGGGC
GGGGGCTCCCATATGGGCGGTTCAGGATCCGGTGGAGGGTCAGGGGGCGG
ATCAAGCAAAGGAGAAGAACTTTTCACTGGAGTTGTCCCAATTCTTGTTG
AATTAGATGGTGATGTTAATGGGCACAAATTTTCTGTCAGAGGAGAGGGT
GAAGGTGATGCTACAAACGGAAAACTCACCCTTAAATTTATTTGCACTAC
TGGAAAACTACCTGTTCCATGGCCAACACTTGTCACTACTCTGACCTATG
GTGTTCAATGCTTTTCCCGTTATCCGGATCACATGAAACGGCATGACTTT
TTCAAGAGTGCCATGCCCGAAGGTTATGTACAGGAACGCACTATATCTTT
CAAAGATGACGGGAACTACAAGACGCGTGCTGAAGTCAAGTTTGAAGGTG
ATACCCTTGTTAATCGTATCGAGTTAAAGGGTACTGATTTTAAAGAAAAT
GGAAaCATTCTCGGACACAAACTCGAGTACAACTTTAACTCACACAATGT
ATACATCACGGCAGACAAACAAGGTACCTAA SEQ ID NO: 18:
GFPcp8/7_FR/SF amino acid sequence:
TMGGGTSGGGSASQKNGIKANFKIRHNIEDGSVQLADHYQQNTPIGDGPV
LLPDNHYLSTQSALSKDPNEKRDHMVLLEFVTAAGITHGMDELYKGGGSG
GGSHMGGSGSGGGSGGGSSKGEELFTGVVPILVELDGDVNGHKFSVRGEG
EGDATNGKLTLKFICTTGKLPVPWPTLVTTLTYGVQCFSRYPDHMKRHDF
FKSAMPEGYVQERTISFKDDGNYKTRAEVKFEGDTLVNRIELKGTDFKEN
GNILGHKLEYNFNSHNVYITADKQGT*

SEQ ID NO: 19:
GFPcp8/7_SF/FR nucleotide sequence:
ACCATGGGTGGCGGTACTAGCGGAGGCGGTAGCGCTAGTCAAAAGAATGG
AATCAAAGCTAACTTCAAAATTCGCCACAACGTTGAAGATGGTTCCGTTC
AACTAGCAGACCATTATCAACAAAATACTCCAATTGGCGAAGGCCCTGTC
CTTTTACCAGACAACCATTACCTGTCGACACAATCTGTCCTTTCGAAAGA
TCCCAACGAAAAGCGTGACCACATGGTCCTTCTTGAGTTTGTAACTGCTG
CTGGGATTACACATGGCATGGATGAACTCTACAAAGGCGGTGGGTCGGGC
GGGGGCTCCCATATGGGCGGTTCAGGATCCGGTGGAGGGTCAGGGGGCGG
ATCAAGCAAAGGAGAAGAACTTTTCACTGGAGTTGTCCCAATTCTTGTTG
AATTAGATGGTGATGTTAATGGGCACAAATTTCTGTCAGTGGAGAGGGT
GAAGGTGATGCTACATACGGAAAACTCACCCTTAAATTTATTTGCACTAC
TGGAAAACTACCTGTTCCATGGCCAACACTTGTCACTACTCTGACCTATG
GTGTTCAATGCTTTTCCCGTTATCCGGATCACATGAAACGGCATGACTTT
TTCAAGAGTGCCATGCCCGAAGGTTATGTACAGGAACGCACTATATCTTT
CAAAGATGACGGGAACTACAAGACGCGTGCTGAAGTCAAGTTTGAAGGTG
ATACCCTTGTTAATCGTATCGAGTTAAAGGGTATTGATTTTAAAGAGGAT
GGAAACATTCTCGGACACAAACTCGAGTACAACTATAACTCACACAATGT
ATACATCACGGCAGACAAACAAGGTACCTAA SEQ ID NO: 20:
GFPcp8/7_SF/FR amino acid sequence:
TMGGGTSGGGSASQKNGIKANFKIRHNVEDGSVQLADHYQQNTPIGEGPV
LLPDNHYLSTQSVLSKDPNEKRDHMVLLEFVTAAGITHGMDELYKGGGSG
GGSHMGGSGSGGGSGGGSSKGEELFTGVVPILVELDGDVNGHKFSVSGEG
EGDATYGKLTLKFICTTGKLPVPWPTLVTTLTYGVQCFSRYPDHMKRHDF
FKSAMPEGYVQERTISFKDDGNYKTRAEVKFEGDTLVNRIELKGIDFKED
GNILGHKLEYNYNSHNVYITADKQGT*

SEQ ID NO: 21:
Nucleotide sequence of pET vector for accepting
the NcoI/KpnI circular permutant constructs:
TGGCGAATGGGACGCGCCCTGTAGCGGCGCATTAAGCGCGGCGGGTGTGG
TGGTTACGCGCAGCGTGACCGCTACACTTGCCAGCGCCCTAGCGCCCGCT
CCTTTCGCTTTCTTCCCTTCCTTTCTCGCCACGTTCGGCGGCTTTCCCCG
TCAAGCTCTAAATCGGGGGCTCCCTTTAGGGTTCCGATTTAGTGCTTTAC
GGCACCTCGACCCCAAAAAACTTGATTAGGGTGATGGTTCACGTAGTGGG
CCATCGCCCTGATAGACGGTTTTTCGCCCTTTGACGTTGGAGTCCACGTT
CTTTAATAGTGGACTCTTGTTCCAAACTGGAACAACACTCAACCCTATCT
CGGTCTATTCTTTTGATTTATAAGGGATTTTGCCGATTTCGGCCTATTGG
TTAAAAAATGAGCTGATTTAACAAAAATTTAACGCGAATTTTAACAAAAT
ATTAACGTTTACAATTTCAGGTGGCACTTTTCGGGGAAATGTGCGCGGAA
CCCCTATTTGTTTATTTTTCTAAATACATTCAAATATGTATCCGCTCATG
AATTAATTCTTAGAAAAACTCATCGAGCATCAAATGAAACTGCAATTTAT
TCATATCAGGATTATCAATACCATATTTTTGAAAAAGCCGTTTCTGTAAT
GAAGGAGAAAACTCACCGAGGCAGTTCCATAGGATGGCAAGATCCTGGTA
TCGGTCTGCGATTCCGACTCGTCCAACATCAATACAACCTATTAATTTCC
CCTCGTCAAAAATAAGGTTATCAAGTGAGAAATCACCATGAGTGACGACT
GAATCCGGTGAGAATGGCAAAAGTTTATGCATTTCTTTCCAGACTTGTTC
AACAGGCCAGCCATTACGCTCGTCATCAAAATCACTCGCATCAACCAAAC
CGTTATTCATTCGTGATTGCGCCTGAGCGAGACGAAATACGCGATCGCTG
TTAAAAGGACAATTACAAACAGGAATCGAATGCAACCGGCGCAGGAACAC
TGCCAGCGCATCAACAATATTTTCACCTGAATCAGGATATTCTTCTAATA
CCTGGAATGCTGTTTTCCCGGGGATCGCAGTGGTGAGTAACCATGCATCA
TCAGGAGTACGGATAAAATGCTTGATGGTCGGAAGAGGCATAAATTCCGT
CAGCCAGTTTAGTCTGACCATCTCATCTGTAACATCATTGGCAACGCTAC
CTTTGCCATGTTTCAGAAACAACTCTGGCGCATCGGGCTTCCCATACAAT
CGATAGATTGTCGCACCTGATTGCCCGACATTATCGCGAGCCCATTTATA
CCCATATAAATCAGCATCCATGTTGGAATTTAATCGCGGCCTAGAGCAAG
ACGTTTCCCGTTGAATATGGCTCATAACACCCCTTGTATTACTGTTTATG
TAAGCAGACAGTTTTATTGTTCATGACCAAAATCCCTTAACGTGAGTTTT
CGTTCCACTGAGCGTCAGACCCCGTAGAAAAGATCAAAGGATCTTCTTGA
GATCCTTTTTTTCTGCGCGTAATCTGCTGCTTGCAAACAAAAAAACCACC
GCTACCAGCGGTGGTTTGTTTGCCGGATCAAGAGCTACCAACTCTTTTTC
CGAAGGTAACTGGCTTCAGCAGAGCGCAGATACCAAATACTGTCCTTCTA
GTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATA
AGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCG
AACGACCTACACCGAACTGAGATACCTACAGCGTGAGCTATGAGAAAGCG
CCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTT
TGTGATGCTCGTCAGGGGGGCGGAGCCTATGGAAAAACGCCAGCAACGC
GCCTTTTTACGGTTCCTGGCCTTTTGCTGGCCTTTTGCTCACATGTTCTT
TCCTGCGTTATCCCCTGATTCTGTGGATAACCGTATTACCGCCTTTGAGT
GAGCTGATACCGCTCGCCGCAGCCGAACGACCGAGCGCAGCGAGTCAGTG
AGCGAGGAAGCGGAAGAGCGCCTGATGCGGTATTTTCTCCTTACGCATCT
GTGCGGTATTTCACACCGCATATATGGTGCACTCTCAGTACAATCTGCTC
TGATGCCGCATAGTTAAGCCAGTATACACTCCGCTATCGCTACGTGACTG
GGTCATGGCTGCGCCCCGACACCCGGCAACACCCGCTGACGCGCCCTGAC
GGGCTTGTCTGCTCCCGGCATCCGCTTACAGACAAGCTGTGACCGTCTCC
GGGAGCTGCATGTGTCAGAGGTTTTCACCGTCATCACCGAAACGCGCGAG
GCAGCTGCGGTAAAGCTCATCAGCGTGGTCGTGAAGCGATTCACAGATGT
CTGCCTGTTCATCCGCGTCCAGCTCGTTGAGTTTCTCCAGAAGCGTTAAT
GTCTGGCTTCTGATAAAGCGGGCCATGTTAAGGGCGGTTTTTTCCTGTTT
GGTCACTGATGCCTCCGTGTAAGGGGGATTTCTGTTCATGGGGGTAATGA
TACCGATGAAACGAGAGAGGATGCTCACGATACGGGTTACTGATGATGAA
CATGCCCGGTTACTGGAACGTTGTGAGGGTAAACAACTGGCGGTATGGAT
GCGGCGGGACCAGAGAAAAATCACTCAGGGTCAATGCCAGCGCTTCGTTA
ATACAGATGTAGGTGTTCCACAGGGTAGCCAGCAGCATCCTGCGATGCAG -continued

TABLE OF SEQUENCES

ATCCGGAACATAATGGTGCAGGGCGCTGACTTCCGCGTTTCCAGACTTTA
CGAAACACGGAAACCGAAGACCATTCATGTTGTTGCTCAGGTCGCAGACG
TTTTGCAGCAGCAGTCGCTTCACGTTCGCTCGCGTATCGGTGATTCATTC
TGCTAACCAGTAAGGCAACCCCGCCAGCCTAGCCGGGTCCTCAACGACAG
GAGCACGATCATGCGCACCCGTGGGGCCGCCATGCCGGCGATAATGGCCT
GCTTCTCGCCGAAACGTTTGGTGGCGGGACCAGTGACGAAGGCTTGAGCG
AGGGCGTGCAAGATTCCGAATACCGCAAGCGACAGGCCGATCATCGTCGC
GCTCCAGCGAAAGCGGTCCTCGCCGAAAATGACCCAGAGCGCTGCCGGCA
CCTGTCCTACGAGTTGCATGATAAAGAAGACAGTCATAAGTGCGGCGACG
ATAGTCATGCCCCGCGCCCACCGGAAGGAGCTGACTGGGTTGAAGGCTCT
CAAGGGCATCGGTCGAGATCCCGGTGCCTAATGAGTGAGCTAACTTACAT
TAATTGCGTTGCGCTCACTGCCCGCTTTCCAGTCGGGAAACCTGTCGTGC
CAGCTGCATTAATGAATCGGCCAACGCGCGGGGAGAGGCGGTTTGCGTAT
TGGGCGCCAGGGTGGTTTTTCTTTTCACCAGTGAGACGGGCAACAGCTGA
TTGCCCTTCACCGCCTGGCCCTGAGAGAGTTGCAGCAAGCGGTCCACGCT
GGTTTGCCCCAGCAGGCGAAAATCCTGTTTGATGGTGGTTAACGGCGGGA
TATAACATGAGCTGTCTTCGGTATCGTCGTATCCCACTACCGAGATATCC
GCACCAACGCGCAGCCCGGACTCGGTAATGGCGCGCATTGCGCCCAGCGC
CATCTGATCGTTGGCAACCAGCATCGCAGTGGGAACGATGCCCTCATTCA
GCATTTGCATGGTTTGTTGAAAACCGGACATGGCACTCCAGTCGCCTTCC
CGTTCCGCTATCGGCTGAATTTGATTGCGAGTGAGATATTTATGCCAGCC
AGCCAGACGCAGACGCGCCGAGACAGAACTTAATGGGCCCGCTAACACCG
CGATTTGCTGGTGACCCAATGCGACCAGATGCTCCACGCCCAGTCGCGTA
CCGTCTTCATGGGAGAAAATAATACTGTTGATGGGTGTCTGGTCAGAGAC
ATCAAGAAATAACGCCGGAACATTAGTGCAGGCAGCTTCCACAGCAATGG
CATCCTGGTCATCCAGCGGATAGTTAATGATCAGCCCACTGACGCGTTGC
GCGAGAAGATTGTGCACCGCCGCTTTACAGGCTTCGACGCCGCTTCGTTC
TACCATCGACACCACCACGCTGGCACCCAGTTGATCGGCGCGAGATTTAA
TCGCCGCGACAATTTGCGACGGCGCGTGCAGGGCCAGACTGGAGGTGGCA
ACGCCAATCAGCAACGACTGTTTGCCCGCCAGTTGTTGTGCCACGCGGTT
GGGAATGTAATTCAGCTCCGCCATCGCCGCTTCCACTTTTTCCCGCGTTT
TCGCAGAAACGTGGCTGGCCTGGTTCACCACGCGGGAAACGGTCTGATAA
GAGACACCGGCATACTCTGCGACATCGTATAACGTTACTGGTTTCACATT
CACCACCCTGAATTGACTCTCTTCCGGGCGCTATCATGCCATACCGCGAA
AGGTTTTGCGCCATTCGATGGTGTCCGGGATCTCGACGCTCTCCCTTATG
CGACTCCTGCATTAGGAAGCAGCCCAGTAGTAGGTTGAGGCCGTTGAGCA
CCGCCGCCGCAAGGAATGGTGCATGCAAGGAGATGGCGCCCAACAGTCCC
CCGGCCACGGGGCCTGCCACCATACCCACGCCGAAACAAGCGCTCATGAG
CCCGAAGTGGCGAGCCCGATCTTCCCCATCGGTGATGTCGGCGATATAGG
CGCCAGCAACCGCACCTGTGGCGCCGGTGATGCCGGCCACGATGCGTCCG
GCGTAGAGGATCGAGATCTCGATCCCGCGAAATTAATACGACTCACTATA
GGGGAATTGTGAGCGGATAACAATTCCCCTCTAGAAATAATTTTGTTTAA
CTTTAAGAAGGAGATATACCATGGGTGGCGGTACTAGTGGTGGCGGCTCA
GGTACCTAACTCGAGCACCACCACCACCACCACTGAGATCCGGCTGCTAA
CAAAGCCCGAAAGGAAGCTGAGTTGGCTGCTGCCACCGCTGAGCAATAAC
TAGCATAACCCCTTGGGGCCTCTAAACGGGTCTTGAGGGGTTTTIT GCTG
AAAGGAGGAACTATATCCGGAT

SEQ ID NO: 22:
Frame-shift stuffer with stops in all three
reading frames to be inserted into NdeI/BamHI
cloning site of GFPcp and DHFR insertion vector
constructs:
CATATGTAATTAATTAATTGGATCC SEQ ID NO: 23:
DHFR insertion vector with flanking NcoI and KpnI
or XhoI sites for cloning into pET vector
(see SEQ ID NO 21, supra):
ACCATGGGTATCAGTCTGATTGCGGCGTTAGCGGTAGATCGCGTTATCGG
CATGGAAAACGCCATGCCGTGGAACCTGCCTGCCGATCTCGCCTGGTTTA
AACGCAACACCTTAAATAAACCCGTAATTATGGGCCGCCATACCAGGGAA
TCCATCGGTCGTCCGTTGCCAGGACGCAAAATATTATCCTCAGCAGTCA
ACCGGGTACGGACGATCGCGTAACGTGGGTGAAGTCGGTGGATGAAGCCA
TCGCGGCGTGTGGTGGTGGCGGTGGTTCTGGTGGTGGCTCTCATATGGGC
GGTGGTTCTGGATCCGGCGGTGGTTCTGGCGGCGGTTCTGGTGACGTACC
AGAAATCATGGTGATTGGCGGCGGTCGCGTTTATGAGCAGTTCCTGCCGA
AAGCGCAAAAACTGTACCTGACGCATATCGACGCAGAAGTGGAAGGCGAC
ACCCATTTTCCGGATTACGAGCCGGATGACTGGGAATCGGTATTCAGCGA
ATTCCACGACGCTGATGCGCAGAACTCTCACAGCTATTGTTTTGAGATTC
TGGAGCGGCGGTAAGGTACCCTCGAG SEQ ID NO: 24:
Frame-shift stuffer with blunt cloning sites StuI,
flanked by NdeI and BamHI, for cloning into DHFR
insertion construct (see SEQ ID NO 23, supra).
Vector must cut twice, and insert must have
3N + 2 nucleotides to restore NdeI and BamHI to
be inframe with the flanking DHFR scaffolding
fragments:
CATATGTCAGGCCTTAACTAAGTAATAGGCCTCTGGATCC SEQ ID NO: 30:
DHFR insertion vector with flanking NcoI and KpnI
or XhoI sites for cloning into pET vector (see SEQ
ID NO 21, supra) and containing the stuffer
SEQ ID NO 24:
ACCATGGGTATCAGTCTGATTGCGGCGTTAGCGGTAGATCGCGTTATCGG
CATGGAAAACGCCATGCCGTGGAACCTGCCTGCCGATCTCGCCTGGTTTA
AACGCAACACCTTAAATAAACCCGTAATTATGGGCCGCCATACCAGGGAA
TCCATCGGTCGTCCGTTGCCAGGACGCAAAAATATTATCCTCAGCAGTCA
ACCGGGTACGGACGATCGCGTAACGTGGGTGAAGTCGGTGGATGAAGCCA
TCGCGGCGTGTGGTGGTGGCGGTGGTTCTGGTGGTGGCTCTCATATGTCA
GGCCTTAACTAAGTAATAGGCCTCTGGATCCGGCGGTGGTTCTGGCGGCG
GTTCTGGTGACGTACCAGAAATCATGGTGATTGGCGGCGGTCGCGTTTAT
GAGCAGTTCCTGCCGAAAGCGCAAAAACTGTACCTGACGCATATCGACGC
AGAAGTGGAAGGCGACACCCATTTTCCGGATTACGAGCCGGATGACTGGG
AATCGGTATTCAGCGAATTCCACGACGCTGATGCGCAGAACTCTCACAGC
TATTGTTTTGAGATTCTGGAGCGGCGGTAAGGTACCCTCGAG

LITERATURE CITED

Arai, M., K. Maki, et al. (2003). "Testing the relationship between foldability and the early folding events of dihydrofolate reductase from *Escherichia coli*." *J Mol Biol* 328(1): 273-88.

Armstrong, N., A. de Lencastre, et al. (1999). "A new protein folding screen:
application to the ligand binding domains of a glutamate and kainate receptor and to lysozyme and carbonic anhydrase." *Protein Sci* 8(7): 1475-83.

Baneyx, F. (1999). "Recombinant protein expression in *Escherichia coli*." *Curr Opin Biotechnol* 10(5): 411-21.

Fahnert, B., H. Lilie, et al. (2004). "Inclusion bodies: formation and utilisation." *Adv Biochem Eng Biotechnol* 89: 93-142.

Goh, C. S., N. Lan, et al. (2004). "Mining the structural genomics pipeline: identification of protein properties that affect high-throughput experimental analysis." *J Mol Biol* 336(1): 115-30.

Iwakura, M., T. Nakamura, et al. (2000). "Systematic circular permutation of an entire protein reveals essential folding elements." *Nat Struct Biol* 7(7): 580-5.

Maki, K. and M. Iwakura (2001). "Folding elements: an essential unit of foldability revealed by systematic circular permutation analysis." *Seikagaku* 73(1): 42-6.

Makrides, S. C. (1996). "Strategies for achieving high-level expression of genes in *Escherichia coli*." *Microbiol Rev* 60(3): 512-38.

Murai, T., S. Mori, et al. (2000). "Induction of hepatocellular carcinoma with high metastatic potential in WS/Shi rats: discovery of an inbred strain highly susceptible to the liver carcinogen N-nitrosomorpholine." *Oncol Res* 12(3): 121-6.

Smith, V. F. and C. R. Matthews (2001). "Testing the role of chain connectivity on the stability and structure of dihydrofolate reductase from *E. coli*: fragment complementation and circular permutation reveal stable, alternatively folded forms." *Protein Sci* 10(1): 116-28.

Terwilliger, T. C. (2004). "Structures and technology for biologists." *Nat Struct Mol Biol* 11(4): 296-7.

Waldo, G. S., B. M. Standish, et al. (1999). "Rapid protein-folding assay using green fluorescent protein." *Nature Biotechnology* 17(#7): 691-695.

Yokoyama, S. (2003). "Protein expression systems for structural genomics and proteomics." *Curr Opin Chem Biol* 7(1): 39-43.

What is claimed is:

1. An isolated nucleic acid comprising a polynucleotide encoding a dihydrofolate reductase DHFR variant having the sequence of nucleotide residues 1-592 or 10-577 of SEQ ID NO: 30.

2. A vector comprising the nucleic acid of claim 1.

3. The vector of claim 2, which is an expression vector capable of expressing the DHFR variant encoded therein in a host cell.

4. A host cell comprising the vector of claim 2 or 3.

5. The host cell of claim 4, which is a prokaryotic host cell.

6. The host cell of claim 4, which is an *E. coli* cell.

7. A kit comprising the vector of claim 4.

8. A method for detecting whether a polynucleotide encodes and open reading frame, comprising:
   (a) inserting the polynucleotide into the cloning site of the expression vector of claim 3, thereby encoding a fusion protein; and,
   (b) expressing the fusion protein in an *E. coli* cell cultured in media supplemented with 0.25-8.0 μg/ml trimethoprim;

wherein survival of the *E. coli* cell expressing the fusion protein indicates that the polynucleotide encodes an open reading frame.

* * * * *

SEQUENCE LISTING

<160> NUMBER OF SEQ ID NOS: 30

<210> SEQ ID NO 1
<211> LENGTH: 714
<212> TYPE: DNA
<213> ORGANISM: Artificial Sequence
<220> FEATURE:
<223> OTHER INFORMATION: Sequence encoding GFP variant

<400> SEQUENCE: 1

```
atgagcaaag gagaagaact tttcactgga gttgtcccaa ttcttgttga attagatggt      60
gatgttaatg ggcacaaatt ttctgtcagt ggagagggtg aaggtgatgc tacatacgga     120
aaactcaccc ttaaatttat ttgcactact ggaaaactac ctgttccatg gccaacactt     180
gtcactactc tgacctatgg tgttcaatgc ttttcccgtt atccggatca catgaaacgg     240
catgactttt tcaagagtgc catgcccgaa ggttatgtac aggaacgcac tatatctttc     300
aaagatgacg ggaactacaa gacgcgtgct gaagtcaagt ttgaaggtga taccttgtt     360
aatcgtatcg agttaaaagg tattgatttt aaagaagatg gaaacattct cggacacaaa     420
ctcgagtaca actataactc acacaatgta tacatcacgg cagacaaaca aaagaatgga     480
atcaaagcta acttcaaaat tcgccacaac attgaagatg gttccgttca actagcagac     540
cattatcaac aaaatactcc aattggcgat ggccctgtcc ttttaccaga caaccattac     600
ctgtcgacac aatctgccct ttcgaaagat cccaacgaaa agcgtgacca catggtcctt     660
cttgagtttg taactgctgc tgggattaca catggcatgg atgagctcta caaa           714
```

<210> SEQ ID NO 2
<211> LENGTH: 238
<212> TYPE: PRT
<213> ORGANISM: Artificial Sequence
<220> FEATURE:
<223> OTHER INFORMATION: GFP variant

<400> SEQUENCE: 2

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140
```

```
Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Ser Ala Leu Ser
    195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235
```

<210> SEQ ID NO 3
<211> LENGTH: 714
<212> TYPE: DNA
<213> ORGANISM: Artificial Sequence
<220> FEATURE:
<223> OTHER INFORMATION: Sequence encoding "superfolder" GFP variant

<400> SEQUENCE: 3

```
atgagcaaag gagaagaact tttcactgga gttgtcccaa ttcttgttga attagatggt      60
gatgttaatg ggcacaaatt ttctgtccgt ggagagggtg aaggtgatgc tacaaacgga     120
aaactcaccc ttaaatttat ttgcactact ggaaaactac ctgttccatg gccaacactt     180
gtcactactc tgacctatgg tgttcaatgc ttttcccgtt atccggatca catgaaacgg     240
catgactttt tcaagagtgc catgcccgaa ggttatgtac aggaacgcac tatatctttc     300
aaagatgacg ggacctacaa gacgcgtgct gaagtcaagt ttgaaggtga tacccttgtt     360
aatcgtatcg agttaaaagg tattgatttt aaagaagatg gaaacattct cggacacaaa     420
ctcgagtaca actttaactc acacaatgta tacatcacgg cagacaaaca aaagaatgga     480
atcaaagcta acttcaaaat tcgccacaac gttgaagatg gttccgttca actagcagac     540
cattatcaac aaaatactcc aattggcgat ggccctgtcc ttttaccaga caaccattac     600
ctgtcgacac aatctgtcct ttcgaaagat cccaacgaaa agcgtgacca catggtcctt     660
cttgagtttg taactgctgc tgggattaca catggcatgg atgagctcta caaa           714
```

<210> SEQ ID NO 4
<211> LENGTH: 238
<212> TYPE: PRT
<213> ORGANISM: Artificial Sequence
<220> FEATURE:
<223> OTHER INFORMATION: "superfolder" GFP variant

<400> SEQUENCE: 4

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95
```

```
Thr Ile Ser Phe Lys Asp Asp Gly Thr Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235
```

<210> SEQ ID NO 5
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 5

```
accatgggtg gcggtactag cggaggcggt agcgctagtg atggttccgt tcaactagca    60
gaccattatc aacaaaatac tccaattggc gatggccctg tccttttacc agacaaccat   120
tacctgtcga cacaatctgc cctttcgaaa gatcccaacg aaaagcgtga ccacatggtc   180
cttcttgagt ttgtaactgc tgctgggatt acacatggca tggatgaact ctacaaaggc   240
ggtgggtcgg gcgggggctc ccatatgggc ggttcaggat ccggtggagg gtcaggggc    300
ggatcaagca aggagaaga actttcact ggagttgtcc caattcttgt tgaattagat    360
ggtgatgtta atgggcacaa attttctgtc agtggagagg gtgaaggtga tgctacatac   420
ggaaaactca cccttaaatt tatttgcact actggaaaac tacctgttcc atggccaaca   480
cttgtcacta ctctgaccta tggtgttcaa tgcttttccc gttatccgga tcacatgaaa   540
cggcatgact ttttcaagag tgccatgccc gaaggttatg tacaggaacg cactatatct   600
ttcaaagatg acgggaacta caagacgcgt gctgaagtca agtttgaagg tgatacccctt   660
gttaatcgta tcgagttaaa gggtattgat tttaaagagg atggaaacat tctcggacac   720
aaactcgagt acaactataa ctcacacaat gtatacatca cggcagacaa acaaaagaat   780
ggaatcaaag ctaacttcaa aattcgccac aacattgaag atggtaccta a            831
```

<210> SEQ ID NO 6
<211> LENGTH: 276
<212> TYPE: PRT
<213> ORGANISM: Artificial Sequence
<220> FEATURE:
<223> OTHER INFORMATION: GFP circular permutant

<400> SEQUENCE: 6

```
Thr Met Gly Gly Gly Thr Ser Gly Gly Gly Ser Ala Ser Asp Gly Ser
1               5                   10                  15
```

```
Val Gln Leu Ala Asp His Tyr Gln Gln Asn Thr Pro Ile Gly Asp Gly
             20                  25                  30

Pro Val Leu Leu Pro Asp Asn His Tyr Leu Ser Thr Gln Ser Ala Leu
         35                  40                  45

Ser Lys Asp Pro Asn Glu Lys Arg Asp His Met Val Leu Leu Glu Phe
     50                  55                  60

Val Thr Ala Ala Gly Ile Thr His Gly Met Asp Glu Leu Tyr Lys Gly
 65                  70                  75                  80

Gly Gly Ser Gly Gly Gly Ser His Met Gly Gly Ser Gly Ser Gly Gly
                 85                  90                  95

Gly Ser Gly Gly Gly Ser Ser Lys Gly Glu Glu Leu Phe Thr Gly Val
            100                 105                 110

Val Pro Ile Leu Val Glu Leu Asp Gly Asp Val Asn Gly His Lys Phe
        115                 120                 125

Ser Val Ser Gly Glu Gly Glu Gly Asp Ala Thr Tyr Gly Lys Leu Thr
    130                 135                 140

Leu Lys Phe Ile Cys Thr Thr Gly Lys Leu Pro Val Pro Trp Pro Thr
145                 150                 155                 160

Leu Val Thr Thr Leu Thr Tyr Gly Val Gln Cys Phe Ser Arg Tyr Pro
                165                 170                 175

Asp His Met Lys Arg His Asp Phe Phe Lys Ser Ala Met Pro Glu Gly
            180                 185                 190

Tyr Val Gln Glu Arg Thr Ile Ser Phe Lys Asp Asp Gly Asn Tyr Lys
        195                 200                 205

Thr Arg Ala Glu Val Lys Phe Glu Gly Asp Thr Leu Val Asn Arg Ile
    210                 215                 220

Glu Leu Lys Gly Ile Asp Phe Lys Glu Asp Gly Asn Ile Leu Gly His
225                 230                 235                 240

Lys Leu Glu Tyr Asn Tyr Asn Ser His Asn Val Tyr Ile Thr Ala Asp
                245                 250                 255

Lys Gln Lys Asn Gly Ile Lys Ala Asn Phe Lys Ile Arg His Asn Ile
            260                 265                 270

Glu Asp Gly Thr
        275

<210> SEQ ID NO 7
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 7
accatgggtg gcggtactag cggaggcggt agcgctagtg atggttccgt tcaactagca      60
gaccattatc aacaaaatac tccaattggc gatggccctg tccttttacc agacaaccat     120
tacctgtcga cacaatctgt cctttcgaaa gatcccaacg aaaagcgtga ccacatggtc     180
cttcttgagt ttgtaactgc tgctgggatt acacatggca tggatgagct ctacaaaggc     240
ggtgggtcgg gcggggctc ccatatgggc ggttcaggat ccgtggagg gtcaggggc        300 ggatcaagca aaggagaaga acttttcact ggagttgtcc caattcttgt tgaattagat     360
ggtgatgtta atgggcacaa attttctgtc agaggagagg gtgaaggtga tgctacaaac     420
ggaaaactca cccttaaatt tatttgcact actggaaaac tacctgttcc atggccaaca     480
cttgtcacta ctctgaccta tggtgttcaa tgcttttccc gttatccgga tcacatgaaa     540
```

```
cggcatgact ttttcaggag tgccatgccc gaaggttatg tacaggaacg cactatatct    600
ttcaaagatg acgggaacta caagacgcgt gctgaagtca gtttgaaggt gatacccctt    660
gttaatcgta tcgagttaaa gggtactgat tttaaagaag atggaaacat tctcggacac    720
aaactcgagt acaactttaa ctcacacaat gtatacatca cggcagacaa acaaaagaat    780
ggaatcaaag ctaacttcaa aattcgccac aacgttgaag atggtaccta a             831
```

<210> SEQ ID NO 8
<211> LENGTH: 276
<212> TYPE: PRT
<213> ORGANISM: Artificial Sequence
<220> FEATURE:
<223> OTHER INFORMATION: GFP circular permutant

<400> SEQUENCE: 8

```
Thr Met Gly Gly Gly Thr Ser Gly Gly Gly Ser Ala Ser Asp Gly Ser
1               5                   10                  15

Val Gln Leu Ala Asp His Tyr Gln Gln Asn Thr Pro Ile Gly Asp Gly
            20                  25                  30

Pro Val Leu Leu Pro Asp Asn His Tyr Leu Ser Thr Gln Ser Val Leu
        35                  40                  45

Ser Lys Asp Pro Asn Glu Lys Arg Asp His Met Val Leu Leu Glu Phe
    50                  55                  60

Val Thr Ala Ala Gly Ile Thr His Gly Met Asp Glu Leu Tyr Lys Gly
65                  70                  75                  80

Gly Gly Ser Gly Gly Gly Ser His Met Gly Gly Ser Gly Ser Gly Gly
                85                  90                  95

Gly Ser Gly Gly Gly Ser Ser Lys Gly Glu Glu Leu Phe Thr Gly Val
            100                 105                 110

Val Pro Ile Leu Val Glu Leu Asp Gly Asp Val Asn Gly His Lys Phe
        115                 120                 125

Ser Val Arg Gly Glu Gly Glu Gly Asp Ala Thr Asn Gly Lys Leu Thr
    130                 135                 140

Leu Lys Phe Ile Cys Thr Thr Gly Lys Leu Pro Val Pro Trp Pro Thr
145                 150                 155                 160

Leu Val Thr Thr Leu Thr Tyr Gly Val Gln Cys Phe Ser Arg Tyr Pro
                165                 170                 175

Asp His Met Lys Arg His Asp Phe Phe Arg Ser Ala Met Pro Glu Gly
            180                 185                 190

Tyr Val Gln Glu Arg Thr Ile Ser Phe Lys Asp Gly Asn Tyr Lys
        195                 200                 205

Thr Arg Ala Glu Val Lys Phe Glu Gly Asp Thr Leu Val Asn Arg Ile
    210                 215                 220

Glu Leu Lys Gly Thr Asp Phe Lys Glu Asp Gly Asn Ile Leu Gly His
225                 230                 235                 240

Lys Leu Glu Tyr Asn Phe Asn Ser His Asn Val Tyr Ile Thr Ala Asp
                245                 250                 255

Lys Gln Lys Asn Gly Ile Lys Ala Asn Phe Lys Ile Arg His Asn Val
            260                 265                 270

Glu Asp Gly Thr
        275
```

<210> SEQ ID NO 9
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 9

```
accatgggtg cggtactag cggaggcggt agcgctagtg atggttccgt caactagca      60
gaccattatc aacaaaatac tccaattggc gatggccctg tccttttacc agacaaccat   120
tacctgtcga cacaatctgc cctttcgaaa gatcccaacg aaaagcgtga ccacatggtc   180
cttcttgagt ttgtaactgc tgctgggatt acacatggca tggatgagct ctacaaaggc   240
ggtgggtcgg gcggggggcct ccatatgggc ggttcaggat ccgtggagg gtcaggggc    300
ggatcaagca aggagaaga acttttcact ggagttgtcc caattcttgt tgaattagat   360
ggtgatgtta atgggcacaa attttctgtc agaggagagg gtgaaggtga tgctacaaac   420
ggaaaactca cccttaaatt tatttgcact actggaaaac tacctgttcc atggccaaca   480
cttgtcacta ctctgaccta tggtgttcaa tgcttttccc gttatccgga tcacatgaaa   540
cggcatgact ttttcaggag tgccatgccc gaaggttatg tacaggaacg cactatatct   600
ttcaaagatg acgggaacta caagacgcgt gctgaagtca agtttgaagg tgataccctt   660
gttaatcgta tcgagttaaa gggtactgat tttaagaag atggaaacat tctcggacac    720
aaactcgagt acaactttaa ctcacacaat gtatacatca cggcagacaa acaaaagaat   780
ggaatcaaag ctaacttcaa aattcgccac aacgttgaag atggtaccta a             831
```

<210> SEQ ID NO 10
<211> LENGTH: 276
<212> TYPE: PRT
<213> ORGANISM: Artificial Sequence
<220> FEATURE:
<223> OTHER INFORMATION: GFP circular permutant

<400> SEQUENCE: 10

```
Thr Met Gly Gly Gly Thr Ser Gly Gly Gly Ser Ala Ser Asp Gly Ser
1               5                   10                  15

Val Gln Leu Ala Asp His Tyr Gln Gln Asn Thr Pro Ile Gly Asp Gly
            20                  25                  30

Pro Val Leu Leu Pro Asp Asn His Tyr Leu Ser Thr Gln Ser Ala Leu
        35                  40                  45

Ser Lys Asp Pro Asn Glu Lys Arg Asp His Met Val Leu Leu Glu Phe
    50                  55                  60

Val Thr Ala Ala Gly Ile Thr His Gly Met Asp Glu Leu Tyr Lys Gly
65                  70                  75                  80

Gly Gly Ser Gly Gly Gly Leu His Met Gly Gly Ser Gly Ser Gly Gly
                85                  90                  95

Gly Ser Gly Gly Gly Ser Ser Lys Gly Glu Glu Leu Phe Thr Gly Val
            100                 105                 110

Val Pro Ile Leu Val Glu Leu Asp Gly Asp Val Asn Gly His Lys Phe
        115                 120                 125

Ser Val Arg Gly Glu Gly Glu Gly Asp Ala Thr Asn Gly Lys Leu Thr
    130                 135                 140

Leu Lys Phe Ile Cys Thr Thr Gly Lys Leu Pro Val Pro Trp Pro Thr
145                 150                 155                 160

Leu Val Thr Thr Leu Thr Tyr Gly Val Gln Cys Phe Ser Arg Tyr Pro
                165                 170                 175

Asp His Met Lys Arg His Asp Phe Phe Arg Ser Ala Met Pro Glu Gly
            180                 185                 190
```

```
Tyr Val Gln Glu Arg Thr Ile Ser Phe Lys Asp Asp Gly Asn Tyr Lys
        195                 200                 205

Thr Arg Ala Glu Val Lys Phe Glu Gly Asp Thr Leu Val Asn Arg Ile
        210                 215                 220

Glu Leu Lys Gly Thr Asp Phe Lys Glu Asp Gly Asn Ile Leu Gly His
225                 230                 235                 240

Lys Leu Glu Tyr Asn Phe Asn Ser His Asn Val Tyr Ile Thr Ala Asp
                245                 250                 255

Lys Gln Lys Asn Gly Ile Lys Ala Asn Phe Lys Ile Arg His Asn Val
            260                 265                 270

Glu Asp Gly Thr
            275

<210> SEQ ID NO 11
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 11
accatgggtg gcggtactag cggaggcggt agcgctagtg atggttccgt tcaactagca      60
gaccattatc aacaaaatac tccaattggc gatggccctg tccttttacc agacaaccat    120
tacctgtcga cacaatctgt cctttcgaaa gatcccaacg aaaagcgtga ccacatggtc    180
cttcttgagt ttgtaactgc tgctgggatt acacatggca tggatgagct ctacaaaggc    240
ggtgggtcgg gcggggctc ccatatgggc ggttcaggat ccggtggagg gtcaggggc     300 ggatcaagca aaggagaaga acttttcact ggagttgtcc caattcttgt tgaattagat    360
ggtgatgtta atgggcacaa attttctgtc agtggagagg gtgaaggtga tgctacatac    420
ggaaaactca cccttaaatt tatttgcact actggaaaac tacctgttcc atggccaaca    480
cttgtcacta ctctgaccta tggtgttcaa tgcttttccc gttatccgga tcacatgaaa    540
cggcatgact ttttcaagag tgccatgccc gaaggttatg tacaggaacg cactatatct    600
ttcaaagatg acgggaacta caagacgcgt gctgaagtca agtttgaagg tgataccctt    660
gttaatcgta tcgagttaaa gggtattgat tttaagagg atggaaacat tctcggacac    720
aaactcgagt acaactataa ctcacacaat gtatacatca cggcagacaa acaaaagaat    780
ggaatcaaag ctaacttcaa aattcgccac aacattgaag atggtaccta a              831

<210> SEQ ID NO 12
<211> LENGTH: 276
<212> TYPE: PRT
<213> ORGANISM: Artificial Sequence
<220> FEATURE:
<223> OTHER INFORMATION: GFP circular permutant

<400> SEQUENCE: 12

Thr Met Gly Gly Gly Thr Ser Gly Gly Gly Ser Ala Ser Asp Gly Ser
1               5                   10                  15

Val Gln Leu Ala Asp His Tyr Gln Gln Asn Thr Pro Ile Gly Asp Gly
            20                  25                  30

Pro Val Leu Leu Pro Asp Asn His Tyr Leu Ser Thr Gln Ser Val Leu
        35                  40                  45

Ser Lys Asp Pro Asn Glu Lys Arg Asp His Met Val Leu Leu Glu Phe
    50                  55                  60
```

Val Thr Ala Ala Gly Ile Thr His Gly Met Asp Glu Leu Tyr Lys Gly
 65                  70                  75                  80

Gly Gly Ser Gly Gly Ser His Met Gly Gly Ser Gly Ser Gly Gly
             85                  90                  95

Gly Ser Gly Gly Ser Ser Lys Gly Glu Glu Leu Phe Thr Gly Val
            100                 105                 110

Val Pro Ile Leu Val Glu Leu Asp Gly Asp Val Asn Gly His Lys Phe
            115                 120                 125

Ser Val Ser Gly Glu Gly Glu Gly Asp Ala Thr Tyr Gly Lys Leu Thr
            130                 135                 140

Leu Lys Phe Ile Cys Thr Thr Gly Lys Leu Pro Val Pro Trp Pro Thr
145                 150                 155                 160

Leu Val Thr Thr Leu Thr Tyr Gly Val Gln Cys Phe Ser Arg Tyr Pro
                165                 170                 175

Asp His Met Lys Arg His Asp Phe Phe Lys Ser Ala Met Pro Glu Gly
                180                 185                 190

Tyr Val Gln Glu Arg Thr Ile Ser Phe Lys Asp Asp Gly Asn Tyr Lys
            195                 200                 205

Thr Arg Ala Glu Val Lys Phe Glu Gly Asp Thr Leu Val Asn Arg Ile
            210                 215                 220

Glu Leu Lys Gly Ile Asp Phe Lys Glu Asp Gly Asn Ile Leu Gly His
225                 230                 235                 240

Lys Leu Glu Tyr Asn Tyr Asn Ser His Asn Val Tyr Ile Thr Ala Asp
                245                 250                 255

Lys Gln Lys Asn Gly Ile Lys Ala Asn Phe Lys Ile Arg His Asn Ile
            260                 265                 270

Glu Asp Gly Thr
            275

<210> SEQ ID NO 13
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 13
accatgggtg gcggtactag cggaggcggt agcgctagtc aaaagaatgg aatcaaagct    60
aacttcaaaa ttcgccacaa cattgaagat ggttccgttc aactagcaga ccattatcaa   120
caaaatactc caattggcga tggccctgtc cttttaccag acaaccatta cctgtcgaca   180
caatctgccc tttcgaaaga tcccaacgaa aagcgtgacc acatggtcct tcttgagttt   240
gtaactgctg ctgggattac acatggcatg gatgaactct acaaaggcgg tgggtcgggc   300
gggggctccc atatgggcgg ttcaggatcc ggtggagggt caggggcgg atcaagcaaa   360 ggagaagaac ttttcactgg agttgtccca attcttgttg aattagatgg tgatgttaat   420
gggcacaaat tttctgtcag tggagagggt gaaggtgatg ctacatacgg aaaactcacc   480
cttaaattta tttgcactac tggaaaacta cctgttccat ggccaacact tgtcactact   540
ctgacctatg gtgttcaatg cttttcccgt tatccggatc acatgaaacg gcatgacttt   600
ttcaagagtg ccatgcccga aggttatgta caggaacgca ctatatcttt caaagatgac   660
gggaactaca agacgcgtgc tgaagtcaag tttgaaggtg ataccttgt taatcgtatc   720 gagttaaagg gtattgattt taagaggat ggaaacattc tcggacacaa actcgagtac   780
aactataact cacacaatgt atacatcacg gcagacaaac aaggtaccta a            831

<210> SEQ ID NO 14
<211> LENGTH: 276
<212> TYPE: PRT
<213> ORGANISM: Artificial Sequence
<220> FEATURE:
<223> OTHER INFORMATION: GFP circular permutant

<400> SEQUENCE: 14

```
Thr Met Gly Gly Gly Thr Ser Gly Gly Gly Ser Ala Ser Gln Lys Asn
1               5                   10                  15

Gly Ile Lys Ala Asn Phe Lys Ile Arg His Asn Ile Glu Asp Gly Ser
            20                  25                  30

Val Gln Leu Ala Asp His Tyr Gln Gln Asn Thr Pro Ile Gly Asp Gly
        35                  40                  45

Pro Val Leu Leu Pro Asp Asn His Tyr Leu Ser Thr Gln Ser Ala Leu
    50                  55                  60

Ser Lys Asp Pro Asn Glu Lys Arg Asp His Met Val Leu Leu Glu Phe
65                  70                  75                  80

Val Thr Ala Ala Gly Ile Thr His Gly Met Asp Glu Leu Tyr Lys Gly
                85                  90                  95

Gly Gly Ser Gly Gly Gly Ser His Met Gly Gly Ser Gly Ser Gly Gly
            100                 105                 110

Gly Ser Gly Gly Ser Ser Lys Gly Glu Glu Leu Phe Thr Gly Val
        115                 120                 125

Val Pro Ile Leu Val Glu Leu Asp Gly Asp Val Asn Gly His Lys Phe
    130                 135                 140

Ser Val Ser Gly Glu Gly Glu Gly Asp Ala Thr Tyr Gly Lys Leu Thr
145                 150                 155                 160

Leu Lys Phe Ile Cys Thr Thr Gly Lys Leu Pro Val Pro Trp Pro Thr
                165                 170                 175

Leu Val Thr Thr Leu Thr Tyr Gly Val Gln Cys Phe Ser Arg Tyr Pro
            180                 185                 190

Asp His Met Lys Arg His Asp Phe Phe Lys Ser Ala Met Pro Glu Gly
        195                 200                 205

Tyr Val Gln Glu Arg Thr Ile Ser Phe Lys Asp Asp Gly Asn Tyr Lys
    210                 215                 220

Thr Arg Ala Glu Val Lys Phe Glu Gly Asp Thr Leu Val Asn Arg Ile
225                 230                 235                 240

Glu Leu Lys Gly Ile Asp Phe Lys Glu Asp Gly Asn Ile Leu Gly His
                245                 250                 255

Lys Leu Glu Tyr Asn Tyr Asn Ser His Asn Val Tyr Ile Thr Ala Asp
            260                 265                 270

Lys Gln Gly Thr
        275
```

<210> SEQ ID NO 15
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 15
accatgggtg gcggtactag cggaggcggt agcgctagtc aaaagaatgg aatcaaagct    60
aacttcaaaa ttcgccacaa cgttgaagat ggttccgttc aactagcaga ccattatcaa   120
caaaatactc caattggcga tggccctgtc cttttaccag acaaccatta cctgtcgaca   180

```
caatctgtcc tttcgaaaga tcccaacgaa aagcgtgacc acatggtcct tcttgagttt      240
gtaactgctg ctgggattac acatggcatg gatgagctct acaaaggcgg tgggtcgggc      300
gggggctccc atatgggcgg ttcaggatcc ggtggagggt caggggcgg atcaagcaaa       360 ggagaagaac ttttcactgg agttgtccca attcttgttg aattagatgg tgatgttaat      420
gggcacaaat tttctgtcag aggagagggt gaaggtgatg ctacaaacgg aaaactcacc      480
cttaaattta tttgcactac tggaaaacta cctgttccat ggccaacact tgtcactact      540
ctgacctatg gtgttcaatg ctttccccgt tatccggatc acatgaaacg catgactt        600 ttcaagagtg ccatgcccga aggttatgta caggaacgca ctatatcttt caaagatgac      660
gggaactaca agacgcgtgc tgaagtcaag tttgaaggtg ataccttgt taatcgtatc       720 gagttaaagg gtactgattt taagaagat ggaaacattc tcggacacaa actcgagtac       780
aactttaact cacacaatgt atacatcacg gcagacaaac aaggtaccta a                831
```

<210> SEQ ID NO 16
<211> LENGTH: 276
<212> TYPE: PRT
<213> ORGANISM: Artificial Sequence
<220> FEATURE:
<223> OTHER INFORMATION: GFP circular permutant

<400> SEQUENCE: 16

```
Thr Met Gly Gly Gly Thr Ser Gly Gly Gly Ser Ala Ser Gln Lys Asn
1               5                   10                  15
Gly Ile Lys Ala Asn Phe Lys Ile Arg His Asn Val Glu Asp Gly Ser
            20                  25                  30
Val Gln Leu Ala Asp His Tyr Gln Gln Asn Thr Pro Ile Gly Asp Gly
        35                  40                  45
Pro Val Leu Leu Pro Asp Asn His Tyr Leu Ser Thr Gln Ser Val Leu
    50                  55                  60
Ser Lys Asp Pro Asn Glu Lys Arg Asp His Met Val Leu Leu Glu Phe
65                  70                  75                  80
Val Thr Ala Ala Gly Ile Thr His Gly Met Asp Gly Leu Tyr Lys Gly
                85                  90                  95
Gly Gly Ser Gly Gly Gly Ser His Met Gly Gly Ser Gly Ser Gly Gly
            100                 105                 110
Gly Ser Gly Gly Gly Ser Ser Lys Gly Glu Glu Leu Phe Thr Gly Val
        115                 120                 125
Val Pro Ile Leu Val Glu Leu Asp Gly Asp Val Asn Gly His Lys Phe
    130                 135                 140
Ser Val Arg Gly Glu Gly Glu Gly Asp Ala Thr Asn Gly Lys Leu Thr
145                 150                 155                 160
Leu Lys Phe Ile Cys Thr Thr Gly Lys Leu Pro Val Pro Trp Pro Thr
                165                 170                 175
Leu Val Thr Thr Leu Thr Tyr Gly Val Gln Cys Phe Ser Arg Tyr Pro
            180                 185                 190
Asp His Met Lys Arg His Asp Phe Phe Lys Ser Ala Met Pro Glu Gly
        195                 200                 205
Tyr Val Gln Glu Arg Thr Ile Ser Phe Lys Asp Asp Gly Asn Tyr Lys
    210                 215                 220
Thr Arg Ala Glu Val Lys Phe Glu Gly Asp Thr Leu Val Asn Arg Ile
225                 230                 235                 240
Glu Leu Lys Gly Thr Asp Phe Lys Glu Asp Gly Asn Ile Leu Gly His
                245                 250                 255
```

-continued

```
Lys Leu Glu Tyr Asn Phe Asn Ser His Asn Val Tyr Ile Thr Ala Asp
            260                 265                 270
Lys Gln Gly Thr
        275
```

<210> SEQ ID NO 17
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 17

```
accatgggtg gcggtactag cggaggcggt agcgctagtc aaaagaatgg aatcaaagct    60
aacttcaaaa ttcgccacaa cattgaagat ggttccgttc aactagcaga ccattatcaa   120
caaaatactc caattggcga tggccctgtc cttttaccag acaaccatta cctgtcgaca   180
caatctgccc tttcgaaaga tcccaacgaa aagcgtgacc acatggtcct tcttgagttt   240
gtaactgctg ctgggattac acatggcatg gatgagctct acaaaggcgg tgggtcgggc   300
gggggctccc atatgggcgg ttcaggatcc ggtggagggt caggggggcgg atcaagcaaa   360
ggagaagaac ttttcactgg agttgtccca attcttgttg aattagatgg tgatgttaat   420
gggcacaaat tttctgtcag aggagagggt gaaggtgatg ctacaaacgg aaaactcacc   480
cttaaattta tttgcactac tggaaaacta cctgttccat ggccaacact tgtcactact   540
ctgacctatg gtgttcaatg cttttcccgt tatccggatc acatgaaacg gcatgacttt   600
ttcaagagtg ccatgcccga aggttatgta caggaacgca ctatatcttt caaagatgac   660
gggaactaca agacgcgtgc tgaagtcaag tttgaaggtg ataccttgt taatcgtatc   720
gagttaaagg gtactgattt taaagaaaat ggaaacattc tcggacacaa actcgagtac   780
aactttaact cacacaatgt atacatcacg gcagacaaac aaggtaccta a            831
```

<210> SEQ ID NO 18
<211> LENGTH: 276
<212> TYPE: PRT
<213> ORGANISM: Artificial Sequence
<220> FEATURE:
<223> OTHER INFORMATION: GFP circular permutant

<400> SEQUENCE: 18

```
Thr Met Gly Gly Gly Thr Ser Gly Gly Gly Ser Ala Ser Gln Lys Asn
1               5                   10                  15
Gly Ile Lys Ala Asn Phe Lys Ile Arg His Asn Ile Glu Asp Gly Ser
            20                  25                  30
Val Gln Leu Ala Asp His Tyr Gln Gln Asn Thr Pro Ile Gly Asp Gly
        35                  40                  45
Pro Val Leu Leu Pro Asp Asn His Tyr Leu Ser Thr Gln Ser Ala Leu
    50                  55                  60
Ser Lys Asp Pro Asn Glu Lys Arg Asp His Met Val Leu Leu Glu Phe
65                  70                  75                  80
Val Thr Ala Ala Gly Ile Thr His Gly Met Asp Glu Leu Tyr Lys Gly
                85                  90                  95
Gly Gly Ser Gly Gly Gly Ser His Met Gly Gly Ser Gly Ser Gly Gly
            100                 105                 110
Gly Ser Gly Gly Gly Ser Ser Lys Gly Glu Glu Leu Phe Thr Gly Val
        115                 120                 125
```

-continued

```
Val Pro Ile Leu Val Glu Leu Asp Gly Asp Val Asn Gly His Lys Phe
    130                 135                 140
Ser Val Arg Gly Glu Gly Glu Gly Asp Ala Thr Asn Gly Lys Leu Thr
145                 150                 155                 160
Leu Lys Phe Ile Cys Thr Thr Gly Lys Leu Pro Val Pro Trp Pro Thr
                165                 170                 175
Leu Val Thr Thr Leu Thr Tyr Gly Val Gln Cys Phe Ser Arg Tyr Pro
            180                 185                 190
Asp His Met Lys Arg His Asp Phe Phe Lys Ser Ala Met Pro Glu Gly
        195                 200                 205
Tyr Val Gln Glu Arg Thr Ile Ser Phe Lys Asp Asp Gly Asn Tyr Lys
    210                 215                 220
Thr Arg Ala Glu Val Lys Phe Glu Gly Asp Thr Leu Val Asn Arg Ile
225                 230                 235                 240
Glu Leu Lys Gly Thr Asp Phe Lys Glu Asn Gly Asn Ile Leu Gly His
                245                 250                 255
Lys Leu Glu Tyr Asn Phe Asn Ser His Asn Val Tyr Ile Thr Ala Asp
            260                 265                 270
Lys Gln Gly Thr
        275

<210> SEQ ID NO 19
<211> LENGTH: 831
<212> TYPE: DNA
<213> ORGANISM: Artificial Sequence
<220> FEATURE:
<223> OTHER INFORMATION: Sequence encoding GFP circular permutant

<400> SEQUENCE: 19
accatgggtg cggtactag cggaggcggt agcgctagtc aaaagaatgg aatcaaagct      60
aacttcaaaa ttcgccacaa cgttgaagat ggttccgttc aactagcaga ccattatcaa     120
caaaatactc caattggcga aggccctgtc cttttaccag acaaccatta cctgtcgaca     180
caatctgtcc tttcgaaaga tcccaacgaa aagcgtgacc acatggtcct tcttgagttt     240
gtaactgctg ctgggattac acatggcatg gatgaactct acaaaggcgg tgggtcgggc     300
gggggctccc atatgggcgg ttcaggatcc ggtggaggt caggggggcgg atcaagcaaa     360 ggagaagaac ttttcactgg agttgtccca attcttgttg aattagatgg tgatgttaat     420
gggcacaaat tttctgtcag tggagagggt gaaggtgatg ctacatacgg aaaactcacc     480
cttaaattta tttgcactac tggaaaacta cctgttccat ggccaacact tgtcactact     540
ctgacctatg gtgttcaatg cttttcccgt tatccggatc acatgaaacg gcatgacttt     600
ttcaagagtg ccatgcccga aggttatgta caggaacgca ctatatcttt caaagatgac     660
gggaactaca agacgcgtgc tgaagtcaag tttgaaggtg ataccttgt taatcgtatc     720 gagttaaagg gtattgattt taaagaggat ggaaacattc tcggacacaa actcgagtac     780
aactataact cacacaatgt atacatcacg gcagacaaac aaggtaccta a              831

<210> SEQ ID NO 20
<211> LENGTH: 276
<212> TYPE: PRT
<213> ORGANISM: Artificial Sequence
<220> FEATURE:
<223> OTHER INFORMATION: GFP circular permutant
```

<400> SEQUENCE: 20

```
Thr Met Gly Gly Gly Thr Ser Gly Gly Gly Ser Ala Ser Gln Lys Asn
1               5                   10                  15
Gly Ile Lys Ala Asn Phe Lys Ile Arg His Asn Val Glu Asp Gly Ser
            20                  25                  30
Val Gln Leu Ala Asp His Tyr Gln Gln Asn Thr Pro Ile Gly Glu Gly
        35                  40                  45
Pro Val Leu Leu Pro Asp Asn His Tyr Leu Ser Thr Gln Ser Val Leu
    50                  55                  60
Ser Lys Asp Pro Asn Glu Lys Arg Asp His Met Val Leu Leu Glu Phe
65                  70                  75                  80
Val Thr Ala Ala Gly Ile Thr His Gly Met Asp Glu Leu Tyr Lys Gly
                85                  90                  95
Gly Gly Ser Gly Gly Gly Ser His Met Gly Gly Ser Gly Ser Gly Gly
            100                 105                 110
Gly Ser Gly Gly Gly Ser Ser Lys Gly Glu Glu Leu Phe Thr Gly Val
        115                 120                 125
Val Pro Ile Leu Val Glu Leu Asp Gly Asp Val Asn Gly His Lys Phe
    130                 135                 140
Ser Val Ser Gly Glu Gly Glu Gly Asp Ala Thr Tyr Gly Lys Leu Thr
145                 150                 155                 160
Leu Lys Phe Ile Cys Thr Thr Gly Lys Leu Pro Val Pro Trp Pro Thr
                165                 170                 175
Leu Val Thr Thr Leu Thr Tyr Gly Val Gln Cys Phe Ser Arg Tyr Pro
            180                 185                 190
Asp His Met Lys Arg His Asp Phe Phe Lys Ser Ala Met Pro Glu Gly
        195                 200                 205
Tyr Val Gln Glu Arg Thr Ile Ser Phe Lys Asp Gly Asn Tyr Lys
    210                 215                 220
Thr Arg Ala Glu Val Lys Phe Glu Gly Asp Thr Leu Val Asn Arg Ile
225                 230                 235                 240
Glu Leu Lys Gly Ile Asp Phe Lys Glu Asp Gly Asn Ile Leu Gly His
                245                 250                 255
Lys Leu Glu Tyr Asn Tyr Asn Ser His Asn Val Tyr Ile Thr Ala Asp
            260                 265                 270
Lys Gln Gly Thr
        275
```

<210> SEQ ID NO 21
<211> LENGTH: 5272
<212> TYPE: DNA
<213> ORGANISM: Artificial Sequence
<220> FEATURE:
<223> OTHER INFORMATION: Sequence of pET expression vector

<400> SEQUENCE: 21

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttt agg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta     420
```

| | |
|---|---|
| acaaaaattt aacgcgaatt ttaacaaaat attaacgttt acaatttcag gtggcactttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cacgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatcctttt ttctgcgcgt aatctgctgc ttgcaaacaa aaaaaccacc gctaccagcg | 1560 |
| gtggtttgtt tgccggatca agagctacca actctttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata agtcgtgtct taccgggttg gactcaagac gatagttacc ggataaggcg | 1800 |
| cagcggtcgg gctgaacggg gggttcgtgc acacagccca gcttggagcg aacgacctac | 1860 |
| accgaactga gatacctaca gcgtgagcta tgagaaagcg ccacgcttcc cgaagggaga | 1920 |
| aaggcggaca ggtatccggt aagcggcagg gtcggaacag gagagcgcac gagggagctt | 1980 |
| ccaggggaa acgcctggta tctttatagt cctgtcgggt ttcgccacct ctgacttgag | 2040 |
| cgtcgatttt tgtgatgctc gtcaggggg cggagcctat ggaaaaacgc cagcaacgcg | 2100 |
| gcctttttac ggttcctggc cttttgctgg ccttttgctc acatgttctt tcctgcgtta | 2160 |
| tcccctgatt ctgtggataa ccgtattacc gcctttgagt gagctgatac cgctcgccgc | 2220 |
| agccgaacga ccgagcgcag cgagtcagtg agcgaggaag cggaagagcg cctgatgcgg | 2280 |
| tattttctcc ttacgcatct gtgcggtatt tcacaccgca tatatggtgc actctcagta | 2340 |
| caatctgctc tgatgccgca tagttaagcc agtatacact ccgctatcgc tacgtgactg | 2400 |
| ggtcatggct gcgccccgac acccgccaac acccgctgac gcgccctgac gggcttgtct | 2460 |
| gctcccggca tccgcttaca gacaagctgt gaccgtctcc gggagctgca tgtgtcagag | 2520 |
| gttttcaccg tcatcaccga aacgcgcgag gcagctgcgg taaagctcat cagcgtggtc | 2580 |
| gtgaagcgat tcacagatgt ctgcctgttc atccgcgtcc agctcgttga gtttctccag | 2640 |
| aagcgttaat gtctggcttc tgataaagcg ggccatgtta agggcggttt tttcctgttt | 2700 |
| ggtcactgat gcctccgtgt aagggggatt tctgttcatg ggggtaatga taccgatgaa | 2760 |
| acgagagagg atgctcacga tacgggttac tgatgatgaa catgcccggt tactgaaacg | 2820 |

```
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgaca atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatatacc atgggtggcg gtactagtgg tggcggctca    5100
ggtacctaac tcgagcacca ccaccaccac cactgagatc cggctgctaa caaagcccga    5160
```

```
aaggaagctg agttggctgc tgccaccgct gagcaataac tagcataacc ccttggggcc      5220
tctaaacggg tcttgagggg ttttttgctg aaaggaggaa ctatatccgg at              5272

<210> SEQ ID NO 22
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 22
catatgtaat taattaattg gatcc                                              25

<210> SEQ ID NO 23
<211> LENGTH: 576
<212> TYPE: DNA
<213> ORGANISM: Artificial Sequence
<220> FEATURE:
<223> OTHER INFORMATION: DHFR insertion vector

<400> SEQUENCE: 23
accatgggta tcagtctgat tgcggcgtta gcggtagatc gcgttatcgg catggaaaac        60
gccatgccgt ggaacctgcc tgccgatctc gcctggttta acgcaacac  cttaaataaa      120 cccgtaatta tgggccgcca taccagggaa tccatcggtc gtccgttgcc aggacgcaaa      180
aatattatcc tcagcagtca accgggtacg gacgatcgcg taacgtgggt gaagtcggtg      240
gatgaagcca tcgcggcgtg tggtggtggc ggtggttctg gtggtggctc tcatatgggc      300
ggtggttctg gatccggcgg tggttctggc ggcggttctg gtgacgtacc agaaatcatg      360
gtgattggcg gcggtcgcgt ttatgagcag ttcctgccga aagcgcaaaa actgtacctg      420
acgcatatcg acgcagaagt ggaaggcgac acccattttc cggattacga gccggatgac      480
tgggaatcgg tattcagcga attccacgac gctgatgcgc agaactctca cagctattgt      540
tttgagattc tggagcggcg gtaaggtacc ctcgag                                576

<210> SEQ ID NO 24
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 24
catatgtcag gccttaacta agtaataggc ctctggatcc                              40

<210> SEQ ID NO 25
<211> LENGTH: 8
<212> TYPE: PRT
<213> ORGANISM: Artificial Sequence
<220> FEATURE:
<223> OTHER INFORMATION: Linker polypeptide

<400> SEQUENCE: 25

Gly Gly Gly Ser Gly Gly Gly Ser
1               5

<210> SEQ ID NO 26
<211> LENGTH: 30
<212> TYPE: DNA
<213> ORGANISM: Artificial Sequence
<220> FEATURE:
<223> OTHER INFORMATION: Synthetic primer
```

-continued

```
<400> SEQUENCE: 26
atggtgcatg caaggagatg gcgcccaaca                                        30

<210> SEQ ID NO 27
<211> LENGTH: 30
<212> TYPE: DNA
<213> ORGANISM: Artificial Sequence
<220> FEATURE:
<223> OTHER INFORMATION: Synthetic primer

<400> SEQUENCE: 27
gaggcctcta gaggttatgc tagttattgc                                        30

<210> SEQ ID NO 28
<211> LENGTH: 36
<212> TYPE: DNA
<213> ORGANISM: Artificial Sequence
<220> FEATURE:
<223> OTHER INFORMATION: Synthetic primer

<400> SEQUENCE: 28
tagagatact gagcacatca gcaggacgca ctgacc                                 36

<210> SEQ ID NO 29
<211> LENGTH: 36
<212> TYPE: DNA
<213> ORGANISM: Artificial Sequence
<220> FEATURE:
<223> OTHER INFORMATION: Synthetic primer

<400> SEQUENCE: 29
tacttcggta cctgtaatcc cagcagcagt tacaaa                                 36

<210> SEQ ID NO 30
<211> LENGTH: 592
<212> TYPE: DNA
<213> ORGANISM: Artificial Sequence
<220> FEATURE:
<223> OTHER INFORMATION: DHFR insertion vector

<400> SEQUENCE: 30
accatgggta tcagtctgat tgcggcgtta gcggtagatc gcgttatcgg catggaaaac       60
gccatgccgt ggaacctgcc tgccgatctc gcctggttta aacgcaacac cttaaataaa      120
cccgtaatta tgggccgcca taccagggaa tccatcggtc gtccgttgcc aggacgcaaa      180
aatattatcc tcagcagtca accgggtacg gacgatcgcg taacgtgggt gaagtcggtg      240
gatgaagcca tcgcggcgtg tggtggtggc ggtggttctg gtggtggctc tcatatgtca      300
ggccttaact aagtaatagg cctctggatc cggcggtggt tctggcggcg gttctggtga      360
cgtaccagaa atcatggtga ttggcggcgg tcgcgtttat gagcagttcc tgccgaaagc      420
gcaaaaactg tacctgacgc atatcgacgc agaagtggaa ggcgacaccc attttccgga      480
ttacgagccg gatgactggg aatcggtatt cagcgaattc cacgacgctg atgcgcagaa      540
ctctcacagc tattgttttg agattctgga gcggcggtaa ggtaccctcg ag              592
```